(12) United States Patent
Vasishta

(10) Patent No.: US 8,657,732 B2
(45) Date of Patent: Feb. 25, 2014

(54) SEQUENTIALLY PROGRAMMED MAGNETIC FIELD THERAPEUTIC SYSTEM (SPMF)

(75) Inventor: Vishwanath Gopalakrishna Vasishta, Andheri (IN)

(73) Assignee: SBF Healthcare Pvt. Ltd., Bangalore (IN)

( * ) Notice: Subject to any disclaimer, the term of this patent is extended or adjusted under 35 U.S.C. 154(b) by 844 days.

(21) Appl. No.: 12/696,664

(22) Filed: Jan. 29, 2010

(65) Prior Publication Data

US 2010/0197993 A1    Aug. 5, 2010

Related U.S. Application Data

(60) Provisional application No. 61/285,712, filed on Dec. 11, 2009.

(30) Foreign Application Priority Data

Jan. 30, 2009    (IN) .......................... 184/MUM/2009

(51) Int. Cl.
*A61N 2/02*        (2006.01)
(52) U.S. Cl.
USPC ........................................................... 600/14
(58) Field of Classification Search
USPC ...................................... 600/9–14, 422, 427
See application file for complete search history.

(56) References Cited

U.S. PATENT DOCUMENTS

| 96,044 A | 10/1869 | Smith |
| 435,343 A | 8/1890 | Brown |
| 703,989 A | 7/1902 | Burry |
| 1,164,356 A | 12/1915 | Kaiser |
| 3,658,051 A * | 4/1972 | MacLean .................... 600/14 |
| 4,095,588 A | 6/1978 | Goldman et al. |
| 4,128,824 A | 12/1978 | Mirsch |

(Continued)

OTHER PUBLICATIONS

Shupak, Therapeutic Uses of Pulsed Magnetic-Filed Exposure: A Review Dec., Radio Science Bulletin [online], Dec. 2002. Retrieved from the Internet: URL: http://www.cytotron.com/pdf/Therapeutic%20uses%20of%20pulsed%20magnetic-field%20exposure,%20a%20review.pdf> p. 1, Table 1.

(Continued)

*Primary Examiner* — Christine Matthews
*Assistant Examiner* — Joshua D Lannu
(74) *Attorney, Agent, or Firm* — Pepper Hamilton LLP

(57) ABSTRACT

A comprehensive system for inducing cellular regeneration and/or degeneration processes and methods of treatment based on such processes through generating and applying a sequentially programmed magnetic field (SPMF) to the area to be treated. In the case of regeneration and degeneration of cells, the pulsing frequencies are in the range of about 0.1 to about 2000 Hz based on the indication of the disease type which was determined by either the patient's MRI, CT, Ultrasound or other diagnostic information. Methods for treating diseases or conditions that will benefit from regeneration and/or degeneration of cells. For example, methods for treating cancer, arthritis, neuro degeneration conditions, such as the age-related progressive loss of nerve cells, Alzheimer's, Parkinson's, ALS, and Huntington's disease, retinal degeneration, and other damage to sensory systems (e.g., visual, auditory, somatosensory), in stroke, head and spinal trauma, epilepsy, in drug and alcohol abuse, in infectious diseases, in exposure to industrial and environmental toxicants, and, perhaps, in mental disorders and chronic pain. Methods for treating non-healing fractures and other bone disorders are also disclosed.

9 Claims, 40 Drawing Sheets

(56) References Cited

U.S. PATENT DOCUMENTS

| | | |
|---|---|---|
| 4,177,796 A | 12/1979 | Franco-Vila |
| 4,479,388 A | 10/1984 | Matzuk |
| 4,556,051 A | 12/1985 | Maurer |
| 5,703,735 A | 12/1997 | Bleeke |
| 6,048,302 A | 4/2000 | Markol |
| 6,234,953 B1 | 5/2001 | Thomas et al. |
| 6,647,301 B1 | 11/2003 | Sederlund et al. |
| 7,175,587 B2* | 2/2007 | Gordon et al. ............... 600/9 |
| 2002/0091850 A1 | 7/2002 | Perholtz |
| 2005/0134265 A1 | 6/2005 | Watkins et al. |
| 2005/0182287 A1* | 8/2005 | Becker .................... 600/13 |
| 2005/0198812 A1* | 9/2005 | Schuster et al. ........... 29/606 |
| 2005/0228209 A1* | 10/2005 | Schneider et al. ........ 600/13 |
| 2005/0259373 A1 | 11/2005 | Hoopes |
| 2006/0245217 A1 | 11/2006 | Kirbie et al. |
| 2007/0014055 A1 | 1/2007 | Ness |
| 2007/0027355 A1* | 2/2007 | Riehl et al. ................ 600/13 |
| 2007/0030176 A1 | 2/2007 | Sanchez-Olea et al. |
| 2007/0208249 A1* | 9/2007 | Kumar .................... 600/410 |
| 2008/0097142 A1 | 4/2008 | Savage |

OTHER PUBLICATIONS

Hovey et al., "The Guide to Magnetic Stimulation," Jul. 21, 2006. Retrieved from the Internet: <URL: http://www.icts.uci.edu/neuroimaging/GuidetoMagneticStimulation2008.pdf.
International Search Report dated Feb. 28, 2011.

\* cited by examiner

FIG. 1 is a schematic of the section of magnetic field generating device

Front View

Top View

FIG. 2 is a schematic of the ferrite rod
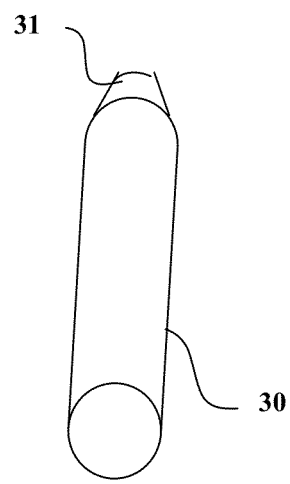

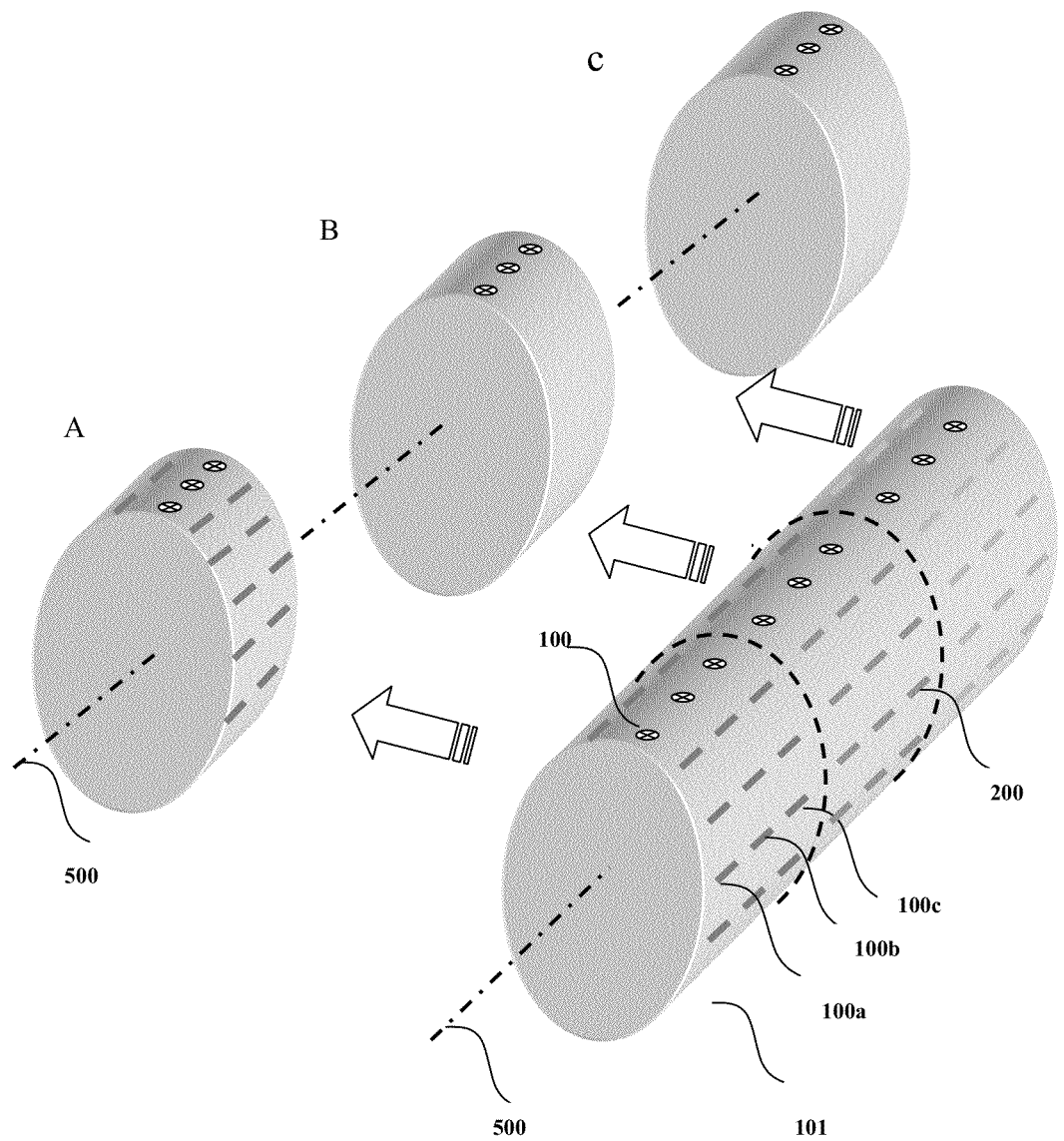
Figure 7 Layout of the MFG devices

Figure 8 Layout of the MFG devices
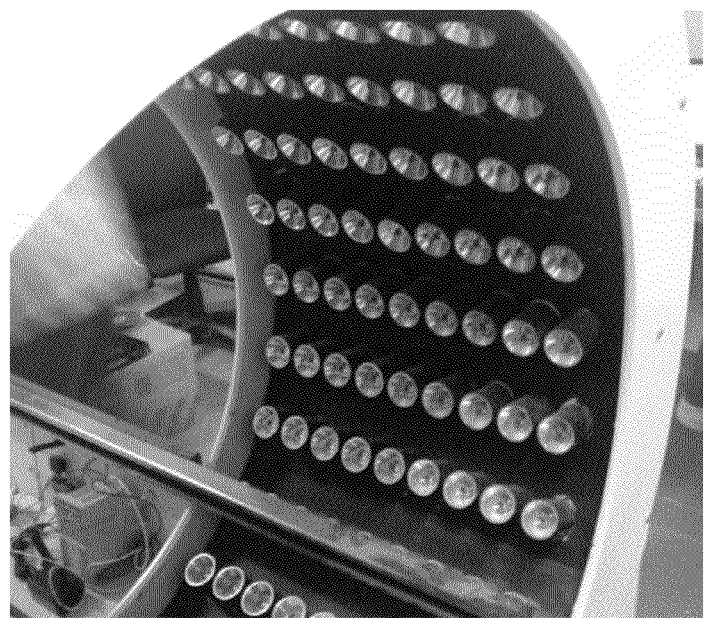

FIG. 9A CT, 20/07/09

FIG. 9B Pre SPMF CT-19/09/2009

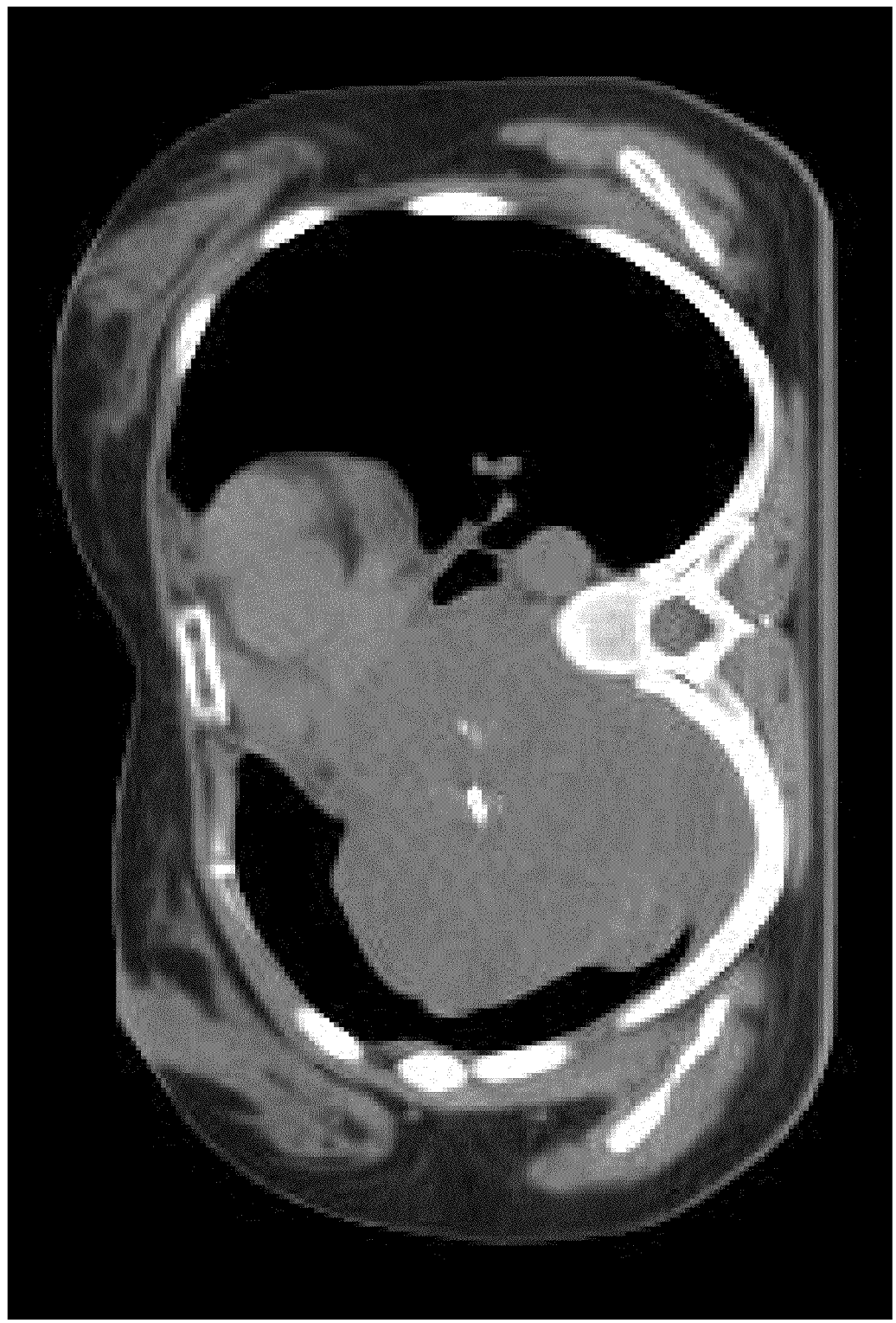
FIG. 9C Mid SPMF, CT- 07/10/2009

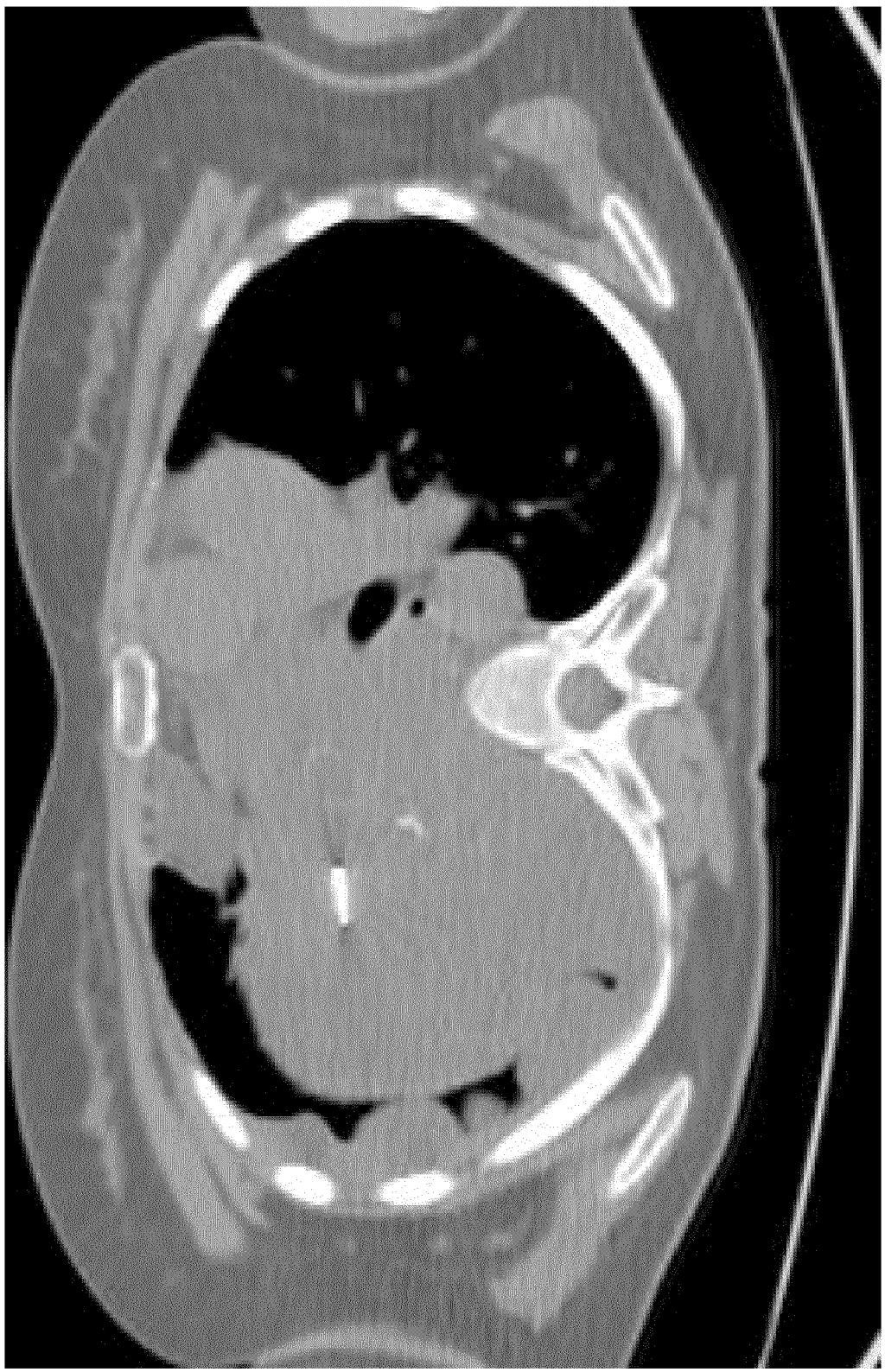
FIG. 9D PET CT WHOLE BODY -29/10/09

FIG. 9E CT SCAN 05-11-09

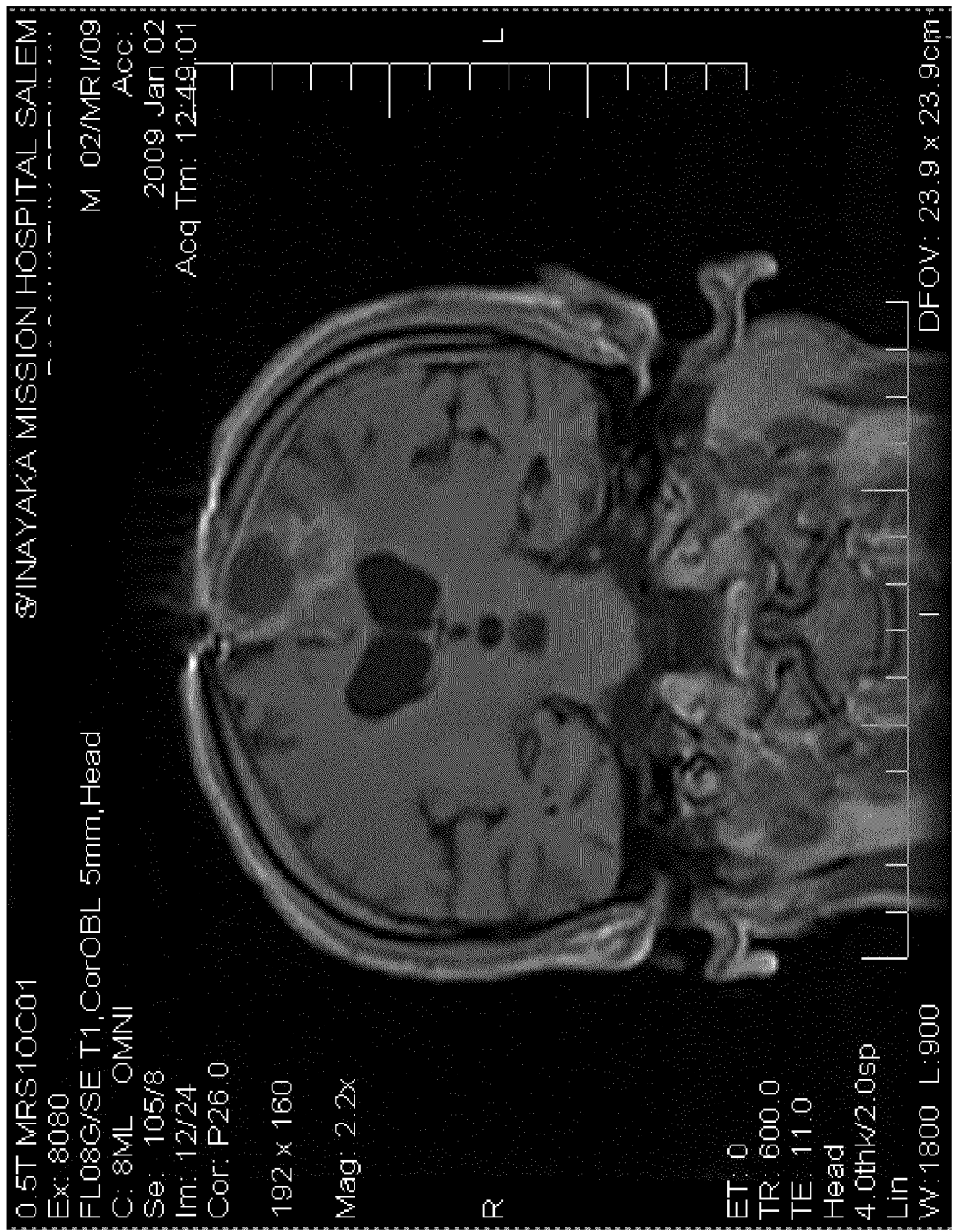
FIG. 10A Pre SPMF MRI : lesion size 2.2 x 3.8 Cms.

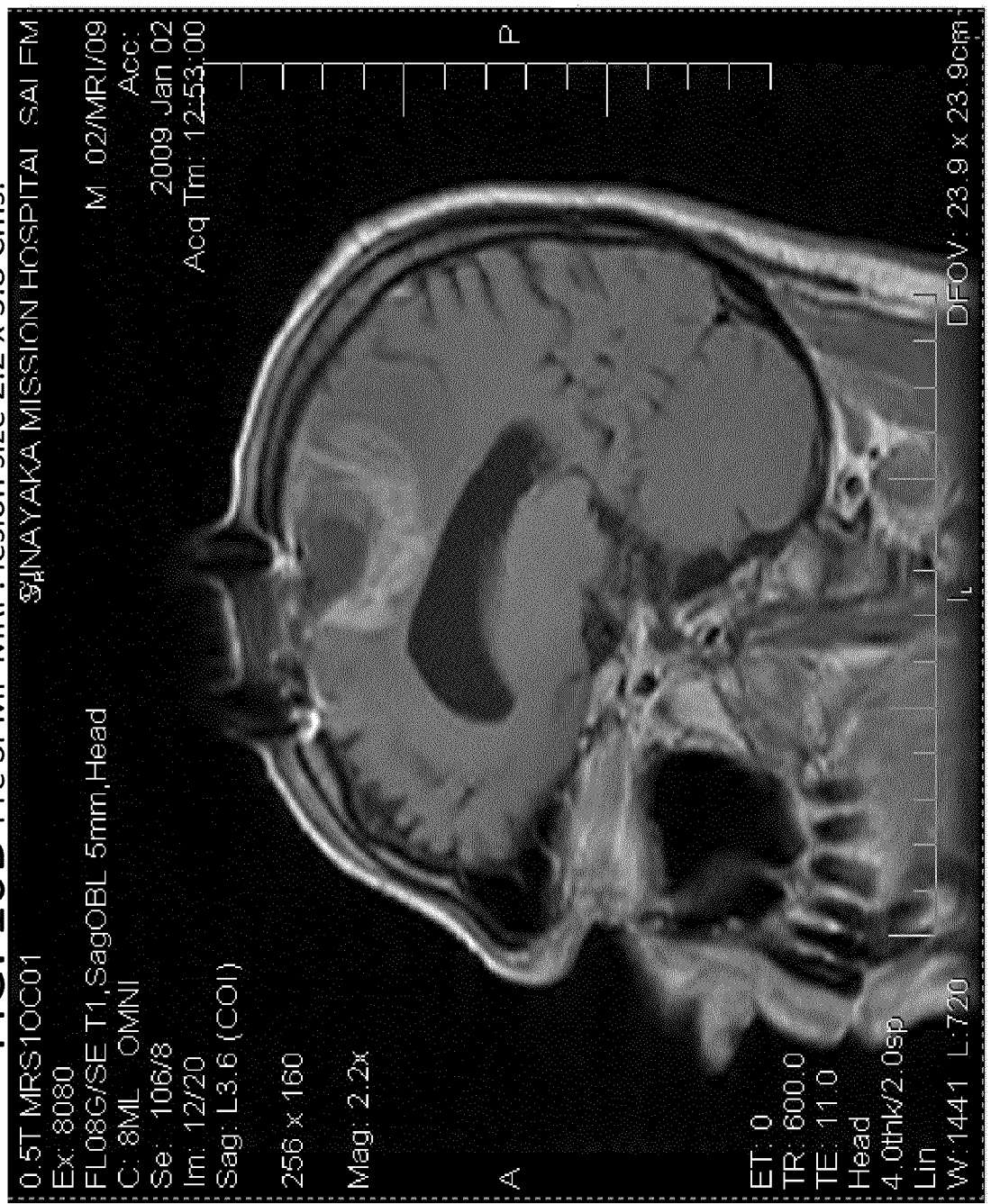
FIG. 10B Pre SPMF MRI: lesion size 2.2 x 3.8 Cms.

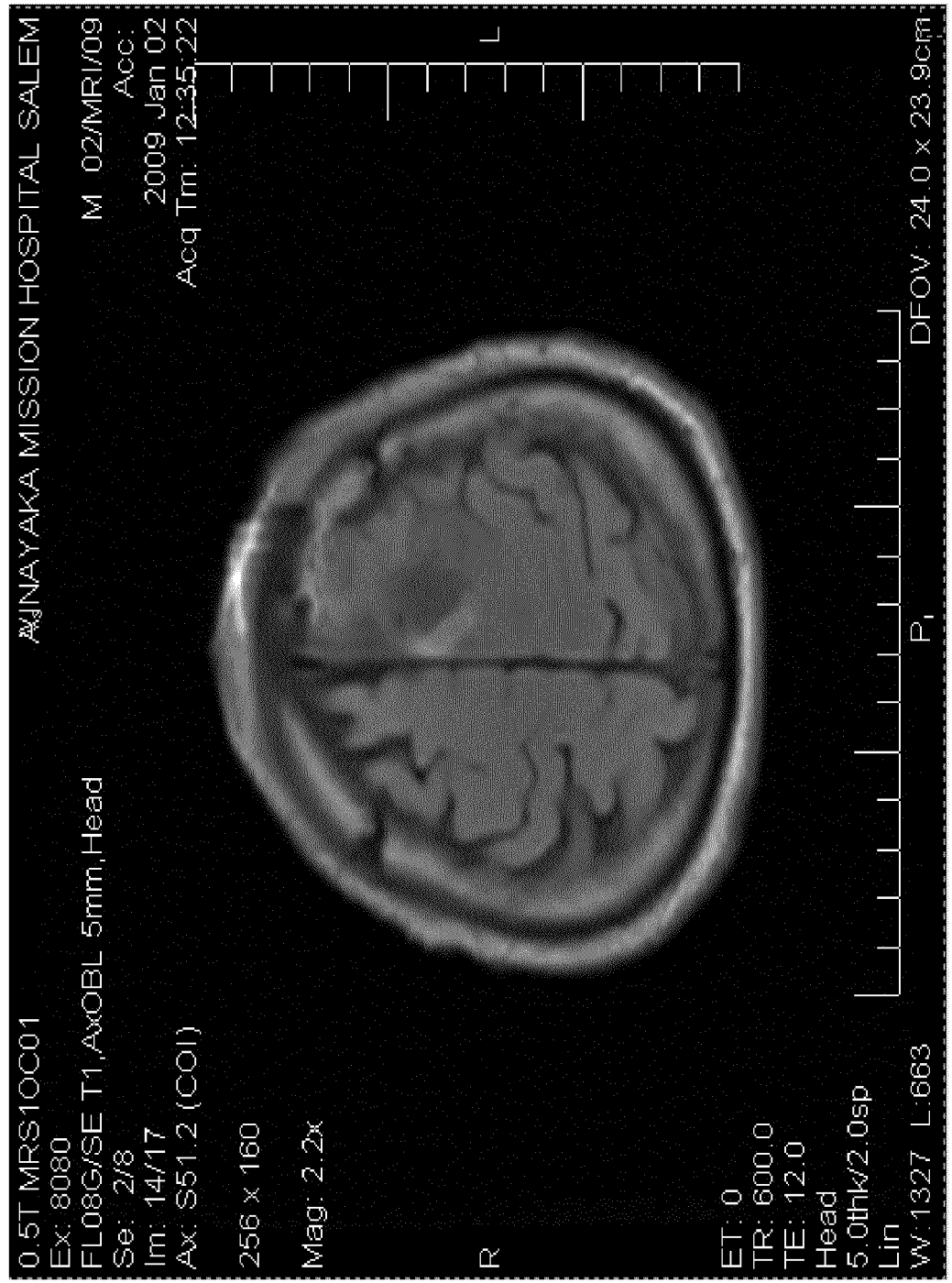
FIG. 10C Pre SPMF MRI : lesion size 2.2 x 3.8 Cms.

FIG. 10D Immediate Post SPMF : Lesion size 2.0 x 3.5 Cms.

FIG. 10E Immediate Post SPMF : Lesion size 2.0 x 3.5 Cms.

FIG. 10F Immediate Post SPMF : Lesion size 2.0 x 3.5 Cms.

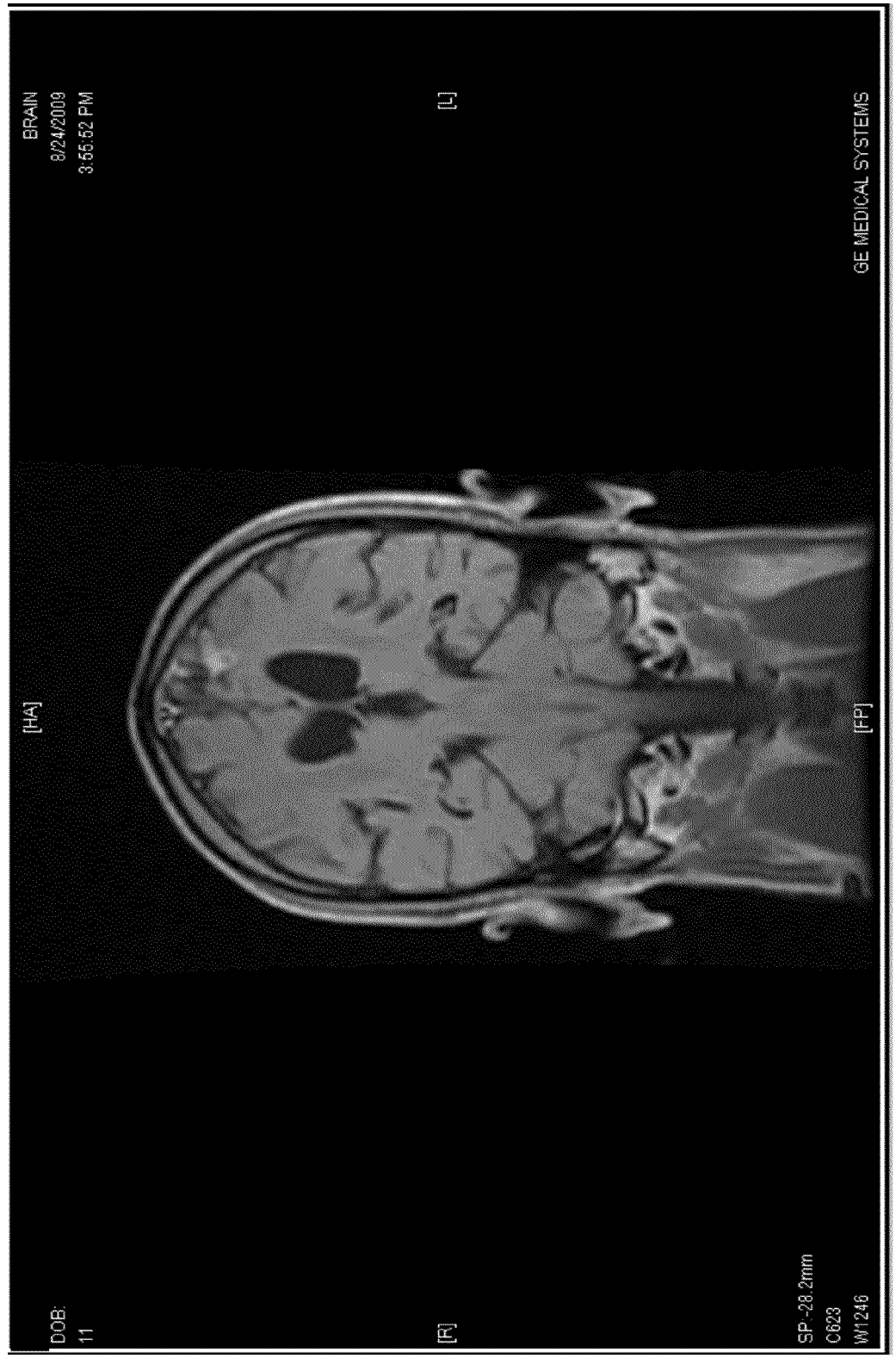
FIG. 10G Post SPMF 04 months: lesion size 1.4 x 1.5 Cms.

FIG. 10H Post SPMF 04 months: lesion size 1.4 x 1.5 Cms.

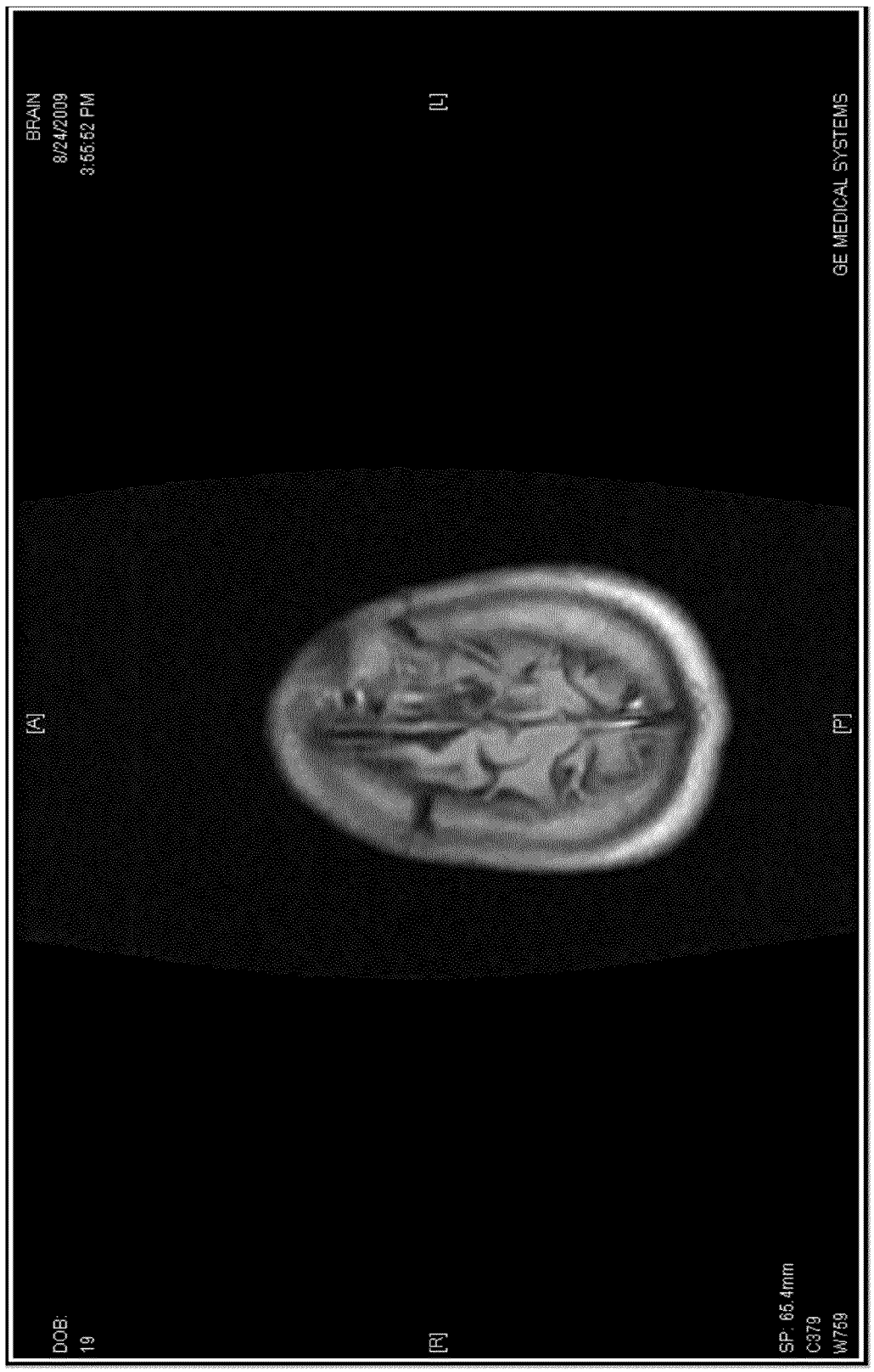
FIG. 10I Post SPMF 04 months: lesion size 1.4 x 1.5 Cms.

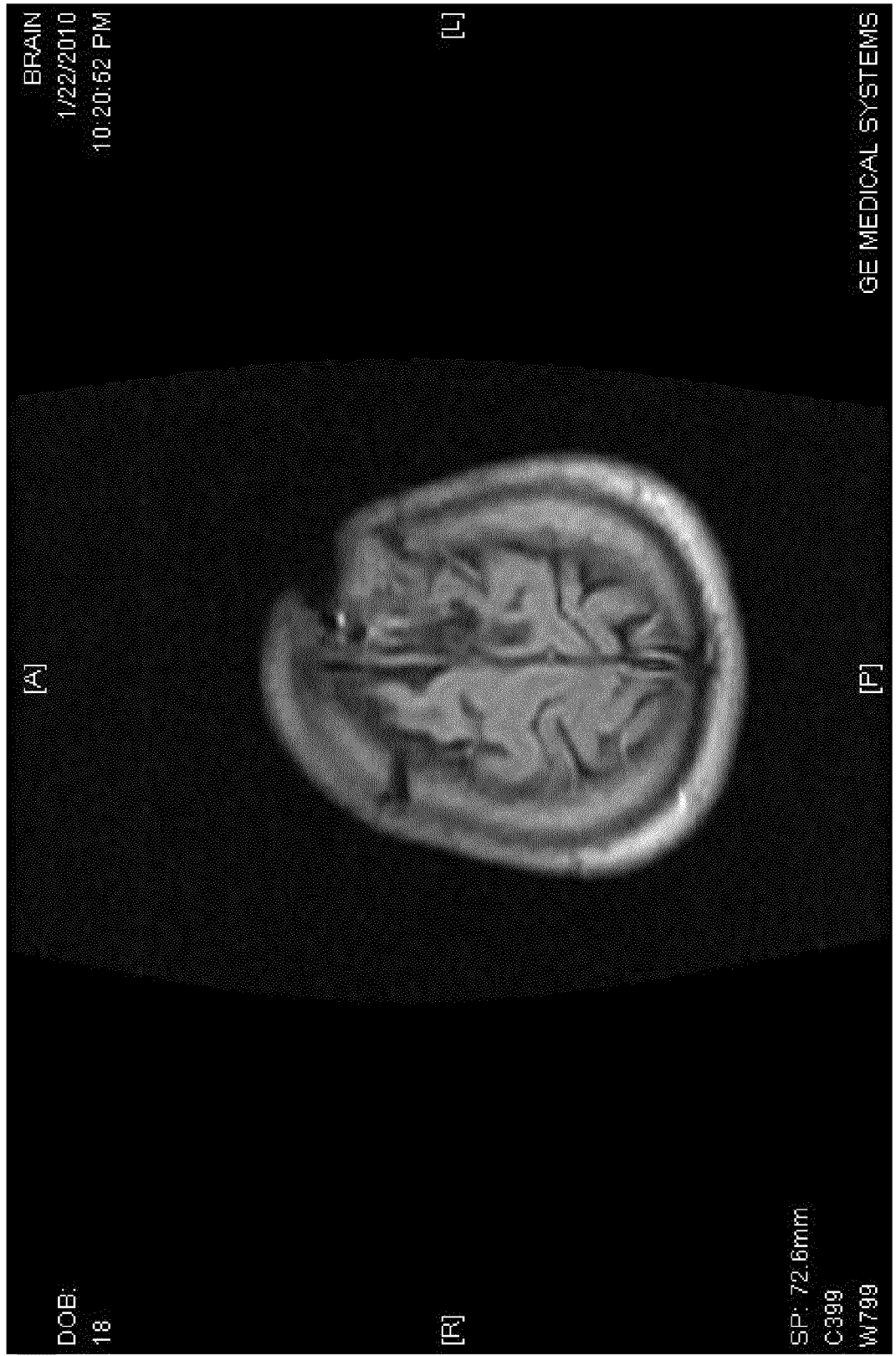
FIG. 10J Post SPMF – 9 months, Dated 22-01-2010

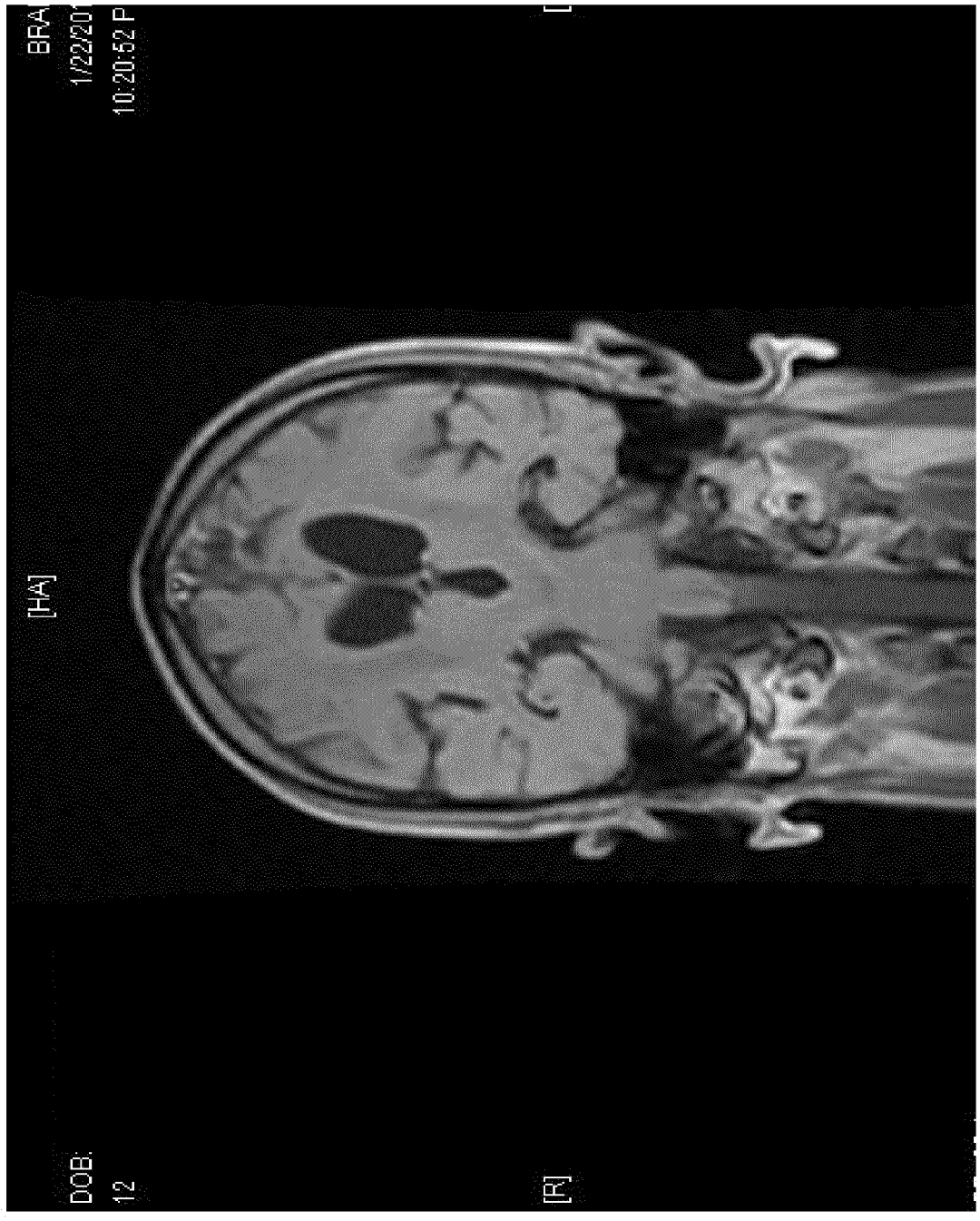
FIG. 10K Post SPMF – 9 months, Dated 22-01-2010

FIG. 10L Post SPMF – 9 months, Dated 22-01-2010

Progress Report for SPMF Therapy

Progress Report for
SPMF Therapy

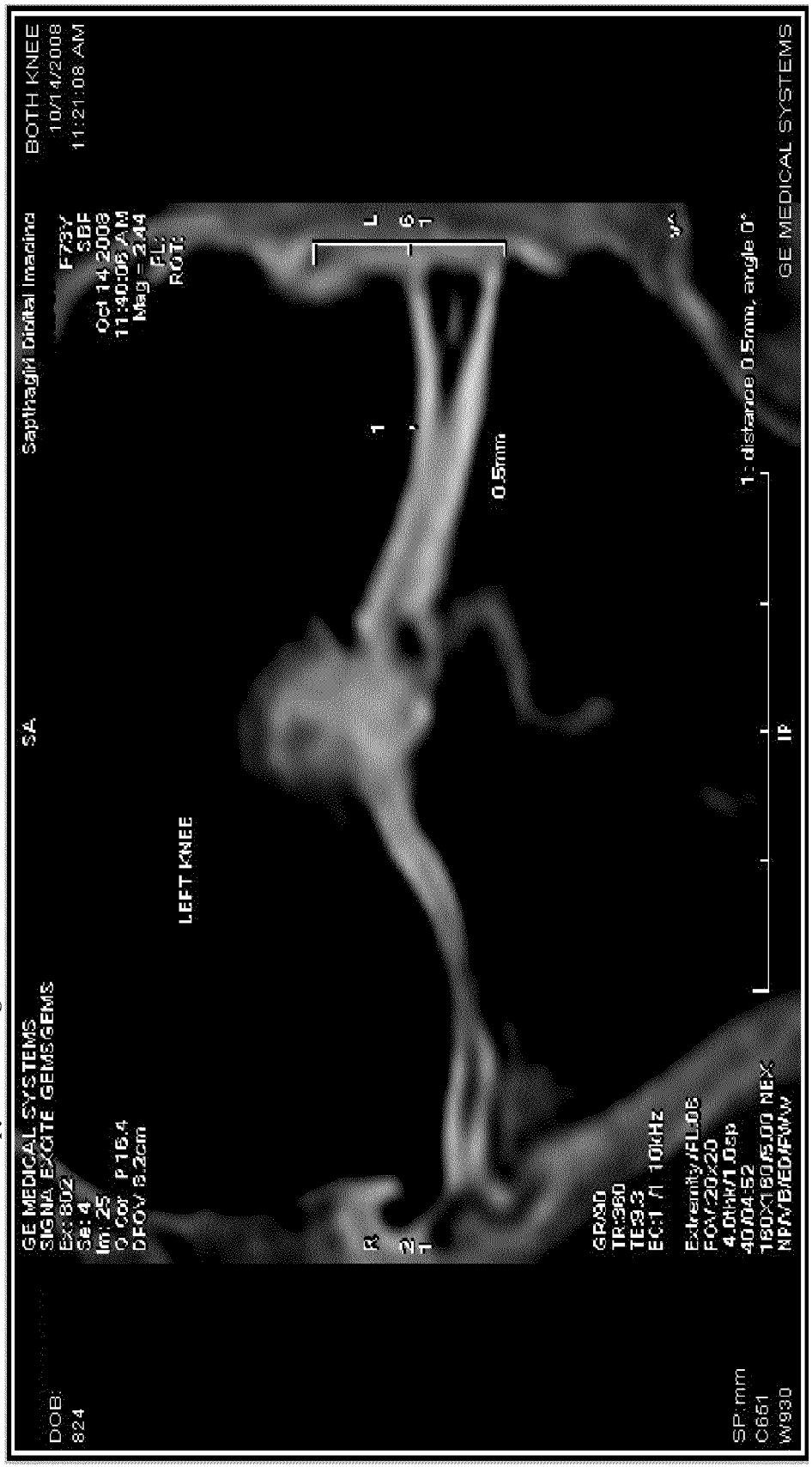
FIG. 11B Pre SPMF Therapy MRI Images

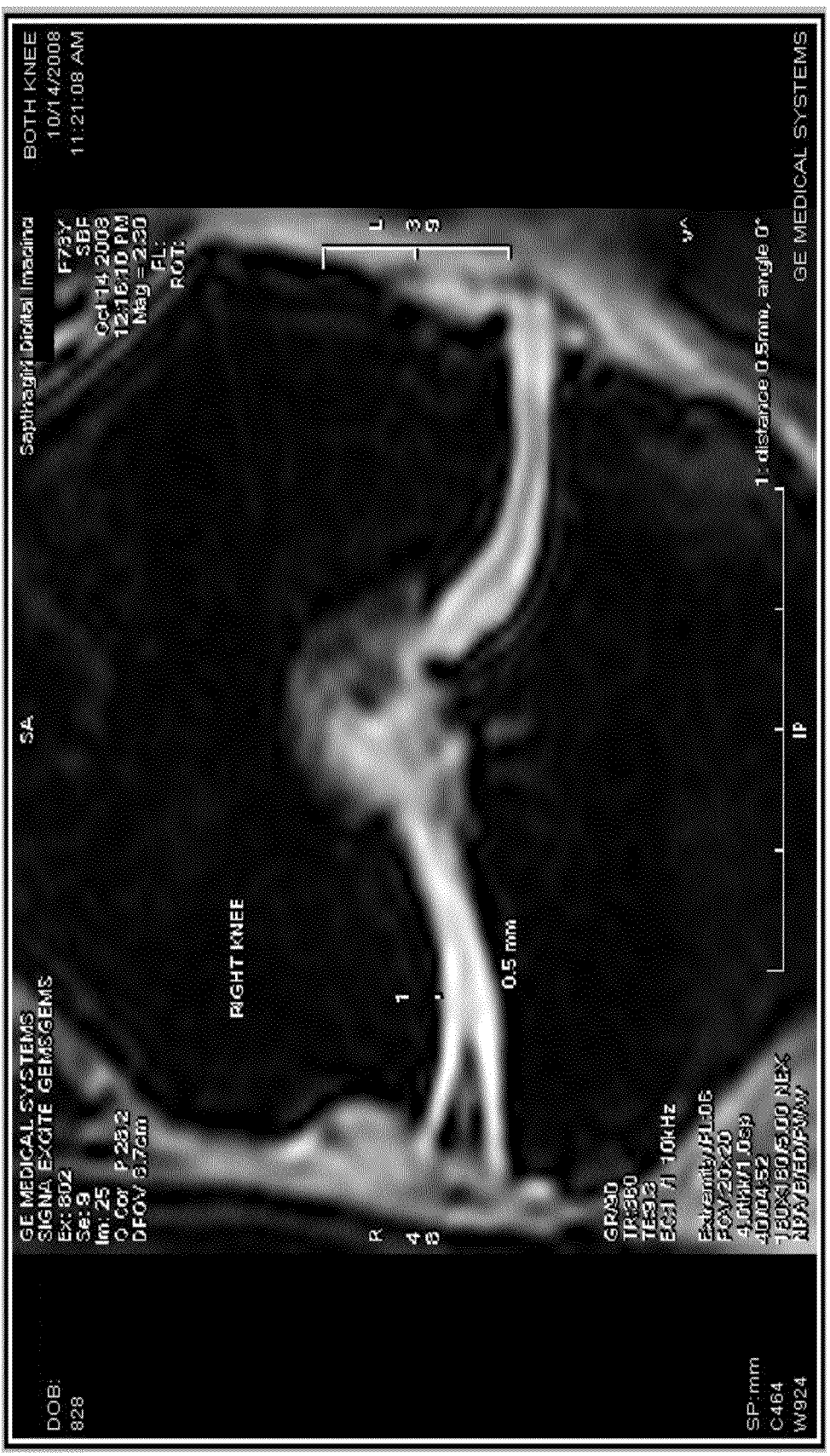
FIG. 11C Pre SPMF Therapy MRI Images

FIG. 11D Post SPMF Therapy MRI Images

FIG. 12 ; Pictorial representation of a human cell and organelles
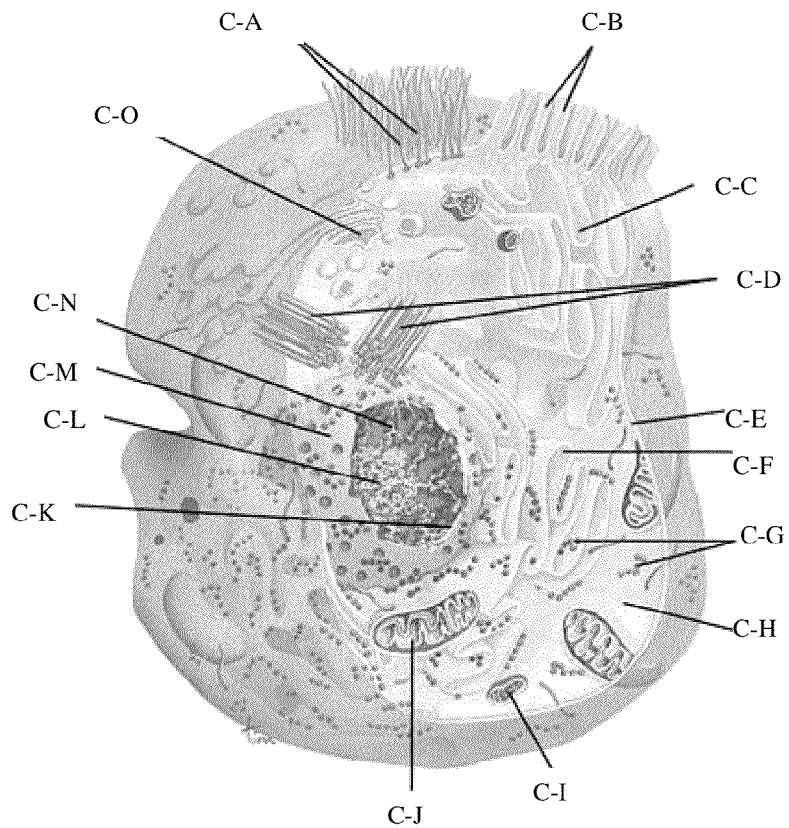
FIG. 13
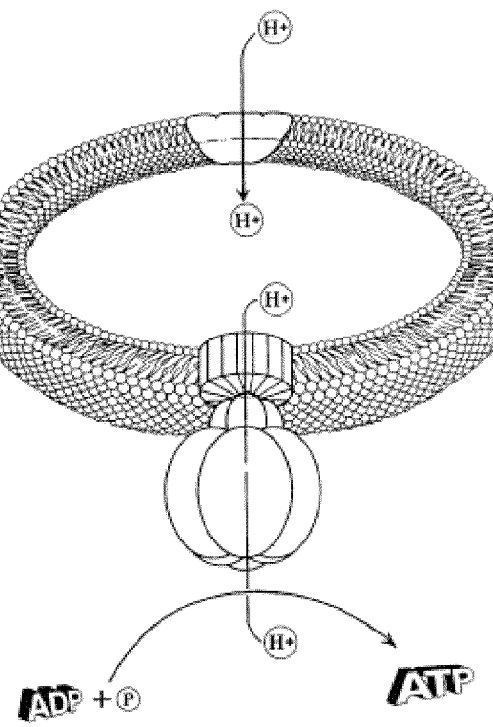

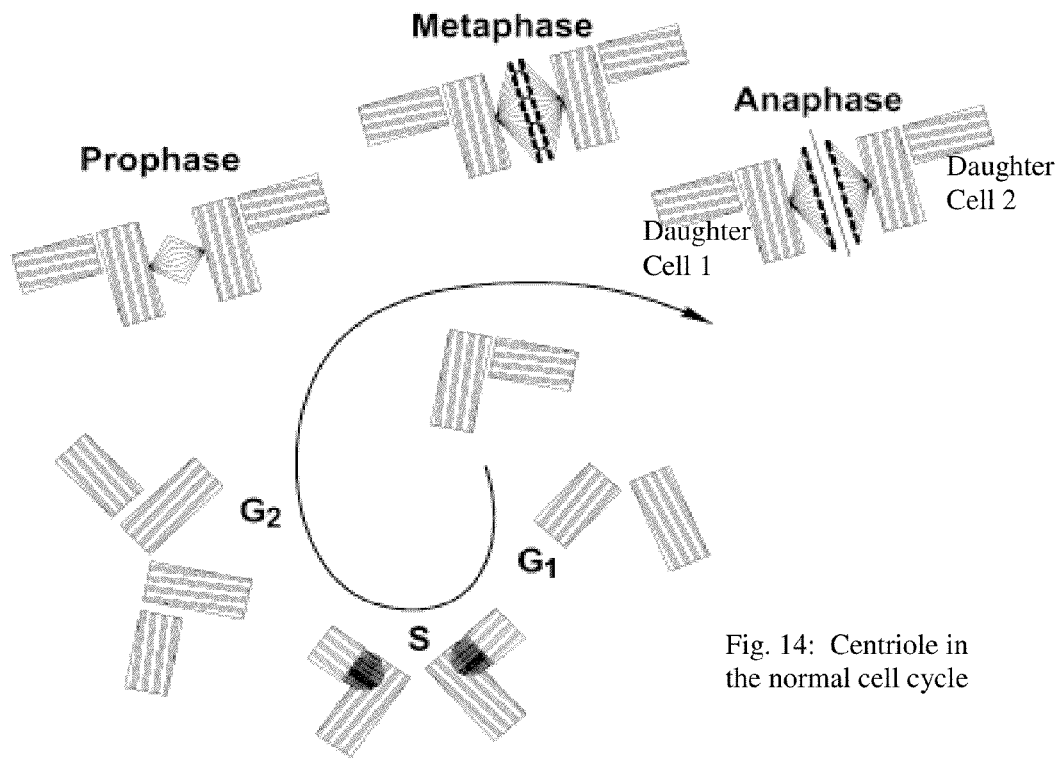
Fig. 14: Centriole in the normal cell cycle
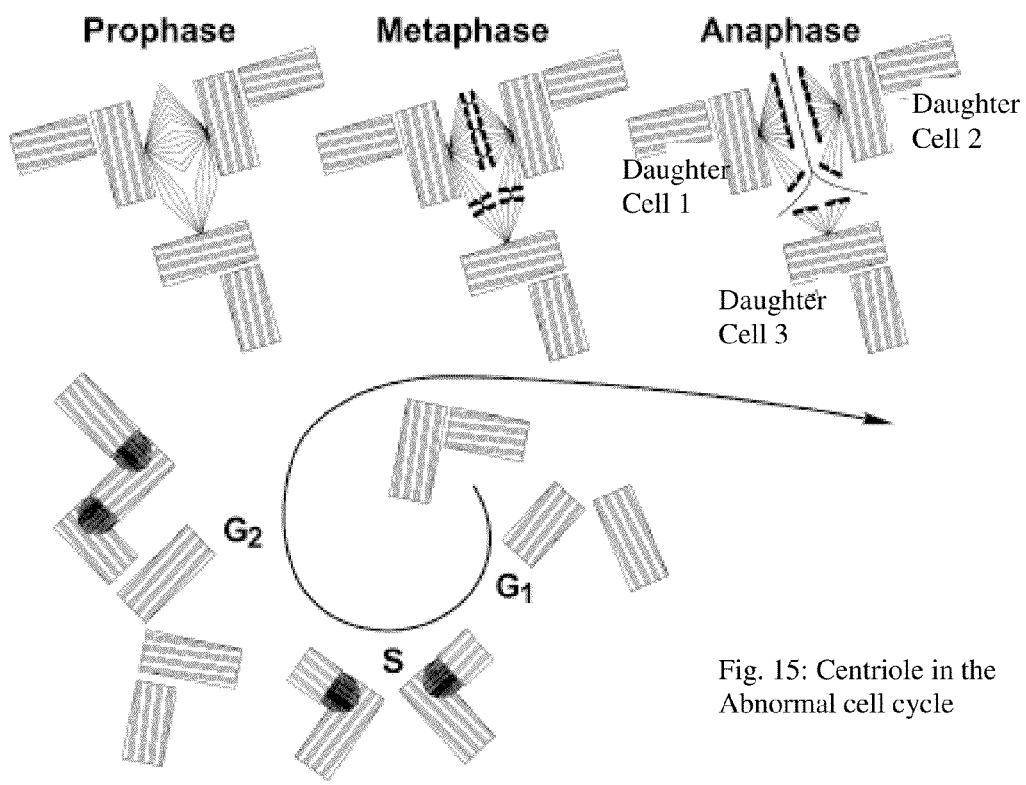
Fig. 15: Centriole in the Abnormal cell cycle FIG. 16A ; flow chart for patient treatment (cancer)
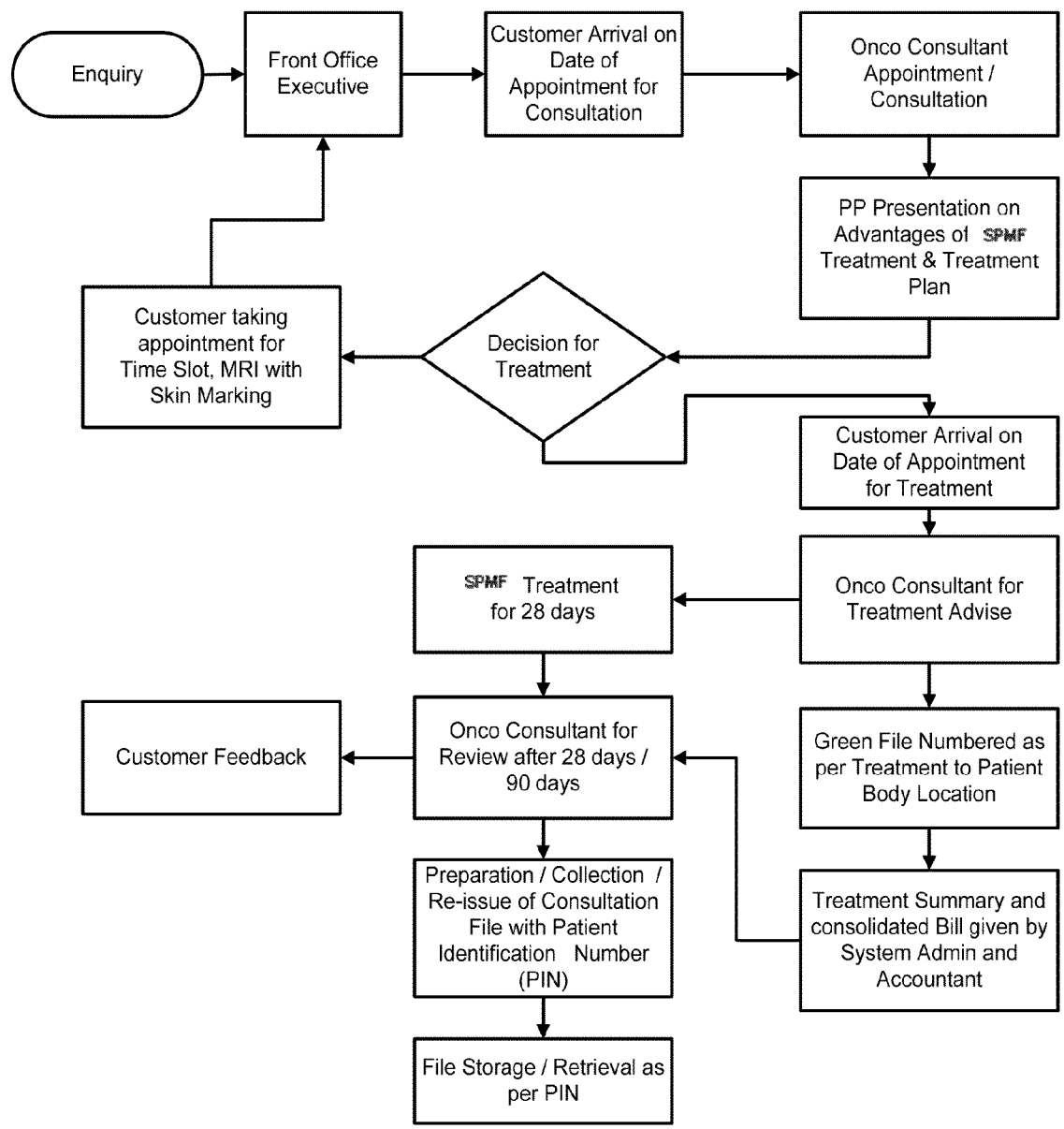

FLOW CHART ON MECHANISM OF ACTION OF SPMF IN DEGENERATION

FIG. 17A ; flow chart for patient treatment (arthritis)
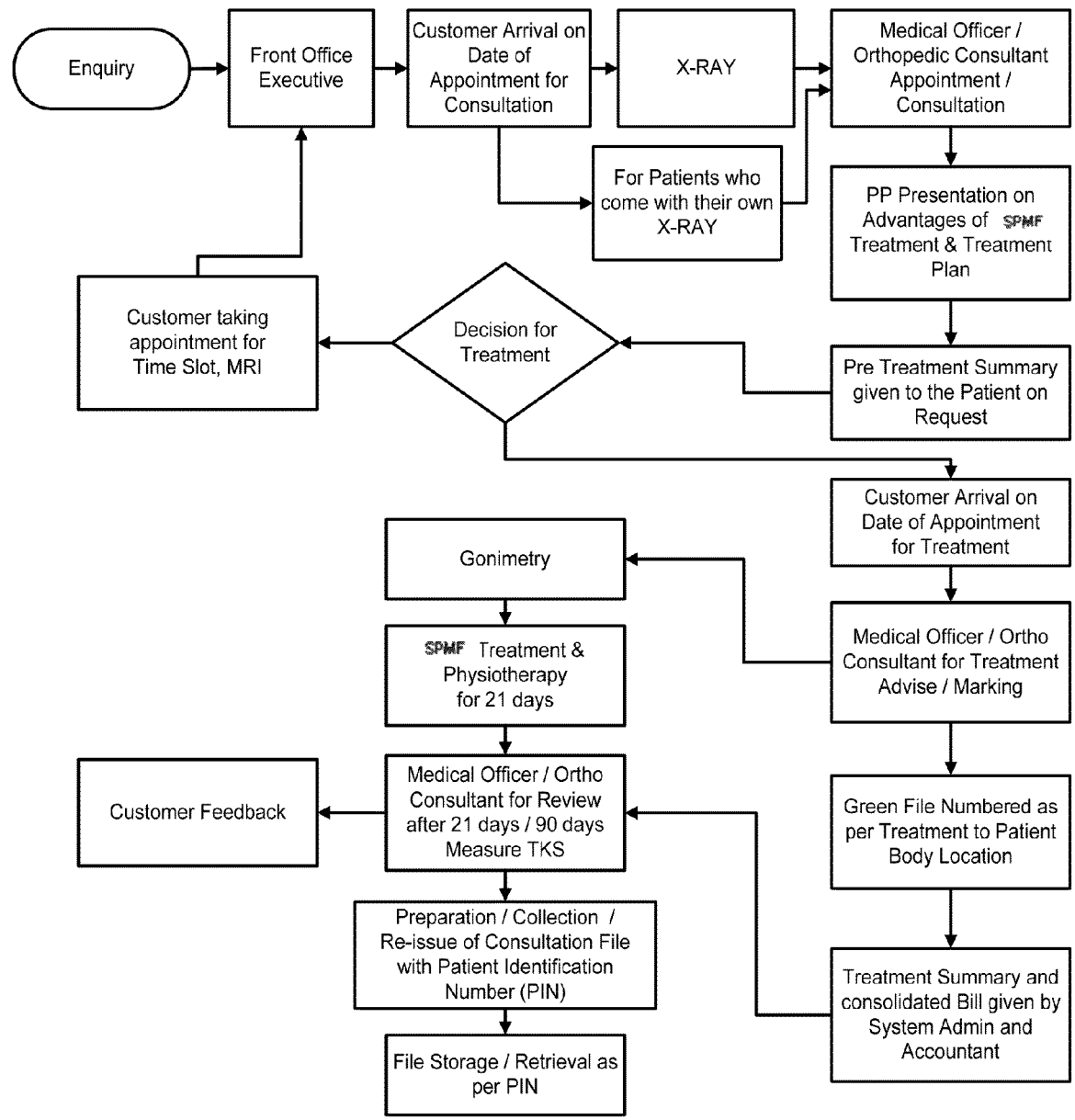

FLOW CHART ON MECHANISM OF ACTION OF SPMF IN REGENERATION

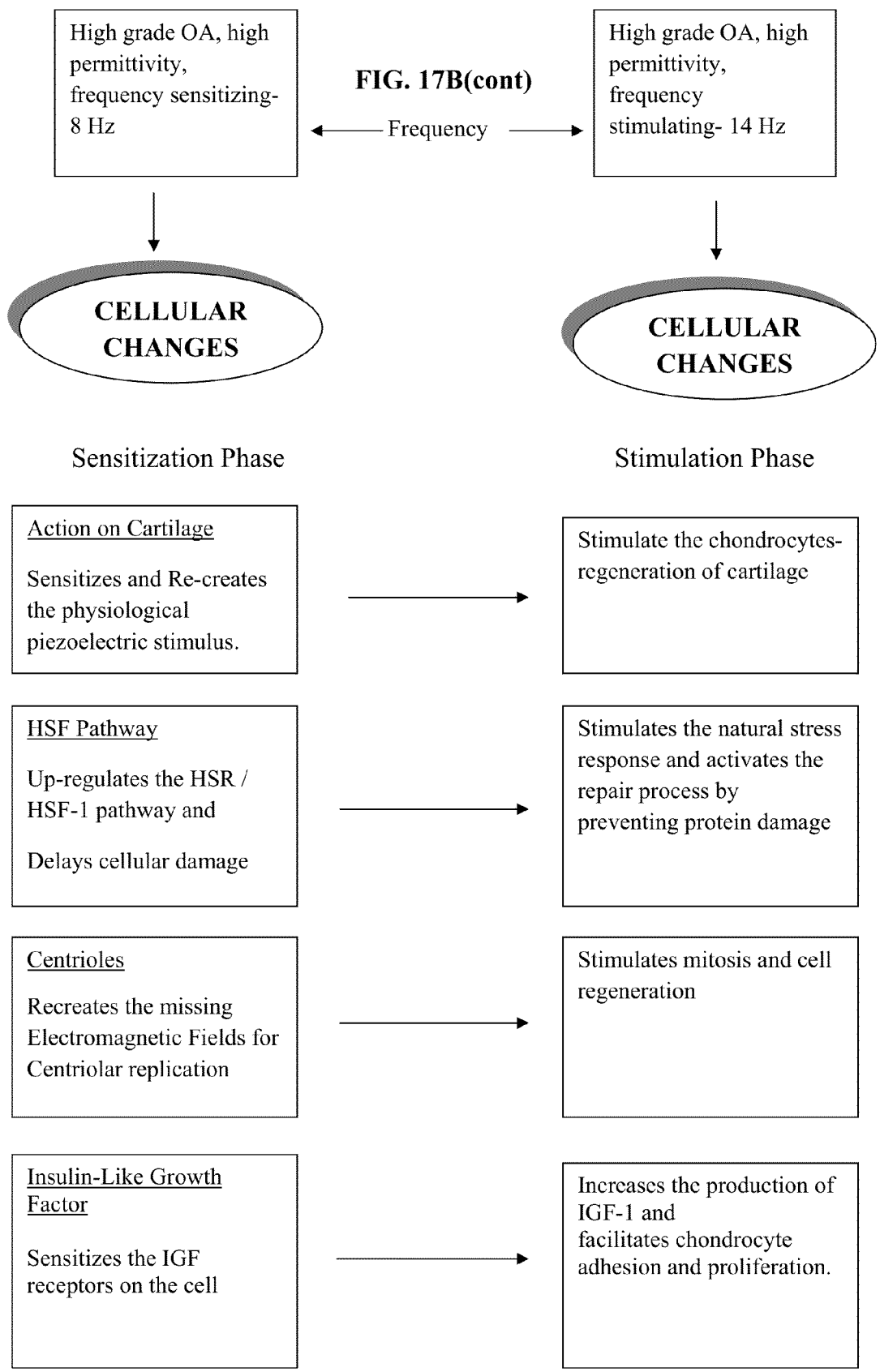

FIG. 18 ; flow chart for patient treatment (neuro-tinnitus)
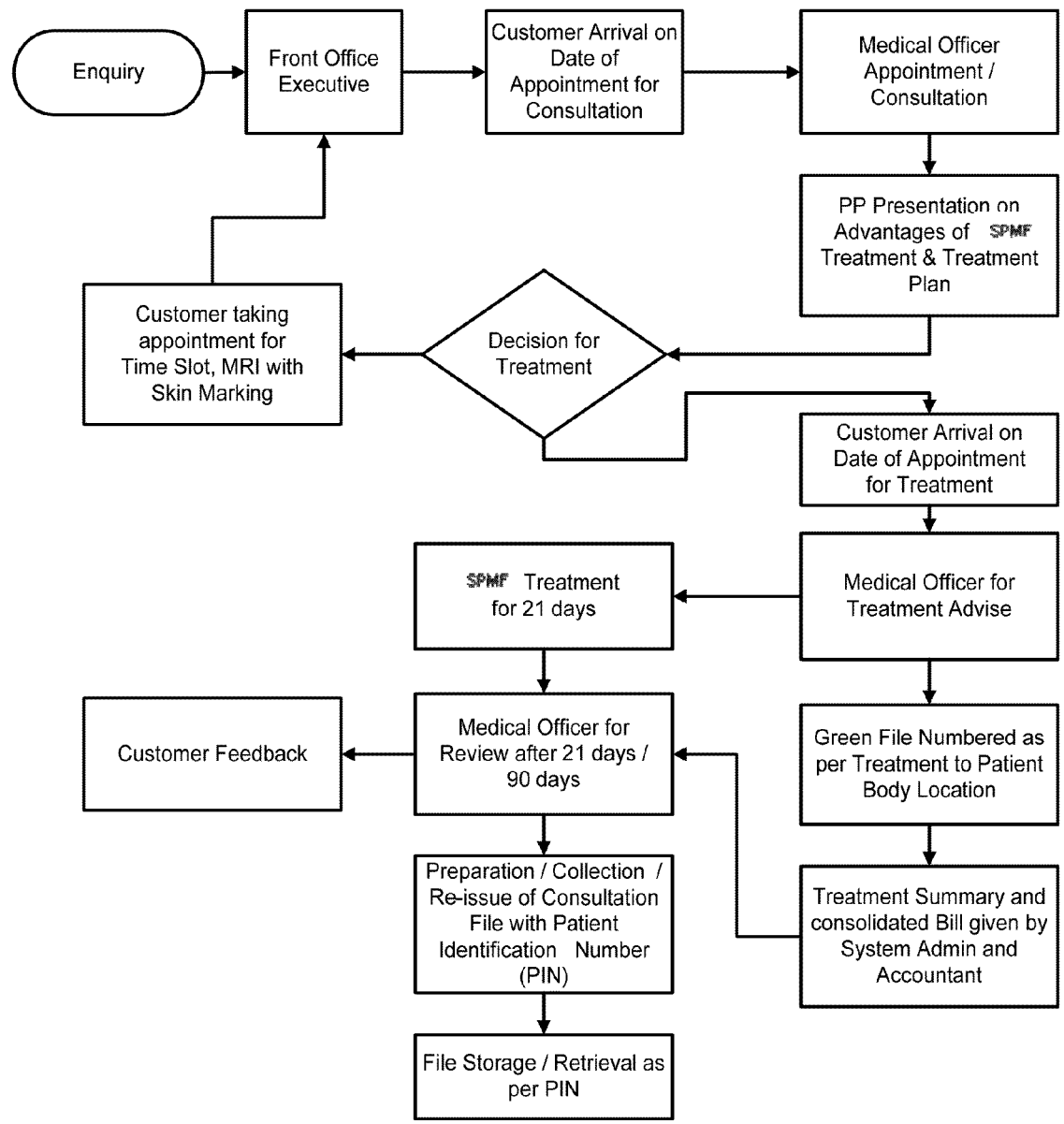

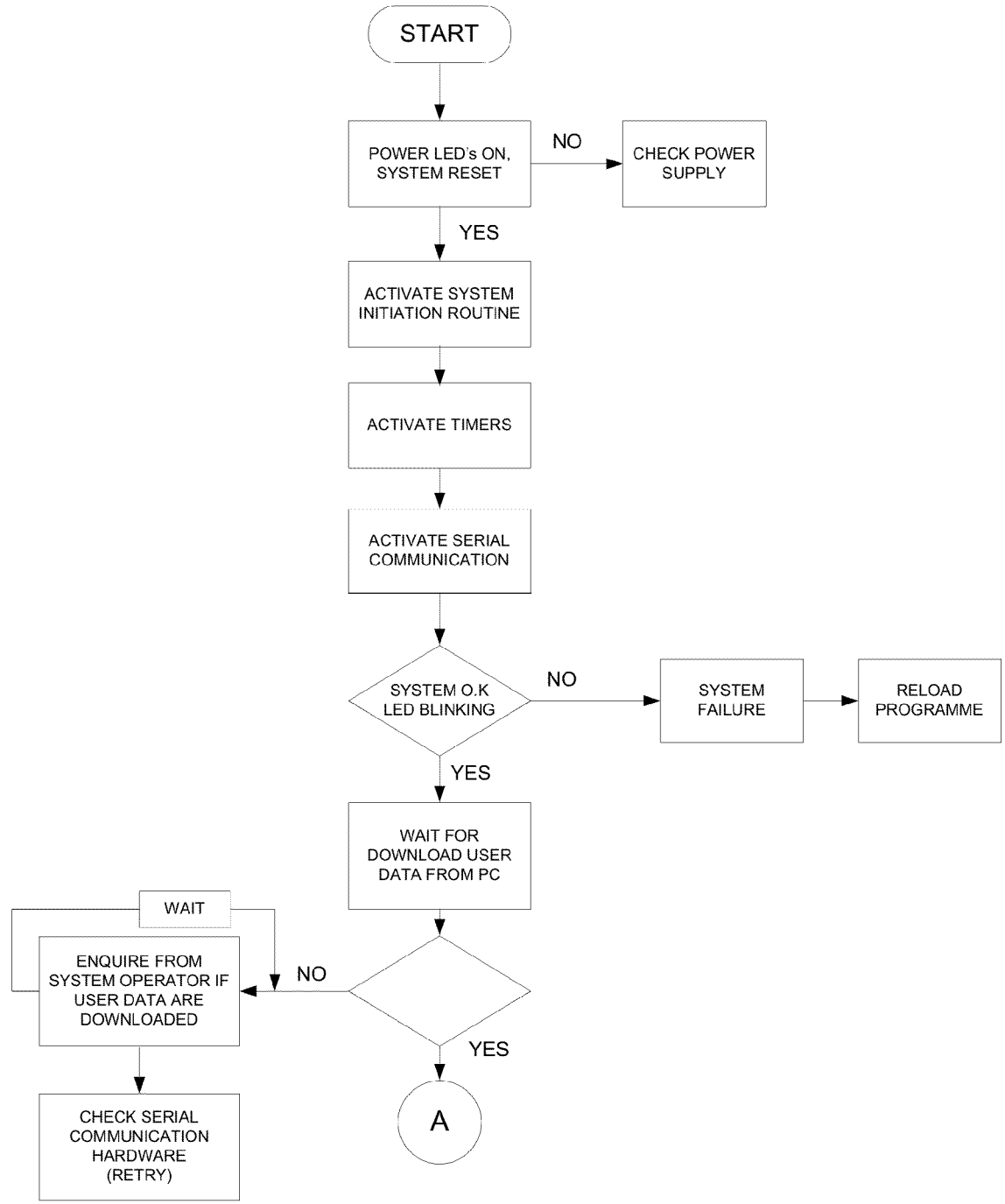
FIG. 19 SPMF system flowchart

SEQUENTIALLY PROGRAMMED MAGNETIC FIELD THERAPEUTIC SYSTEM (SPMF)

This application claims priority to Indian Provisional Specification no. 184/MUM/2009, entitled AN APPARATUS FOR INDUCING MAGNETIC RESONANCE IN BIOLOGICAL TISSUES, filed on Jan. 30, 2009 and to U.S. Provisional Patent Application Ser. No. 61/285,712, entitled SEQUENTIALLY PROGRAMMED MAGNETIC FIELD THERAPEUTIC SYSTEM (SPMF), filed on Dec. 11, 2009. The entire content of each application is hereby incorporated by reference for any purpose.

TECHNOLOGY FIELD

The invention relates to systems for generating and inducing sequentially programmed magnetic fields (SPMFs) in biological tissue(s) and methods for inducing cellular regeneration and/or degeneration processes and methods of treatment based on such processes using such a system. More particularly, the invention relates to a SPMF therapeutic system and method for the regeneration or degeneration of biological tissue(s). More particularly, it relates to an apparatus or system for generating and applying SPMFs to biological tissue(s) which resonates therein.

BACKGROUND

It is known that electromagnetic fields of certain frequency ranges and intensities are indigenous to living tissues and it has been found that inciting the inherent resonance by exogenous treatment using electromagnetic fields [EMF], electric fields, and magnetic fields can induce cellular regeneration and degeneration processes. EMF in a range from 0.1-150 Hz have been reported to stimulate bone cells. It has also been reported that bone resorption that normally parallels disuse can be prevented or even reversed by the exogenous induction of electric fields. Electromagnetic fields below 10 microV/cm, when induced at frequencies between 50 and 150 Hz for 1 h/day, are sufficient to maintain bone mass even in the absence of function. Reducing the frequency to 15 Hz makes the field extremely osteogenic. This frequency-specific sinusoidal field initiated more new bone formation than a more complex pulsed electromagnetic field (PEMF), though inducing only 0.1% of the electrical energy of the PEMF.

In Yuri Gagarin's historic flight into space, he returned in near critical condition after only one hour and forty eight minutes in space. Clearly there was some vital element missing in space that we receive on earth. Yuri had plenty of food, water, and oxygen and since the flight was less than 2 hours he really only needed oxygen. The critical missing element appears to be PEMF—Pulsed Electromagnetic Fields. Since that first flight, pulsed magnetic devices have been used in every space suit and space station. Further studies have been done on earth (zero field studies) with both laboratory animals and human subjects. In a matter of hours without exposure to healthy PEMF's, cell metabolism begins to break down causing bone loss, muscle weakness, depressed metabolism, disorientation and depression.

A range of PEMF machines have been introduced in the market. PEMF therapy has been reported to decrease pain, improve sleep, enhance circulation, regenerate nerves, help in healing of wounds, enhance immunity and improve bone density.

An area of immense interest has been the use of magnetic stimulation in rehabilitating injured or paralyzed muscle groups. Magnetic stimulation of the heart has been considered to be superior to CPR or electrical stimulation, because both of those methods apply gross stimulation to the entire heart all at once. A magnetic stimulator can be used as an external pacer to stimulate each chamber of the heart separately in the proper sequence. Another area in which magnetic stimulation is proving effective is treatment of the spine. The spinal cord is difficult to access directly because vertebrae surround it. Magnetic stimulation may be used to block the transmission of pain via nerves in the back, e.g., those responsible for lower back pain. Magnetic stimulation also has proven effective in stimulating regions of the brain thereby providing a number of treatment options including several classes of anti-depressant medications (Sari's, MAI's and tricyclics), lithium, and electroconvulsive therapy (ECT). Recently, repetitive transcranial magnetic stimulation (rTMS) has also been shown to have significant anti-depressant effects for patients that do not respond to the traditional methods. The membranes are depolarized by the induction of small electric fields in excess of 1 V/cm that are the result of a rapidly changing magnetic field applied non-invasively.

The use of electromagnetic fields (EMFs) for healing has been known from time immemorial. Even many centuries back, simple magnets were used for regenerative purposes. It is only in the last 50 years that specific use of electromagnetic fields has been clearly defined to aid in or facilitate biological tissue regeneration or degeneration. Much research has gone into this use of electromagnetic fields. In the last 50 years research has established a scientific basis for use of electromagnetic devices in the treatment of illness, although many applications have yet to be specific enough to achieve the desired changes.

Each tissue in the body is made of cells and a cell is the smallest distinct entity of that particular type of tissue. The cell has a specific cell membrane and the cell membrane is a dividing structure that maintains biochemically distinct compartments between the inside and outside of the cell. The inside is the intracellular compartment and the outside is the extracellular space, as described by Marieb in 1998. In order to maintain a balance there is a free exchange of electrolytes, water, sodium and potassium constantly through the intracellular and extracellular compartments. The passage of these electrically charged ions will create flow of electrical currents through the membrane. These ions in turn affect the metabolism of the cell and potential of the cell membrane. The normal cell membrane potential is about −70 to −90 mV. A lot of research has been done on how cell membrane potential is the key to maintain cell activity and the behavior of the cell itself. Clarence Cone et. al. from 1970 was responsible for publication of majority of scientific papers on this entity. The lipid structure of the cell membrane makes it relatively impermeable to the transfer of the ions and therefore, these ions pass through ion channels. The ions channels contain aqueous pores that connect the inside of the cell to the extracellular space. These are open and shut based on a variety of signals. Dr. Steve Haltiwanger has described in his thesis on the use of electrotherapy for diseases on how to build up of different concentration of mineral ions and endow cell membrane with electrical property of capacitance. Capacitors are well known electrical components that are composed of two conducting sheets of metal plates separated by thin layer of insulating material. The membrane of the cell organelle that have mitochondria in animals and the chloroplast in plants act as biological capacitors and they have the capacity to accumulate and store charge and hence energy can be given up when needed. A cell or a human body is coupled to its electric field in proportion to its capacitance such that the greater the frequency of the electric field, the greater the current flow of the cell for the body. For soft tissue low frequency natural or applied electric field current will create current that are conducted primarily along the surface of the cell. This has been described by Adey et. al. in 1993. When high frequency fields are applied with external signal generators such as micro current devices, magnetic pulses or the plasma tubes or Rife devices, electrical charging of the cell membrane occurs causing an increase in cell membrane capacitance and increased conduction of current through the cell membrane. This is distinctly described by Haltiwanger also in 2003. This means that the devices that generate low frequency current will have different biological effects and the device that generates high frequency can have different biological effect. In summary, increase in cell membrane capacitances would change cell membrane permeability and could cause significant changes in cell behavior.

Scientific research has proven that cells are electro magnetic in nature and they generate their own electro magnetic fields and are also capable of harnessing external electro magnetic energy in the right wave length and strength to communicate control and drive metabolic functions as described by Adey in 1988 and 1993 as also by Becker in 1990. The application of a varying magnetic flux to the area of the body will induce an electric field along the perimeters of the area. This is according to the basic laws of electromagnetism. When varying magnetic fields are applied to human tissues that contain free or charged carriers these charge carriers are accelerated by the electric field thereby generating eddy currents. The induced electric field or the generated current depends on the rate of change of the magnetic field. Time varying magnetic fields that induce cellgrowth acceleration, enzyme activation and changes in membrane in metabolism have been described earlier by Enforte in 1990. It is well recognized that electrical currents and magnetic fields are continuously produced in the body at all times. For example in the ECG—the Cardiologist measure the electrical currents of the beating heart or in the EEG—the Neurologist measure the electrical activity of the brain, or in the EMG—the Neurologist measure the activity of the muscle and the nerve. Likewise whole lot of other parameters that are related to this can be measured. Electricity in the body comes from the food that we eat and the air that we breathe. Lester Brown in 1999 described energy from enzyme catalysed chemical reaction which involves oxidation of fats, proteins and carbohydrates. Cells can produce energy by oxidation, dependent aerobic enzyme particles and by less efficient fermentation process.

In regeneration, in normal people, for example, when weight is put on the knees, the cartilage gets compressed and this itself is the stimulus for the regeneration to start and there is forced efflux of hydrogen protons causing changes in the cell membrane potential. This capacity is lost in the osteoarthritic patient. However, by selectively altering this cell membrane potential by use of time varying electromagnetic fields which are tuned to this specific resonating frequency one can re-induce this change into the cell at rest.

The use of electromagnetic fields in cancer therapy has been fairly summarized by Marc Neveu PhD in his recent article on Explore Volume 12 Nov. 4, 2003 wherein he has likened the DNA to act as the computer's binary code that runs various programs and the nucleus to the hard disk. Imagine the DNA mutations in cancer cells are like software problems or like virus in system conflicts. An increase of software errors like mutations increase chaos in the system and slows down the computer's overall performance. Actually cancer cells have many mutations in the DNA sequence that regulate the cell growth and can get stuck being on mode. As an example we can try to debug the program or the other way to get the computer work again is to reboot. So electromagnetic therapy using electromagnetic waves having very specific frequency to retune to cellular programs can restore this programs and restore optimal cell operation. Normal cells restart following magnetic resonance therapy without a problem because their DNA that is software normal. However cancer cells try to reboot, the multiple defect in the DNA as the mutation, chromosome aberrations and viruses prevent restart which would cause tumor cells to stop growing or start the induction of the pro-apoptotic cycle and go into apoptosis. The frequency is essentially the number of time the electromagnetic waves repeats per second. A complete sinusoidal wave looks like the repetition of the letter S which is sleeping. The frequency is directly proportional to the energy of a single photon which means the higher the frequency, the higher the energy. Low frequency energy waves carry less energy and have less penetrability. Every animate or living structure has a certain natural innate or resonating frequency and it applies to all levels from organisms to subatomic particles. When two objects having similar or natural frequency come together, they interact without touching. For example when soldiers march in step on a bridge, the bridge can collapse due to the resonance that is caused. On the other side, a soprano, singing with a high note can shatter its glass because it coincides with the natural frequency of the glass. The atoms in the glass vibrate so strongly because they are resonating with that frequency and they cannot hold it together so they shatter. Cancer is the end result of a series of genetic alterations that modify the control of promoting (oncogenes) or inhibit (suppressor gene) cell proliferation. Conventionally chemotherapy and radiation employ nonspecific toxic effects to inhibit the proliferation of both normal and tumor cells they are aimed at cells which are proliferating very rapidly and they have very significant side effects. The co-ordination between cell membrane potential and cancer cell proliferation has been known for decades, one of the pioneers of this is Dr. Clarence Cone who in 1970 authored a classic paper. Direct measurements have shown that there is 6-7 times higher conductance in tumors compared to normal tissue. The electrical changes occur because of rapid proliferating and transformed cells have lower membrane potential when compared to normal cells. The cancer cells have transmembrane potential which is about 20-30 mv which is much reduced as compared to normal cells which is about −70 to −90 mv. These magnetic fields can modulate the activity of sodium potassium pump that is responsible for setting transmembrane potential. Recent studies in Columbia University have mapped the original frequency to control the activity of numerous enzymes including the sodium potassium pump which is described in the Journal of Biochemistry 53171-4/ 2001. The specific cellular machinery that turns the knob on and off in response to the electromagnetic frequency has been recently identified as has been described in the Journal of Cell Biochemistry GS Cell Biochem 81143-8 2001. Magnetic resonance therapy can combat cancer by directly inducing tumor cell death by activating the pro-apoptotic pathway, activation of anti-tumor immune response and starving the tumor cells by inhibiting the blood supply. Recent studies have demonstrated that specific frequencies can inhibit cancer by blocking the tumor blood supply as has been described by Anti Cancer Research 21388791 2001.

US Patent Publication No. 2007/0208249 discloses an apparatus for the application of what is claimed to be a rotational focused quantum magnetic resonance on any part of human body. The apparatus consist of a plurality of guns for the delivery of the quantum magnetic resonance, a travelling platform for carrying the person under treatment, an electronic switching system for controlling the guns, said electronic switching system being controlled by a main computer through an on board microprocessor and means for cooling and dispersing the heat generated during the operation. Further in this system the 96 guns are used at an angle of 11.25°.

The following aspects of the US Patent Publication No. 2007/0208249 are noted:

The construction of the guns as described in the patent specification is constructed of special cores of high permeability material that is precisely coiled with pure copper. It is apparent that such a construction is not the desired method capable of producing a focused magnetic field;

The placement of the guns at 11.25° cause interference due to the magnetic field generated by the two adjacent guns thereby causing magnetic field in-homogeneity;

The system as disclosed cannot produce a "magnetic resonance" as there is only a magnetic field and no associated radio frequencies to produce the magnetic resonance and therefore the concept of "for the delivery of the quantum magnetic resonance", as stated in the patent specification is misleading and consequently cannot be the basis for any treatment; the specification is devoid of any constructional details; the specification does not disclose any method of treatment; the specification also states that the magnetic field is rotating which means that the field remains on all the time and the switching system rotates the magnetic field a specific rate details of which are not disclosed in patent specification; the above patent application neither teaches the construction of the apparatus nor does it describe any method of treatment.

The conventional systems described above lack homogeneity of magnetic fields which is an essential condition for effectiveness of treatments, and also flexibility of options in terms of field directions, orientations, etc. Further, most literature in this field lack the desired details of the apparatus and/or the methods of treatment making it practically impossible for a person trained in the art to either reproduce the reported effects and/or build the scantly described apparatus.

There is a long felt need to provide a comprehensive system for inducing cellular regeneration and/or degeneration processes and methods of treatment based on such processes that can be easily be applied to diverse states of tissue abnormalities or dysfunctions.

SUMMARY

In accordance with embodiments of the invention a Sequentially Programmed Magnetic Field (SPMF) therapeutic system and method comprise a plurality of arrays of magnetic field generators (MFGs) to produce sequentially programmed pulsed magnetic fields at a focal region, the pulsing being controlled by a switching system operably linked to a computer that generates the operating protocol based on an embedded logic that is dependent on the disease type and the treatment to be administered.

The invention SPMF Therapeutic System is a system that induces cellular regeneration and/or the degeneration processes and methods of treatment based on such processes.

Electromagnetic fields of certain frequency ranges and intensities are indigenous to living tissues and it has been found that inciting the inherent resonance by exogenous treatment using an SPMF can induce cellular regeneration and/or degeneration processes.

Some embodiments of the invention provide an apparatus for generating and applying a magnetic field to a desired tissue comprising: a plurality MFGs to produce sequentially programmed pulsed magnetic fields at a focal region; and a switching system to control the pulsing dependent on the disease type and the treatment to be administered.

Some embodiments of the invention further provide a tubular gantry for housing the MFGs; wherein the MFGs are fixed circumferentially on the tubular gantry in regular intervals of about 15 to about 90 degrees with respect to an adjacent MFGs with reference to the central axis of said tubular gantry, which is the focal axis.

In some embodiments, the plurality of MFGs are operatively coupled in mated, opposed pairs, such that pairs of MFGs which are about 180 degrees opposite to each other in the tubular gantry are energized at the same time and out of phase so that the net magnetic flux passes through the core of the tissue or the centre of the region of interest.

In some embodiments, the invention provides an apparatus, further comprising a tubular gantry, defining from about 1 to about 12 transverse planes with respect to the central axis of said gantry along which the plurality of MFGs are located. In some embodiments, the gantry defines from about 1 to about 9 transverse planes. In some embodiments, the gantry defines about 1 to about 5 transverse planes. On each transverse plane, about 2 to about 24 MFGs are disposed radially over the circumference of the gantry. Diametrically opposite MFGs are operatively coupled to form about 1 to about 12 pairs wherein each of the pairs can be excited to generate a magnetic field.

In some embodiments, circumferentially adjacent MFGs are displaced from each other by regular intervals of about 15 to about 180 degrees. As will be appreciated, the number of MFGs and the angle are directly related to one another. A pair of MFGs will be about 180 degrees from each other. In an apparatus employing 24 circumferential MFGs each MFG will be about 15 degrees from the next adjacent MFG. For example, when the MFGs are placed at regular intervals the following table sets forth the number of pairs, the number of MFGs in each transverse plane, and the approximate angle between adjacent MFGs.

| Pairs | 1 | 2 | 3 | 4 | 5 | 6 | 7 | 8 | 9 | 10 | 11 | 12 |
|---|---|---|---|---|---|---|---|---|---|---|---|---|
| MFGs | 2 | 4 | 6 | 8 | 10 | 12 | 14 | 16 | 18 | 20 | 22 | 24 |
| Angle θ | 180 | 90 | 60 | 45 | 36 | 30 | 25.71 | 22.50 | 20 | 18 | 16.4 | 15 |

In some embodiments of the invention, each MFG comprises a magnetically conductive hollow cylindrical base body extending at one end into a funnel; a magnetically conductive rod-like structure extending through said hollow cylindrical base into said funnel; and an electrical coil wound around the hollow cylindrical base body and the funnel.

In some embodiments the rod-like structure defines a frusto-conical end which extends into said funnel.

In some embodiments, an external magnetic shield is provided to the MFG for limiting leakage of magnetism except through the funnel end.

In some embodiments, the cylindrical base body and funnel are made from leaded steal, such as, but not limited to EN1A.

In some embodiments, the rod-like structure is a ferrite rod. The ferrite rod is about 35 mm long, and about 8 mm in diameter.

In some embodiments, the electrical coil is a copper wire. In some embodiments, the copper wire is 29G copper wire winding of about 46 mm and length of about 60 mm, and the number of turns is about 4200.

In some embodiments, the magnetic field generating device has an impedance of from about 80 and about 90 ohms Some embodiments of the invention provide methods for inducing cellular regeneration and/or degeneration and for methods of treating certain diseases, disorders, or conditions. Some embodiments provide a method for inducing cellular regeneration and/or degeneration in a patient in need thereof comprising: applying a pulsed magnetic field to a desired tissue in a sequential pattern. In some embodiments, the sequential pattern is substantially rotary.

In some embodiments, the pulsed magnetic field is generated by a plurality of mated and opposed pairs of MFGs, wherein mated and opposed pair fire simultaneously and out of phase, and each pair is fired in a sequential, substantially rotary pattern.

Some embodiments provide a method for treating cancer in a patient in need thereof, comprising applying a pulsed magnetic field to a desired tissue in a sequential pattern, wherein the pulsing frequencies are in the range of about 120 to about 2000 Hz.

In some embodiments of the method of treating cancer comprises the step of applying the pulsed magnetic field further comprises: applying a sensitizing treatment phase at a frequency range of about 0.1 Hz to about 600 HZ; and then applying a stimulating treatment phase a frequency range of approximately 600 Hz to about 2000 Hz. In some embodiments, the treatment may be administered for about 1 hour per day for about 28 days.

Some embodiments provide a method for treating arthritis in a patient in need thereof, comprising applying a pulsed magnetic field to a desired tissue in a sequential pattern, wherein the pulsing frequencies are in the range of about 8 to about 50 Hz.

In some embodiments of the method of treating arthritis, the step of applying the pulsed magnetic field further comprises: applying a sensitizing treatment phase at a frequency range of about 8 Hz to about 20 HZ; and then applying a stimulating treatment phase a frequency range of approximately 12 Hz to about 40 Hz. The treatment is administered for about 45 minutes to 1 hour per day for about 28 days.

In some embodiments, the invention provides a method for treating neurodegenerative disorders in a patient in need thereof, comprising applying a pulsed magnetic field to a desired tissue in a sequential pattern, wherein the pulsing frequencies are in the range of 30 Hz to about 120 Hz.

In some embodiments, the step of applying the pulsed magnetic field further comprises: applying a sensitizing treatment phase at a frequency range of about 30 Hz to about 60 HZ; and then applying a stimulating treatment phase a frequency range of approximately 90 Hz to about 120 Hz. The treatment may be administered for about 1 hour per day for about 21 days.

In some embodiments, the neurodegenerative disorder to be treated is selected from Alzheimer's, Parkinson's, ALS, and Huntington's disease, in retinal degeneration, and other damage to sensory systems associated with stroke, head and spinal trauma, epilepsy, drug and alcohol abuse, infectious diseases, mental disorders, or from exposure to industrial and environmental toxicants, and chronic pain.

Additional features and advantages of the invention will be made apparent from the following detailed description of illustrative embodiments that proceeds with reference to the accompanying drawings.

BRIEF DESCRIPTION OF THE DRAWINGS

The foregoing and other aspects of the present invention are best understood from the following detailed description when read in connection with the accompanying drawings. For the purpose of illustrating the invention, there is shown in the drawings embodiments that are presently preferred, it being understood, however, that the invention is not limited to the specific instrumentalities disclosed. Included in the drawings are the following Figures:

FIG. 2 is a schematic of the ferrite rod;

FIG. 7 shows a layout of exemplary MFG devices;

FIG. 8 shows a layout of exemplary MFG devices;

FIGS. 9A-9E diagnostic images of a 30 year old female—Synovial Sarcoma with Mets in right lung and Mediastinal Lymph Nodes; (9A diagnostic CT Scan, 9B pretreatment CT Scan, 9C Mid-treatment CT scan, 9D immediately post-treatment scan, 9E—post treatment scan);

FIGS. 10A-10L are diagnostic images of a 55 year old male—Left Posterior Frontal—GBM (WHO Grade—IV); (10A, B, C pretreatment scans, 10D, E, F immediately post-treatment scans, 10G, H, I 4 months post treatment, 10J, K, L, 9 months post treatment);

FIGS. 11A-11D is an exemplary case summary for Osteo Arthritis;

FIG. 12 is a pictorial representation of a human cell and organelles;

FIG. 13 illustrates an outline of the ATP-synthase macromolecule showing its subunits and nano machine traits;

FIG. 14 shows Centriole in the normal cell cycle;

FIG. 15 shows Centriole in the abnormal cell cycle;

FIG. 16A is a flow chart for patient treatment of cancer;

FIG. 17A is a flow chart for patient treatment of arthritis;

FIG. 18 is a flow chart for patient treatment of neuro-tinnitus; and

DETAILED DESCRIPTION OF ILLUSTRATIVE EMBODIMENTS

Figure 1A:
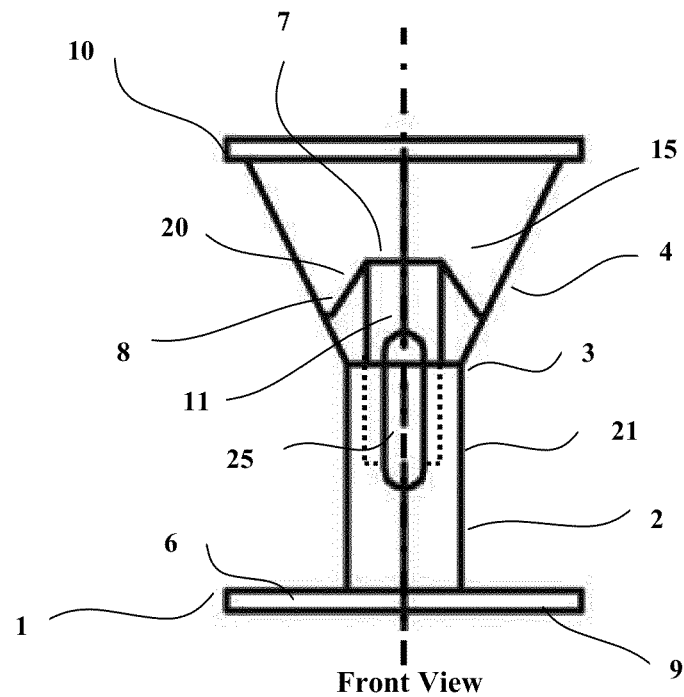
FIGS. 1A and 1B are schematics of the section of magnetic field generating device.

The Sequentially Programmed Magnetic Field (SPMF) therapeutic system is a computer controlled device which generates sequential pulsed magnetic fields, by employing a plurality of Magnetic Field Generators (MFGs). The magnetic field can be precisely controlled and applied onto the cells and/or tissues that require the treatment. The MFGs are fired in a programmed sequence to facilitate the focusing of the magnetic field and is believed to result in better patient outcomes.

Inciting the inherent resonance by exogenous treatment using SPMFs can induce cellular regeneration and/or degeneration processes. In the case of regeneration and degeneration of cells, the pulsing frequencies are in the range of about 0.1 to about 2000 Hz based on the indication of the disease type which is determined by the patient's MRI, CT, Ultrasound or other diagnostic information.

As such, the apparatus may be used to treat conditions where cellular degeneration and/or regeneration is advantageous. In some embodiments, the apparatus may be used in: (i) a method for treating arthritis by causing regeneration of cartilage with the help of the aforesaid apparatus; (ii) a method for degeneration of cancerous tissues by subjecting them to magnetic field generated and applied by the aforesaid apparatus, (iii) a method for treating diabetes by regenerating the islet cells by the use of the aforesaid apparatus; (iv) a method to treat spinocerebellar degeneration and/or multiple sclerosis by the use of the aforesaid apparatus; (v) a method to treat neuro degenerative disorders, such as, but not limited to, Alzheimer's, Parkinson's, ALS, and Huntington's disease, in retinal degeneration, and other damage to sensory systems (e.g., visual, auditory, somatosensory), in stroke, head and spinal trauma, epilepsy, in drug and alcohol abuse, in infectious diseases, in exposure to industrial and environmental toxicants, and, perhaps, in mental disorders and chronic pain; (vi) a method for treating non-healing fractures and other bone conditions; (vii) a method for treating various other conditions that could benefit from regeneration or degeneration of tissues.

An apparatus for inducing a SPMF in biological tissue(s) comprises means for generating and applying magnetic fields to the biological tissue(s) from one or more pairs of oppositely placed means for generating and applying magnetic fields. The magnetic field is generated simultaneously by mated opposed pairs of MFGs. In some embodiments, the magnetic field is applied in a sequential programmed manner by different mated opposed pairs. In some embodiments, a magnetic field of the same strength is generated and applied to the said tissue(s) from each oppositely placed MFG in each pair. The sequential application may be conducted in mated opposed pairs or in selected groups of mated opposed pairs of MFGs. The sequential program, in some embodiments, is generally rotary in nature, wherein the firing sequence of the MFGs generally flows circumferentially from one adjacent MFG to the next. In the case of the system having multiple rows of MFGs, in some embodiments, the firing sequence continues to the next adjacent row for sequential circumferential firing of the MFGs, and so on until the desired program is completed.

Figure 1B:
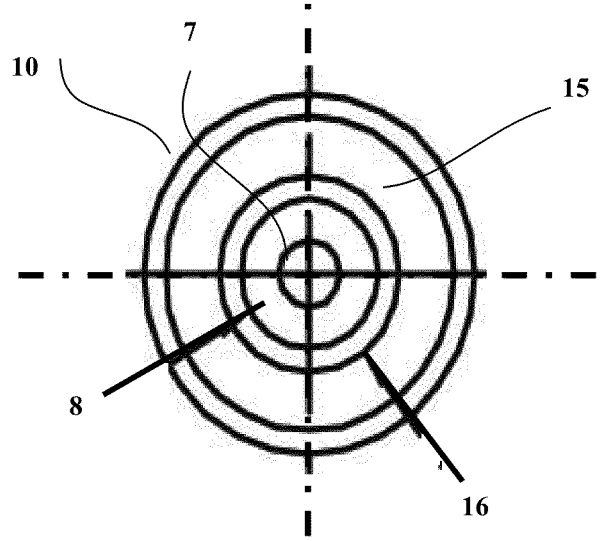

Referring to FIGS. 1A and 1B, each MFG comprises a hollow cylindrical base body ending in a funnel, made of material capable of magnetic conduction. The body houses a rod-like structure having good magnetic conductivity. An electrical coil is wound around the hollow base body and its funnel end and connected to an electrical supply to generate magnetic field. An external cover may be optionally provided to minimize or prevent leakage of magnetic field. The one or more pairs of MFGs are housed in a tubular gantry, preferably in transverse rows of more than one and circumferentially at an angle of about 15 to about 90 degrees with respect to one another based on the focal point located on a transverse axis of the tubular gantry, where the biological tissue to be treated is placed.

The methods proposed by this invention for regeneration or degeneration of tissues in the treatment of the aforesaid ailments, and others, involves planning the exposure of the tissues to a SPMF generated by the apparatus and thereby to induce a pulsed magnetic field. The extent of the exposure to such pulsed magnetic field would depend upon the amount of progression of the condition, for example the amount of degeneration that is already set in and other factors depending on the condition to be treated. The plan results in a determination of one or more of the following, frequency to be used, field width, field intensity, duration of each pulse, pattern of the sequential program, duration of individual treatments, number of treatments required, etc.

Upon application, the area to be treated is aligned at the focal point. A sensitizing treatment phase may be used depending upon the treatment plan and the condition to be treated. Then, a stimulating treatment phase wherein the magnetic field is generated and applied according to the plan. The magnetic field is generated and applied in a sequential pattern. After the desired number of treatments, the patient can be reevaluated and the plan adjusted and/or reassessed if necessary.

In the case of regeneration and degeneration of cells, the pulsing frequencies are in the range of about 0.1 Hz to about 2000 Hz based on the indication of the disease type which may be determined, for example, by either the patient's MRI, CT, Ultrasound or other technique. In some embodiments, the pulsing frequencies are in the range of about 120 Hz to about 2000 Hz. In some embodiments, the pulsing frequencies are about 5 Hz to about 120 Hz. In some embodiments, the pulsing frequencies are in the range of about 1 Hz to about 600 Hz. In some embodiments, the pulsing frequencies are about 8 Hz to about 50 Hz. In some embodiments, the pulsing frequencies are about 30 Hz to about 120 Hz.

The Apparatus

In accordance with embodiments of the invention a Sequentially Programmed Magnetic Field (SPMF) therapeutic system and method comprise a plurality of arrays of MFGs to produce sequentially programmed pulsed magnetic fields at a focal region, the pulsing being controlled by a switching system operably linked to a computer that generates the operating protocol based on an embedded logic that is dependent on the disease type and the treatment to be administered.

Generally, the apparatus comprises a plurality of MFGs 100 to generate and apply magnetic field. The MFGs 100 are fixed circumferentially on a tubular gantry 101 in regular intervals of about 15 to about 90 degrees with respect to adjacent MFGs 100 with reference to the focal axis 500.

Each MFG 100 consists of a hollow cylindrical base body 2 extending into a funnel 4. It is made of material capable of magnetic conduction; a rod like structure (FIG. 2, 30) having good magnetic conductivity fixed within the cylindrical base body 2 extending into the funnel 4; an electrical coil 95 wound around the hollow cylindrical base body 2 and the funnel 4. (Electrical coil 95 is not shown in FIG. 1A for clarity.

The electrical coil 95 is connected to an electrical supply. The electrical coil 95, on passing of electric current generates magnetic field. The funnel end 4 of each MFG 100 faces inside the tubular gantry 101 toward the focal axis 500.

The rod like structure in the MFG increases the strength and uniformity of the magnetic field thereby increasing the efficacy of the apparatus.

Figure 3:
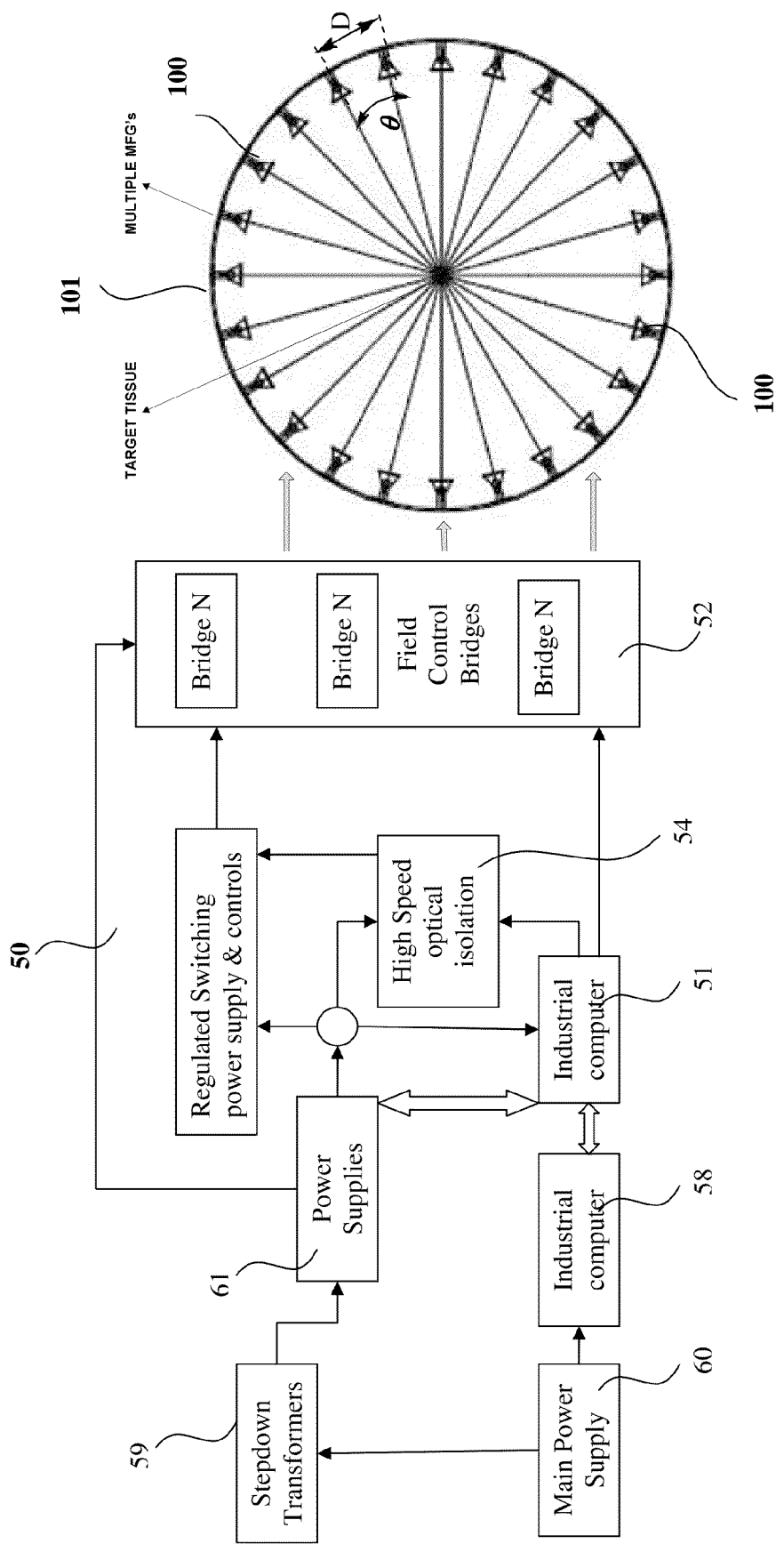
FIG. 3 shows a block diagram of the embedded system.

The MFGs are located at such an angle θ and at such a distance D from each other so as to reduce or eliminate interference between the magnetic field generated by the given means and the residual magnetic field of the adjoining means. FIG. 3 shows a block diagram of the embedded system, θ shows the angle between adjacent MFGs. The distance between circumferentially adjacent MFGs is shown as D, and depends on the size of the machine, the number of MFGs, and the angle θ between them. In one exemplary arrangement with 24 circumferential MFGs, θ is 15 degrees and the distance D between adjacent circumferential MFGs is 129.25 mm Shielding of housing of the MFGs and/or the system by an external cover may be employed to limit or prevent leakage of the magnetic field thereby increasing the efficacy of the apparatus and making it safe to operate.

The apparatus may contain additional components that make the apparatus more useable or user friendly or enhance performance. For example: a fan can be employed to circulate air around the tubular gantry 101 to prevent collection of dust and static charge which potentially interferes with the magnetic field. An external cover may be provided to shield the tubular gantry 101 against leakage of magnetic field. A bed on a supporting stand having cushion may be used, sliding a patient lying thereon into the tubular gantry 101 with the help of supporting motor (not shown), gear railings, bearings and supporting railings. As such tissues of the patient which are to be treated can be positioned at the focal point where the magnetic field generated from the MFGs 100 is focused.

In most other treatment devices with energizing coils, the coils are unidirectional. In this method, the coils are bidirectional because the coils which are approximately 180 degrees opposite to each other in the tubular gantry 101 are energized at the same time and out of phase so that the net magnetic flux passes through the core of the tissue or the centre of the region of interest. That is, mated opposed pairs of MFGs fire simultaneously from opposite directions. The constant switching or the energizing of coils in a rotary pattern causes the focusing to occur in a relatively small area which is the tissue to be treated. This high speed switching causes focusing similar to that achieved in the principles of tomography or computerized tomography. The net magnetic flux can be directed at the center of the region of interest (i.e. focal point) with very little emission required from each of the MFGs.

Data is fed into a computer coupled to and controlling the apparatus. Based on the disease type, the duration, and nature of the disease etc., the computer software calculates the duration of the exposure, the pulse frequency, the frequency of the firing and the amount of SPMF depending on the patient and the disease.

The following embodiments describe how the entire system functions as a comprehensive apparatus to produce the SPMF specifically for a particular disease type. The embedded system comprises a computer, high speed processing controller, power supplies, MFGs, a cylindrical gantry that, in some embodiments, includes a total of 216 MFG's that produce the sensitizing and stimulating frequency's required to treat specific disease types. More or fewer MFG's could be employed depending upon the application, size and arrangement of the apparatus. Particularly, it should be noted that full body apparatus are contemplated as shown in the drawings, but smaller models suitable for treatment of, e.g. the elbow or knee are also contemplated.

In accordance with one embodiment of this invention, the sequential programmed magnetic field generation system may include:

an embedded system comprising a high speed processing microcontroller configured with a power drive module that comprises a digital to analog converter for set voltage reference of regulated field strength, pulse width modulation circuit, optional current sensing circuit configured with operational amplifier, digital to analog converters, PWM supported ASICS & MOSFETs, optical isolations to ensure complete isolation between processor system and analog system;

a pulse drive module comprising power MOSFETs in "H" bridge formation with heat sinks, gate drive systems through optically isolated drive modules and a set of transistors, optical isolation system for isolating main processor module with power MOSFETs system, a set of LED's for physical verification of proper excitation of magnetic coils, power rectifier's fuses and surge protection system;

a step down transformer configured with main AC power supply; personal computer; set of fault monitoring LEDs;

wherein the embedded system is provided with interrupt provision that enables serial communication, timers for controlling the sequential operation of exciting the coils of the core, power monitoring facility wherein if voltage drops below designed value, the critical parameters are saved in the flash memory of central processing unit;

wherein the embedded system is configured with a plurality of MFGs;

wherein plurality of such MFGs are circumferentially disposed on the internal diameter of a cylindrical structure such that the devices are disposed diametrically opposite to each other in each cross section of the cylinder;

wherein the surface of the cylindrical structure is mounted with such MFGs in longitudinal direction;

wherein the magnetic field generating device is controlled by the embedded system to generate tailored pulsed magnetic fields directed to a region of interest or focal point;

an initialization module wherein peripherals and sub systems are configured wherein baud rate for serial transfer of data between PC and processor, timer periodicity and wait time for packet transfer set/initialized;

a serial—data receiving module to receive the data and command from the personal computer and validate the packets received, accept/reject packets and send acknowledgment;

a packet evaluation module to evaluate the packet for correct node address, CRC check and ensure commands and data are within the acceptable limits;

an acknowledgement module to transmit any and requested data packets to the personal computer;

an executive command module to initiate process in respect of treatment sequence, stop on set time expiry, pause or stop command issued by system operator from the personal computer;

wherein the diametrically disposed coils of the paired MFGs are connected in series and subjected at a time to a rectangular pulse operating out of phase with respect to each other to produce an effective magnetic field at the region of interest; wherein the pulse characteristics are selected from frequency of about 0.1 Hz to about 2 KHz, pulse count of about 2 to about 50, current of about 0.1 to about 5 amps, voltage from about 20 to about 65 V, producing effective magnetic field of about 0.01 to about 5 mT, wherein the time duration between the switching off and the switching on of the adjacent pair diametrically disposed MFGs is about 1 msec to about 5 msec.

Figure 19:
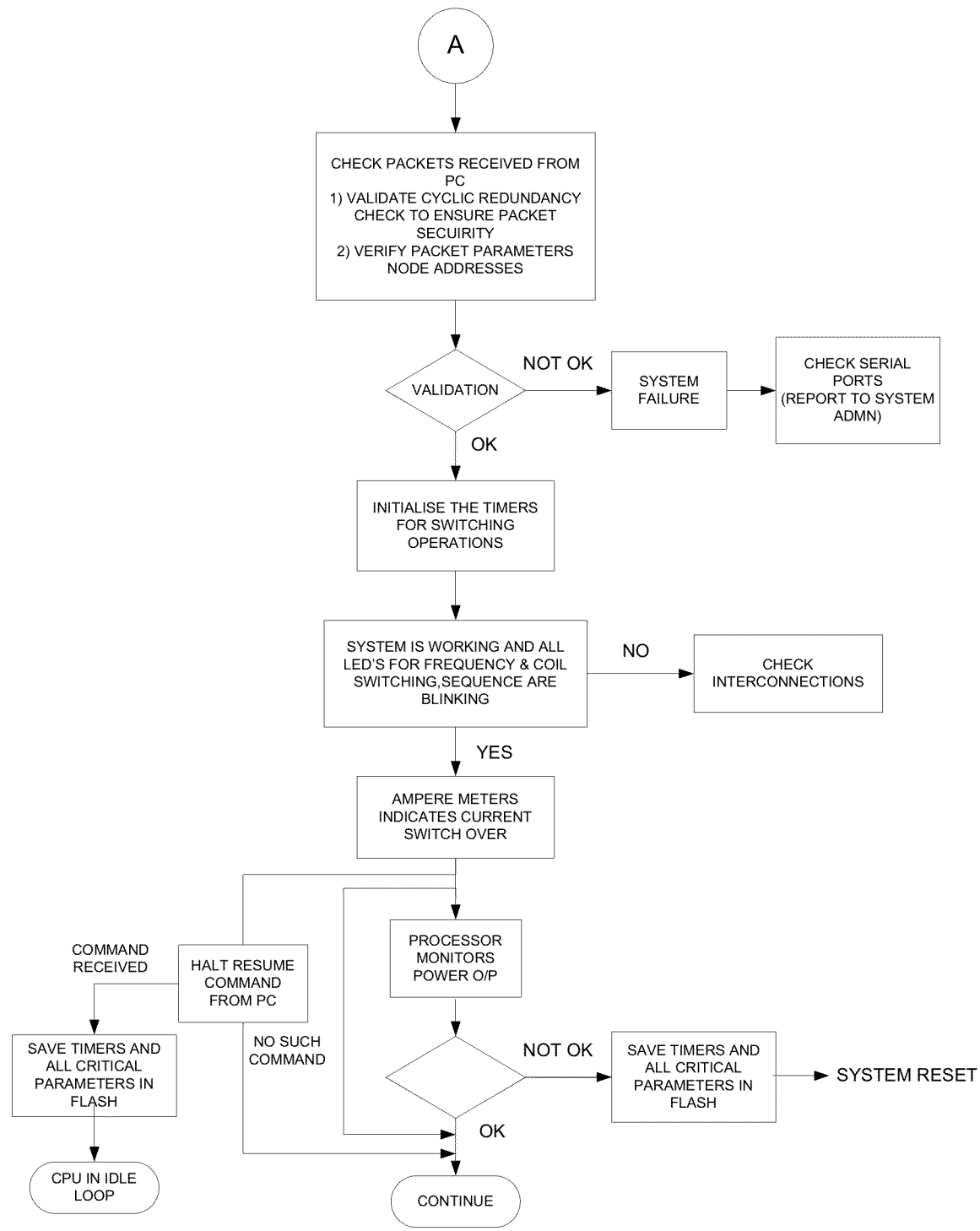
FIG. 19 is a flowchart illustrating exemplary logic for a sequentially programmed magnetic field (SPMF) therapeutic system.

These features of the processes have been illustrated in FIG. 19—system flowchart.

Figure 6:
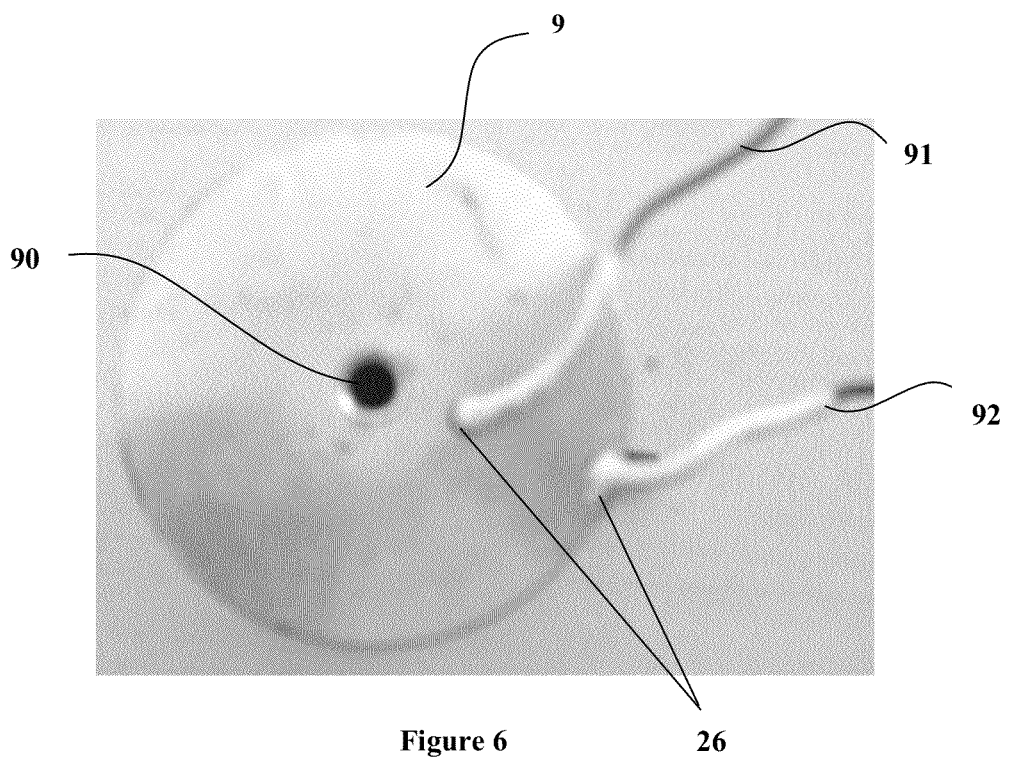
FIG. 6 shows an exemplary wound magnetic field generating device.

FIG. 1A and FIG. 1B describe one embodiment of a magnetic field generating device (MFG) 100 employed in the magnetic field generating system. As shown, the magnetic field generating device 100 may comprise a disc shaped base mounting member 1 wherein cylindrical base body 2 is disposed substantially perpendicular to the first surface 6 of the disc shaped mounting member 1 and stands upwards from the first surface of the disc shaped mounting member. A mounting provision 90 as indicated in FIG. 6 (as seen in the bottom view of the mounting member 1) in the form of a preferably threaded hole is provided in the center of the cylindrical base body 2 wherein the opening of the hole is on the second surface 9 of the disc shaped mounting member 1. The other end portion 3 of the cylindrical base body 2 develops up in to a conical structure or funnel 4 as seen in FIG. 1A with outwardly diverging slant lateral surface (of generation) that forms the surface of the cone wherein the cross section of the apex portion which is the apical portion of the funnel 4 is equal to the diameter of the cylindrical base body 2. A base portion is provided with a rim like substantially flat portion 10.

A concentric cavity 11 is provided inside the cylindrical base body 2 wherein the cavity opens in the inner portion 15 of the conical member 4 at the opening 7 that elevates inside the conical portion wherein the opening 7 forms apical portion of a second conical frustum 20 comprising lateral surface of generation 8 extending downwards towards the cylindrical base body 2 wherein the lateral surface 8 intersects the inside lateral surface of the conical member 4 to form annular space 16 as shown in FIG. 1B which is the top view of the FIG. 1A. The cavity 11 is adapted to receive a ferrite rod 30 (FIG. 2) wherein one of the end portions 31 is in the form of a truncated conical geometry.

Figure 5:
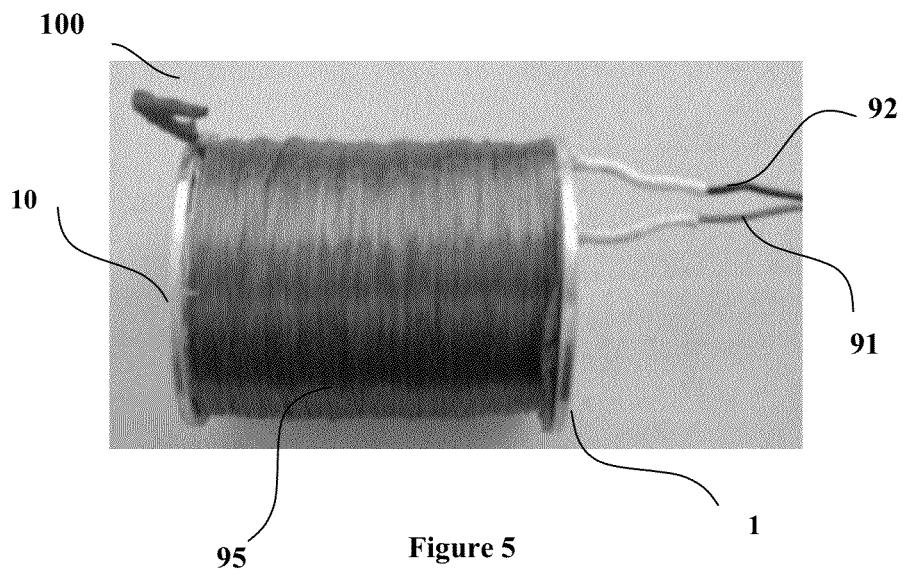
FIG. 5 shows an exemplary wound magnetic field generating device.

The outer surface 21 of the cylindrical base body 2 is provided with one or plurality of axial slots 25 wherein portion of the slot extends in the lateral surface of generation of the conical member 4. The mounting member 1 is provided with one or plurality of holes 26 as illustrated in FIG. 5 and FIG. 6 for insertion of wire/conductor terminals 91 and 92.

The outer surface of the conical member 4 and the cylindrical base body 2 may be wrapped with a magnetically permeable paper (e.g., elephant paper). An electrical coil 95 is wound over the entire outer surface to form the magnetic field generating device which is illustrated in FIG. 5. The electrical coil 95 may be a copper conductor. It can be seen that the electrical coil 95 is wound from the mounting member 1 up to the rim like portion 10. The conductor terminals 91 and 92 are inserted from the holes 26 provided in the base 1 as shown in the FIG. 5 and FIG. 6 (bottom view).

Figure 4:
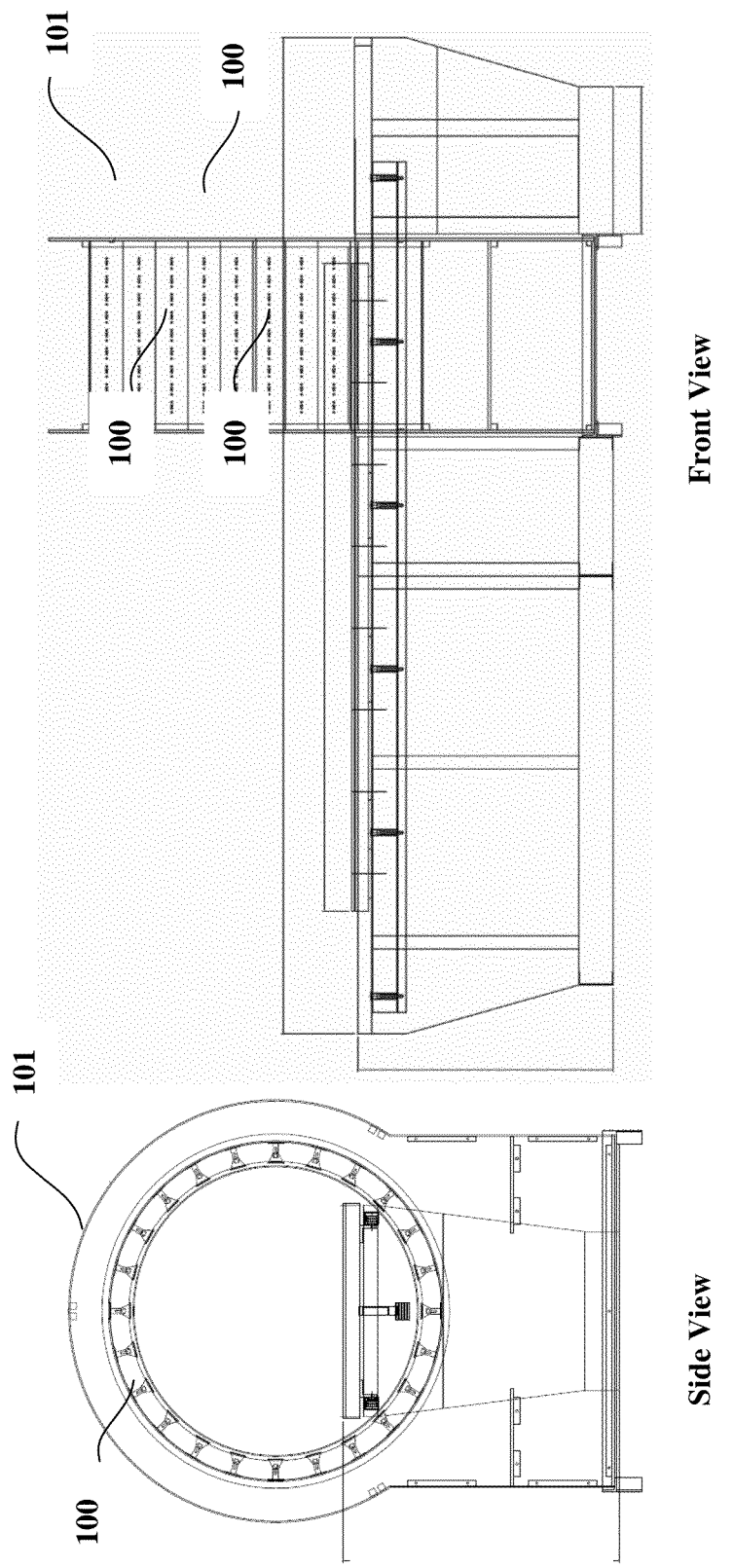
FIG. 4 is a schematic of system configuration.

In some embodiments, the cylindrical base body 2 is made from EN1A leaded steel, the ferrite rod is about 35 mm in length, about 8 mm in diameter and about 25 degree slope, and the diameter of the exemplary 29G copper wire winding is about 46 mm and the length of about 60 mm The number of turns is about 4200. This arrangement results in an impedance of between about 80 and about 90 ohms FIG. 3 and FIG. 7 depict circumferential disposition of the plurality of MFGs 100 on a cylindrical structure 101 subtending at an angle of about 15 degrees to about 90 degrees to each other based on the application and end use. The MFGs 100 are arranged in pairs disposed diametrically opposite to each other about focal axis 500. FIG. 4 depicts front and side views of the structure wherein the surface of the cylindrical structure 101 includes multiple MFG pairs mounted in rows wherein each of the rows comprises a plurality of the MFGs as shown in the front view.

In some embodiments, the MFGs are arranged in a clustered configuration on the tubular gantry 101 as depicted in FIG. 7. In some embodiments, the gantry 101 may be divided into a plurality of segments. For example, it may be divided into three segments A, B and C as indicated in the FIG. 7. It may be noted that the segments in the FIG. 7 are indicated separately for better elaboration and appreciation of the aspect of clustered configuration only, it should not be construed that the three segments of the cylindrical structure are physically separated. Each of the segments is provided with rows arranged in the longitudinal direction along the focal axis 500 disposed over the circumference of the segment wherein each of the segment rows 200 include three MFGs 100a, 100b and 100c. The devices in other rows are indicated with dashed lines in the FIG. 7. In the embodiment depicted in FIG. 7, there are total 9 MFGs in one longitudinal row across the gantry clustered into a set of three devices on each of the segments A, B and C.

In the illustrated embodiment, there are 24 MFGs disposed radially over the circumference of the gantry 101 in each transverse plane to the axis 500. The diametrically opposite devices are paired to form twelve such pairs wherein each of the pairs is excited to generate a magnetic field. Assuming three such transverse planes in each segment corresponding to each of the MFGs (such as 100a, 100b and 100c), there are 24 devices in each transverse plane and three such planes totaling 72 MFGs in each segment. In another embodiment, the number of such devices in each row and transverse plane may vary depending on end application.

The MFGs of each of the segments are configured or operatively coupled to a control means. In some embodiments, there are three such control means corresponding to the three segments. The control means is configured with the embedded system for controlling magnetic field strength, sequence and frequency of field excitation in a tailored manner according to the treatment protocol.

The MFGs 100 of the system are configured with the embedded system 50 that is represented in the form of a block diagram in FIG. 3. The embedded system 50 comprises a high speed processor 51 wherein in one embodiment the processor is an analog device 32 bit ARM based processor working at about 40 MHz frequency microcontroller comprising peripherals such as serial communication interface, circuit for set voltage controller reference system and Logic IC'S for coordinated operation for power MOSFETs at digital TTL level that is configured with, for example:

a power drive module comprising digital to analog converter for set voltage reference of regulated field strength, pulse width modulation circuit, optional current sensing circuit configured with operational amplifier, digital to analog converters, PWM supported ASICS & MOSFETs. Further, the module has optical isolations 54 to ensure complete isolation between processor system and analog system;

pulse drive module comprising power MOSFETs in "H" bridge formation with heat sinks, gate drive systems through optically isolated drive modules & set of transistors, optical isolation system for isolating main processor module with power MOSFETs system, set of LED's for physical verification of proper excitation of magnetic coils, power rectifier's fuses & surge protection system;

step down transformer 59 configured with main AC power supply 60;

personal computer 58;

set of fault monitoring LEDs;

wherein the embedded system is provided with interrupt provision that enables serial communication, timers for controlling the sequential operation of exciting the magnetic coils of the core, power monitoring facility wherein if voltage drops below about 3.3 volts, the critical parameters are saved in the flash memory of central processing unit;

wherein the main AC power supply of about 230V, about 50 Hz is stepped down to the desired voltage level using the step down transformer 59. Further the stepped down voltage is rectified, filtered and regulated in the power supply circuitry 61 that comprises first circuitry for DC Voltages of about +15V and about −15V that is necessary for operational amplifier, second circuitry for DC Voltage of about 5V that is necessary for logical circuitry, third circuitry for DC Voltage of about 5V and power on indicator circuitry that uses LED as visual indicator. The high speed processor 51, optical isolation circuitry 54 comprising LED and phototransistor integrated together wherein the circuitry 54 provides isolation between analog and digital circuit. The voltage signal from 54 is fed to the field control bridge circuitry 52 along with the signal from the processor 51 that transmits signal based on pulse strength, pulse frequency, pulse Sequence & pulse counts based on the object to be treated. The signals from 54 and 52 are fed to the bridge circuitry 52 that comprises power MOSFETs. The pulse duration, pulse frequency and sequence is controlled using input from the processor.

As shown in FIG. 19, the embedded system operation module may comprise:

initialization module wherein peripherals and sub systems are configured wherein baud rate for serial transfer of data between PC and processor, timer periodicity and wait time for packet transfer is set/initialized;

serial—data receiving module to receive the data & command from the personal computer and validate the packets received, accept/reject packets and send acknowledgment; packet evaluation module to evaluate the packet for correct node address, CRC check and ensure commands and data are within the acceptable limits;

acknowledgement module to transmit any and requested data packets to the personal computer;

executive command module to initiate process in respect of treatment sequence, stop on set time expiry, pause or stop command issued by system operator from the personal computer;

In one embodiment, the embedded system software may be structured to:

Call sub-routines to perform the specific tasks;

System Initiation which starts the peripheral and sub systems as derived by the software;

Validate all data that is being transmitted or received;

Start, executive, command and monitor specific protocol sequences;

Initiate the start sequence, the stop sequence, the frequency and power required for the specific protocol;

Set the pulse strength, pulse frequency, pulse count and pulse counts;

Save all critical parameters in the flash memory of the processor in the event of a power failure.

Methods

In the case of regeneration and degeneration of cells, the pulsing frequencies are in the range of about 0.1 to about 2000 Hz based on the indication of the disease type which was determined, for example, by either the patient's MRI, CT Ultrasound, or other diagnostic information.

Exposure of cancer cells to SPMF therapy normalizes the cell membrane potential, thereby halting the process of cell proliferation, followed by programmed cell death (Apoptosis). A cascade of effects follows normalization of cell membrane potential, i.e. increased influx of Calcium, Potassium ions and Oxygen and efflux of Na and H$_2$O out of cells, and reduction in intracellular acidity.

The normal cells are substantially unaffected by the SPMF. Furthermore, the signals are modulated depending on the proton density of the tumor tissue and impedance of normal cells mitochondrial sensors. The energy delivered during the therapy is well within the safety norms prescribed by the International Commission for Non-Ionizing Radiation Protection (ICNIRP).

In one of the embodiments, the SPMF is used in the treatment of cancer by causing degeneration of tumor cells wherein the pulsing frequencies are in the range of about 120 to about 2000 Hz.

For cancer, the specific relationships and algorithms used are established for the signal intensities between the skin and the tumor hence would cause differential attenuation of these SPMF. First the region of interest and the center of the tumor are marked by a software program, the pixel intensities are calculated along the skin to the center of the tumor about every 15 degrees (or other increment) which corresponds to the placement of each MFG. This information is input into the computer so that the energizing of each MFG can be different based on the field required for a particular MFG. Signal strength is derived from the MRI, CT Ultrasound image or other diagnostic information. Once this is calculated, the dose information is input into the computer. In some embodiments, the treatment protocol first sensitizes the cellular structure and then stimulates the cell to start the regeneration process and initiate the degeneration process. In some embodiments, the treatment protocol first sensitizes the cellular structure at a frequency range of about 0.1 Hz to about 600 HZ and then stimulates the cellular structure at a frequency range of approximately 600 Hz to about 2000 Hz to start the regeneration process and initiate the degeneration process. In some embodiments, the treatment would be for a duration of about 1 hour per day for about 28 days.

The methods of using SPMF therapy for regeneration involves planning of the exposure which is based on the amount of degeneration that is already set in and other factors relevant to the particular condition to be treated. Once the dose planning is done, the patient is marked using ultrasound or other techniques. At the same time, the joint is evaluated for any effusion and marking is done at one or two points where the therapy needs to be delivered. Once the patient is marked, the patient is taken into the SPMF system, for example on a sliding platform, and the magnetic field is focused on to the region of interest, for example with the help of the laser guide, and the treatment runs for the period of time that is designated based on the factors mentioned above.

In one of the embodiments, the SPMF is used in the treatment of arthritis by causing regeneration of cartilage wherein the pulsing frequencies are in the range of about 8 to about 50 Hz.

For Arthritis a predetermined dose profile is formed based on the grade and severity of the arthritis and the permittivity index. Patients who have early stage arthritis receive a low sensitizing frequency in the range of about 8 Hz to about 20 Hz, a stimulating frequency in the range of about 12 Hz to about 40 Hz. Patients who have severe arthritis and a high permittivity index receive a sensitizing frequency of about 10 Hz, and a stimulating frequency up to about 40 Hz. In some embodiments, the treatment is for a duration of about 45 min to about 1 hour per day for about 21 days.

The results confirm significant regeneration of cartilage, increase in the strength and stability of, e.g., the knee joint and improvement in quality of life, as measured with a MRI system and internationally accepted American Knee Society rating system.

In neuro degeneration, the progressive loss of nerve cells occurs in aging and in neuro degenerative disorders, such as Alzheimer's, Parkinson's, ALS, and Huntington's disease, in retinal degeneration, and other damage to sensory systems (e.g., visual, auditory, somatosensory), in stroke, head and spinal trauma, epilepsy, in drug and alcohol abuse, in infectious diseases, in exposure to industrial and environmental toxicants, and, perhaps, in mental disorders and chronic pain. The treatment pulsing frequencies for the neuro protocols are in the range of about 30 Hz to about 120 Hz. The treatment protocol first sensitizes the cellular structure at a frequency range of about 30 Hz to 60 HZ and then stimulates the cellular structure at a frequency range of about 90 Hz to about 120 Hz to start the regeneration process. The treatment time is approximately 1 hour a day for 21 days.

For Ménière's disease the pulsing frequencies are in the range of about 8 to about 30 Hz.

In yet another embodiment of the invention, the SPMF is used to treat non-healing fractures or in treatment of diabetics wherein the requirement is to regenerate the islet cells.

In some embodiments, the SPMF is used for a variety of degenerative or regenerative applications where specific parameters can be determined through similar techniques as used and described above.

Methods of Treatments Using SPMF

SPMF has been used to treat the following disease types; cancer, arthritis, neuro degenerative diseases. The follow sections describe the methods of treatments including non limiting examples to illustrate the utility of the SPMF system.

Treatment Protocols for Cancer—

Figure 16B:
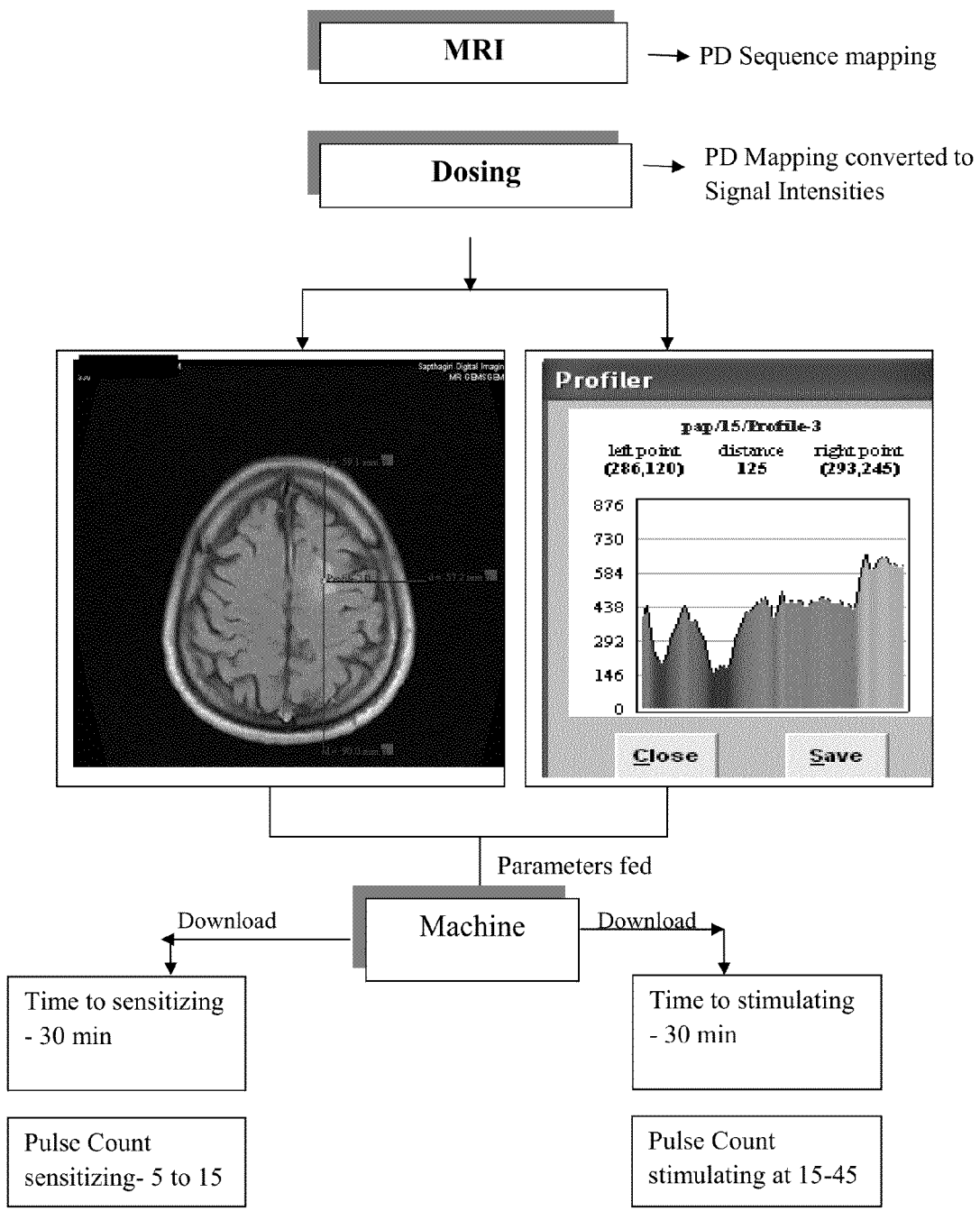
FIG. 16B is a flow chart of a proposed mechanism of action in accordance with an embodiment of the invention.
Figure 16B:
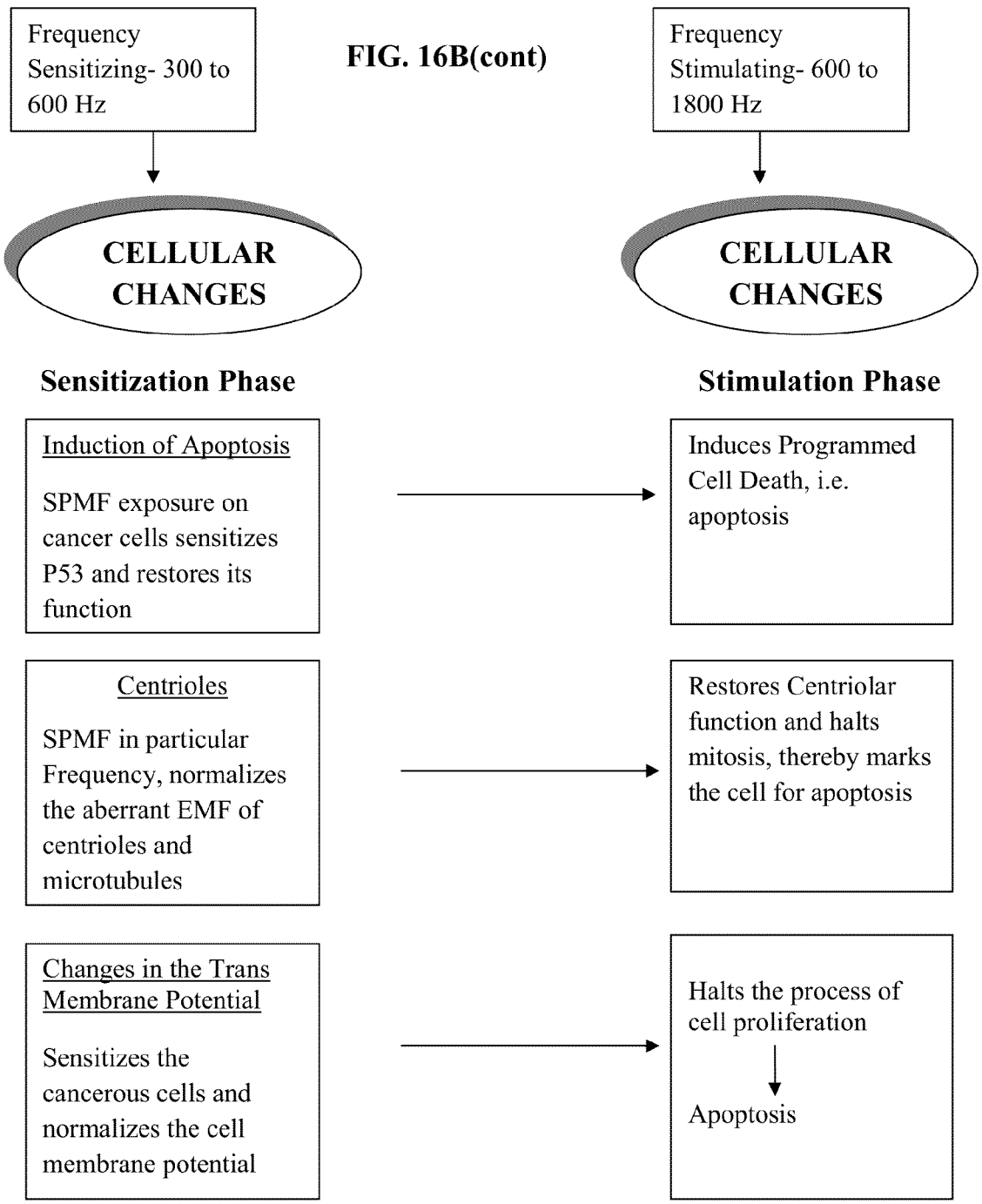

An exemplary patient process flow chart for cancer is illustrated in FIG. 16.

In cancer the process of treatment starts with first localizing the tumor which would be the region of interest (ROI) using the ideal form of imaging i.e. MRI, CT or ultrasound. For example, head and neck tumors are best seen on MRI and lung tumors are best seen on CT scan and thyroid tumors are best viewed on an ultrasound. Once the tumor is localized a specific proton density image (short TE and a long TR) is done through the center of the lesion. Using this proton density image, specific algorithms are obtained based on signal intensities between the skin and the tumor which are different with different tissues and it would cause differential impudence of the SPMF. For the proton density image, the ROI that would be a tumor is marked and uploaded on to a generic software by which these densities are converted to pixel intensities from the skin to the center of the tumor. The intensities are calculated along lines drawn at about 15 degrees from the center of the tumor which would denote the placement of each MFG. The parameters of the signal strength would be different based on how much penetration and frequency is required from the MFG coil based on the intensities of tissue that are between the skin and tumor. The treatment protocol lasts for a period divided into 2 or more phases of predetermined duration where in the first duration the frequencies applied are the frequencies which essentially sensitize the cell membrane and are followed by subsequent duration(s) of stimulating frequency which finally causes change in cell membrane potential. In one embodiment, the treatment protocol lasts for approximately 1 hour and is divided into 2 phases where the first 30 minutes (approximately), the frequencies applied are the frequencies which essentially sensitizes cell membrane and is followed by 30 minutes (approximately) of stimulating frequency which finally causes change in cell membrane potential. Different protocols are set based on proton densities of the tumor. Tumors having high proton density are treated with a high ratio and sensitizing and stimulating that could go to the range of around 2000 Hz. Tumors with low density are treated with lower sensitizing and stimulating frequencies ratio and these frequencies range to about 120 Hz.

Algorithm for High Proton Density

1) Minimum Density=$3^{rd}$ minimum of Pixel Value
   a. The minimum density is derived by discarding the 2 lowest recorded proton density pixel values (formula b) and the program will register the $3^{rd}$ lowest value as the "minimum density". This methodology is being used because the density value of air is very low and would distort the calculation.
   b. S=PD exp(-TE/T2)(1-exp(-TR/T1))(n)
      i. In this equation, S is the brightness (signal) measured at some particular point in the image—at some particular "pixel"; PD is "Proton Density", the number of hydrogen atoms in the region corresponding to that pixel; and T1 and T2 are the corresponding time constants for that pixel.

2) Maximum Density=$3^{rd}$ Maximum of Pixel Value
   a. The maximum density is derived by discarding the 2 highest recorded proton density pixel values (formula b) and the program will register the $3^{rd}$ highest value as the "maximum density". This methodology is being used because the density value of bone is very high and would distort the calculation.
   b. S=PD exp(-TE/T2)(1-exp(-TR/T1))(n)
      i. In this equation, S is the brightness (signal) measured at some particular point in the image—at some particular "pixel"; PD is "Proton Density", the number of hydrogen atoms in the region corresponding to that pixel; and T1 and T2 are the corresponding time constants for that pixel.

3) Average Density=(Sum of Pixel Values/No. Of Pixel Values)
   a. The average density is derived by dividing the sum of the all the Pixel Values in the region of interest by the total number of pixels in the region of interest 4) Skin To Target=Root((xe-xs)^2+(ye-ys)^2)
   a. The Skin to Target value is derived by the root value of xe (x axis target)-xs (x axis Skin) squared plus ye (y axis target)-ys(y axis skin) squared 5) Sensitizing Frequency=Min density*6.28
   a. The minimum density as described in (1a) is multiplied by 6.28 which is $2\pi$ 6) Download Sensitizing Frequency=HEX(65536-(500000/SeF))
   a. This equation is the hexadecimal input for the Sensitizing Frequency 7) Stimulating Freq=Max density*1.57
   a. The maximum density as described in (2a) is multiplied by 1.57 which is $\pi/2$ 8) Download Stimulating Frequency=HEX(65536-(500000/StF))
   a. This equation is the hexadecimal input for the Stimulating Frequency 9) k=(Maximum Density*Minimum Density)/("AvgDensity")
   a. k is used to calculate the pulse count and is derived from multiplying the maximum density by the minimum density and divided by the average density 10) Pulse Count Sensitizing=Sensitizing freq/k
    a. The pulse count for sensitizing is derived by dividing the sensitizing freq by k 11) Pulse Count Stimulating=Stimulating freq/k
    a. The pulse count for stimulating is derived by dividing the stimulating freq by k Algorithm for Low Proton Density 1) Minimum Density=$3^{rd}$ minimum of Pixel Value
   a. The minimum density is derived by discarding the 2 lowest recorded proton density pixel values (formula b) and the program will register the $3^{rd}$ lowest value as the "minimum density". This methodology is being used because the density value of air is very low and would distort the calculation.
   b. S=PD exp(-TE/T2)(1-exp(-TR/T1))(n)
      i. In this equation, S is the brightness (signal) measured at some particular point in the image—at some particular "pixel"; PD is "Proton Density", the number of hydrogen atoms in the region corresponding to that pixel; and T1 and T2 are the corresponding time constants for that pixel.

2) Maximum Density=$3^{rd}$ Maximum of Pixel Value
   a. The maximum density is derived by discarding the 2 highest recorded proton density pixel values (formula b) and the program will register the $3^{rd}$ highest value as the "maximum density". This methodology is being used because the density value of bone is very high and would distort the calculation.
   b. S=PD exp(-TE/T2)(1-exp(-TR/T1))(n)
      i. In this equation, S is the brightness (signal) measured at some particular point in the image—at some particular "pixel"; PD is "Proton Density", the number of hydrogen atoms in the region corresponding to that pixel; and T1 and T2 are the corresponding time constants for that pixel.

3) Average Density=(Sum of Pixel Values/No. Of Pixel Values)
   a. The average density is derived by dividing the sum of the all the Pixel Values in the region of interest by the total number of pixels in the region of interest.

4) Skin To Target=Root((xe-xs)^2+(ye-ys)^2)
   a. The Skin to Target value is derived by the root value of xe (x axis target)-xs (x axis Skin) squared plus ye (y axis target)-ys(y axis skin) squared 5) Sensitizing Freq=Average density*3.14
   a. The average density as described in (3a) is multiplied by 3.14 which is $\pi$ 6) Download Sensitizing Frequency(65536-(500000/SeF))
   a. This equation is the hexadecimal input for the Sensitizing Frequency 7) Stimulating Freq=Max density*3.14
   a. The maximum density freq as described in (2a) is multiplied by 3.14 which is $\pi$ 8) Download Stimulating Frequency=HEX(65536-(500000/StF))
   a. This equation is the hexadecimal input for the Stimulating Frequency 9) k=(Maximum Density*Minimum Density)/("AvgDensity*3.14*3.14")
   a. k is used to calculate the pulse count and is derived from multiplying the maximum density by the minimum density and divided by the average density which is multiplied by $\pi*\pi$ 10) Pulse Count Stimulating=Stimulating freq/k
    a. The pulse count for stimulating is derived by dividing the stimulating freq by k
    If PCSt>=50 Then
    PCSt=50
    Else If PCSt<=10 Then
    PCSt=10

11) Pulse Count Sensitizing=(sensitizing freq/stimulating freq)*PCSt
    The pulse count for sensitizing is derived by dividing the sensitizing frequency by the stimulating frequency and multiplied by pulse count simulating.

FIG. 12 shows a pictorial representation of a human cell and organelles which may be useful in the discussion which follows. In the drawing, C-A desingates cilia; C-B designates microvilli; C-C is the smooth endoplasmic reticulum; C-D are centrioles; C-E designates the cell membrane; C-F designates the rough endoplasmic reticulum; C-G are ribosomes; C-H designates the cytoplasm; C-I is a lysosome; C-J is mitochondria; C-K designates the nuclear membrane; C-L designates nucleus; C-M designates nucleolus; C-N designates chromatin; C-O designates the Golgi apparatus. Other structures may be present, and not shown, but are not relevant to the discussion herein.

Effect of SPMF Therapy in Tissue Degeneration Processes:

Even though there have been many advances in molecular biology and genetics, no uniform genetic or DNA damage pattern has been demonstrated in all types of cancers. Despite heterogeneity of cancer there are certain common features in all types of cancers, for example cancerous tissue is morphologically and functionally more primitive than its tissue of origin, has uncontrolled growth, has capacity to invade surrounding tissue, metastasize at different sites and derive its energy by glycolysis and the cells have low membrane potential (e.g., -15 mV to -30 mV).

Furthermore, the observation that fusion of normal cytoplasm with malignant cell nucleus yields 0% tumor while fusion of normal cells with malignant cell cytoplasm, produce cells with 97% of malignancy. This points to the fact that DNA damage is not the cause, but the result of unregulated, excessive proliferation of cells and loss of self-correcting mechanism. The cause of carcinogenesis lies in the microenvironment of nucleus, which is cell membrane, electron-proton homeostasis and reversion to glycolytic state.

Role of Transmembrane Potential in Carcinogenesis:

All living cells have membrane potential of about -70 mv. In healthy tissue inside of cell is negative relative to exterior, but when tissues are injured sodium & water flow into cells with loss of potassium, magnesium & zinc, lowering the cell membrane potential.

Healthy cell membrane potential is strongly linked to membrane transport mechanism as well as DNA activity and protein synthesis. Therefore the injured cells which cannot maintain normal cell membrane potential will have electronic dysfunction that will impede repair and regeneration process.

It is a well known fact that the cell membrane potential of cancer cells is about -15 mV to about -30 mV. Exposure of cancer cells to SPMF normalizes this potential, thereby arresting the process of cell proliferation. A cascade of effects follows normalization of cell membrane potential, i.e. increased influx of Calcium, Potassium ions and Oxygen and efflux of Na and $H_2O$ out of cells, and reduction in intracellular acidity. SPMF also increases the impedance of mitochondrial membrane potential and restores energy production.

In 1971, Cone postulated a functional relationship between transmembrane potential (TMP) and mitotic activity in general, including both normal, proliferative activity (eg, growth, healing wounds) and malignancy. Specifically he proposed that cells with normal TMP demonstrated virtual absence of mitotic activity while cells with low TMP showed greatly increased proliferation. He demonstrated that electrical transmembrane potential is correlated to degree of mitotic activity similar structural alteration could occur in the mitochondrial membrane affecting oxidative phosphorylation.

Normal electrical charge of cell membrane (Steve Haltiwanger's article on electrical nutrition) is maintained both by normal structure of membrane and it's mineral concentration in proper proportion which in turn is required for normal cellular potential & metabolic activity.

Deviations or abnormalities in cancer cells are as follows (Haltiwanger);

Cancerous tissue and less differentiated regenerating tissues are more electro negative and cells in these tissues have cell membranes that exhibit different electrochemical properties and a different distribution of electrical charges than normal tissues thereby making them less efficient in their production of cellular energy (ATP).

Further cancer cells have altered membrane composition and membrane permeability, which results in the movement of potassium, magnesium and calcium out of the cell and the accumulation of sodium and water into the cell, resulting in the cell having have higher intracellular Na+ ion concentration & lower intra cellular K+, Ca+, and Mg+ ion concentration. This higher intracellular concentration of sodium ions maintain TMP at much lower level, leading to carcinogenesis as also causing them to be more spherical & have different geometry than normal cells and this swelling in turn leads to disruption in the normal signaling of the cell.

Cancer cells also have different lipid and sterol content than normal cells.

When injury occurs in the body, normal cells proliferate and replace the damaged or destroyed cells with new cells or scar tissue. The characteristic feature of proliferating cells or cancer cells is that their TMP is lower than normal cells (Cone 1975). After the repair is completed, the cells stop proliferating and their TMP returns to normal due to contact inhibition with other cells and this proliferation of cells is organized.

While in cancer cells, the contact inhibition does not exist due to disrupted electrical connection between cells and their TMP is maintained at lower level than normal healthy cells. Cancer cells become independent of normal cell signal thereby have desynchronized and disorganized growth.

ATP is manufactured as a result of several cell processes including fermentation, respiration and photosynthesis. Most commonly the cells use ADP as a precursor molecule and then add a phosphorus to it. In eukaryotes this can occur either in the soluble portion of the cytoplasm (cytosol) or in special energy-producing structures called mitochondria. Charging ADP to form ATP in the mitochondria is called chemiosmotic phosphorylation. This process occurs in specially constructed chambers located in the mitochondrion's inner membranes.

The mitochondrion itself functions to produce an electrical chemical gradient—somewhat like a battery—by accumulating hydrogen ions in the space between the inner and outer membrane. This energy comes from the estimated 10,000 enzyme chains in the membranous sacks on the mitochondrial walls. Most of the food energy for most organisms is produced by the electron transport chain. Cellular oxidation in the Krebs cycle causes an electron build-up that is used to push H+ ions outward across the inner mitochondrial membrane.

As the charge builds up, it provides an electrical potential that releases its energy by causing a flow of hydrogen ions across the inner membrane into the inner chamber. The energy causes an enzyme to be attached to ADP which catalyzes the addition of a third phosphorus to form ATP. Plants can also produce ATP in this manner in their mitochondria but plants can also produce ATP by using the energy of sunlight in chloroplasts as discussed later. In the case of eukaryotic animals the energy comes from food which is converted to pyruvate and then to acetyl coenzyme A (acetyl CoA). Acetyl CoA then enters the Krebs cycle which releases energy that results in the conversion of ADP back into ATP.

The more protons there are in an area, the more they repel each other. When the repulsion reaches a certain level, the hydrogen ions are forced out of a revolving-door-like structure mounted on the inner mitochondria membrane called ATP synthase complexes. This enzyme functions to reattach the phosphates to the ADP molecules, again forming ATP.

The ATP synthase revolving door resembles a molecular water wheel that harnesses the flow of hydrogen ions in order to build ATP molecules. Each revolution of the wheel requires the energy of about nine hydrogen ions returning into the mitochondrial inner chamber. Located on the ATP synthase are three active sites, each of which converts ADP to ATP with every turn of the wheel. Under maximum conditions, the ATP synthase wheel turns at a rate of up to 200 revolutions per second, producing 600 ATPs during that second.

ATP is used in conjunction with enzymes to cause certain molecules to bond together. The correct molecule first docks in the active site of the enzyme along with an ATP molecule. The enzyme then catalyzes the transfer of one of the ATP phosphates to the molecule, thereby transferring to that molecule the energy stored in the ATP molecule. Next a second molecule docks nearby at a second active site on the enzyme. The phosphate is then transferred to it, providing the energy needed to bond the two molecules now attached to the enzyme. Once they are bonded, the new molecule is released. This operation is similar to using a mechanical jig to properly position two pieces of metal which are then welded together. Once welded, they are released as a unit and the process then can begin again.

Apoptosis; Santi Tofani, et al demonstrated that electromagnetic fields cause anti-tumor activity and significant increase in apoptosis in tumors of treated animals together with reduction in immuno-reactive p53 expression. Xiaoqi Liu, found that an overabundance of the polo-like kinase 1, or Plk1, molecule during cell growth, as well as a shortage of the p53 molecule, will lead to tumor formation. Studies in Liu's laboratory showed that the Plk1 molecule indirectly attacks p53 in a process called ubiquitination which provides the mechanism for how p53 loses its function in cancer cells. The tumor-suppressor protein p53 accumulates when DNA is damaged due to a chain of biochemical reactions. Part of this pathway includes alpha-interferon and beta-interferon, which induce transcription of the p53 gene and result in the increase of p53 protein level and enhancement of cancer cell-apoptosis. p53 prevents the cell from replicating by stopping the cell cycle at G1, or interphase, to give the cell time to repair, however it will induce apoptosis if damage is extensive and repair efforts fail. Any disruption to the regulation of the p53 or interferon genes will result in impaired apoptosis and the possible formation of tumors.

The tumor-suppressor protein p53 accumulates when DNA is damaged due to a chain of biochemical reactions. Part of this pathway includes alpha-interferon and beta-interferon, which induce transcription of the p53 gene and result in the increase of p53 protein level and enhancement of cancer cell-apoptosis. p53 prevents the cell from replicating by stopping the cell cycle at G1, or interphase, to give the cell time to repair, however it will induce apoptosis if damage is extensive and repair efforts fail. Any disruption to the regulation of the p53 or interferon genes will result in impaired apoptosis and the possible formation of tumors.

The tumor-suppressor protein p53 accumulates when DNA is damaged due to a chain of biochemical reactions. Part of this pathway includes alpha-interferon and beta-interferon, which induce transcription of the p53 gene and result in the increase of p53 protein level and enhancement of cancer cell-apoptosis. p53 prevents the cell from replicating by stopping the cell cycle at G1, or interphase, to give the cell time to repair, however it will induce apoptosis if damage is extensive and repair efforts fail. Any disruption to the regulation of the p53 or interferon genes will result in impaired apoptosis and the possible formation of tumors.

The process of apoptosis is controlled by a diverse range of cell signals, which may originate either extracellular (extrinsic inducers) or intracellular (intrinsic inducers). Extracellular signals may include toxins, hormones, growth factors, nitric oxide or cytokines, and therefore must either cross the plasma membrane or transduce to effect a response. These signals may positively (i.e., trigger) or negatively (i.e., repress, inhibit, or dampen) affect apoptosis. (Binding and subsequent initiation of apoptosis by a molecule is termed positive induction, whereas the active repression or inhibition of apoptosis by a molecule is termed negative induction.)

A cell initiates intracellular apoptotic signaling in response to a stress, which may bring about cell suicide. The binding of nuclear receptors by glucocorticoids, heat, radiation, nutrient deprivation, viral infection, hypoxia and increased intracellular calcium concentration, for example, by damage to the membrane, can all trigger the release of intracellular apoptotic signals by a damaged cell. A number of cellular components, such as poly ADP ribose polymerase, may also help regulate apoptosis.

Before the actual process of cell death is precipitated by enzymes, apoptotic signals must cause regulatory proteins to initiate the apoptosis pathway. This step allows apoptotic signals to cause cell death, or the process to be stopped, should the cell no longer need to die. Several proteins are involved, but two main methods of regulation have been identified: targeting mitochondria functionality, or directly transduction of the signal via adaptor proteins to the apoptotic mechanisms. Another extrinsic pathway for initiation identified in several toxin studies is an increase in calcium concentration within a cell caused by drug activity, which also can cause apoptosis via calcium binding protease calpain.

Many pathways and signals lead to apoptosis, but there is only one mechanism that actually causes the death of a cell. After a cell receives stimulus, it undergoes organized degradation of cellular organelles by activated proteolytic caspases. The characteristic changes of a cell undergoing Apoptosis start with the breakdown of the proteinaceous cytoskeleton by caspases causing cell shrinkage and rounding, the cytoplasm appears dense and the organelle tightly packed the process of pyknosis starts with chromatin undergoing condensation which is a hallmark of Apoptosis. Further the nuclear envelope becomes discontinuous and the process of Karyorrhexis (DNA fragmentation). At this time the cell membrane forms irregular blebs and starts to break apart into vesicles called apoptotic bodies which are then phagocytosed.

Apoptosis progresses quickly and its products are quickly removed, making it difficult to detect or visualize. During karyorrhexis, endonuclease activation leaves short DNA fragments, regularly spaced in size. These give a characteristic "laddered" appearance on agar gel after electrophoresis. Tests for DNA laddering differentiate apoptosis from ischemic or toxic cell death.

The removal of dead cells by neighboring phagocytic cells has been termed efferocytosis. Dying cells that undergo the final stages of apoptosis display phagocytotic molecules, such as phosphatidylserine, on their cell surface. Phosphatidylserine is normally found on the cytosolic surface of the plasma membrane, but is redistributed during apoptosis to the extracellular surface by a hypothetical protein known as scramblase. These molecules mark the cell for phagocytosis by cells possessing the appropriate receptors, such as macrophages. Upon recognition, the phagocyte reorganizes its cytoskeleton for engulfment of the cell. The removal of dying cells by phagocytes occurs in an orderly manner without eliciting an inflammatory response.

Role of Centrioles:

Centrioles are among the simplest structures within the eukaryotic cell, but they play a surprisingly complex set of roles. They are composed of nine parallel protein rods, which form ribbed, hollow tubes with more than a passing resemblance to microscopic rigatoni. In pairs, centrioles form the heart of the centrosome, which hovers near the nucleus and coordinates chromosome division during mitosis. Singly, and docked to the plasma membrane, they dictate the position and growth of fl agella and cilia, the hair-like extensions whose coordinated beatings can either move the cell through liquid or move liquid across the cell's surface. They replicate themselves by a templating process, without any direct instruction from the cell's nucleus. Marshall, Wallace F, 2007.

Centrioles play a role in inheritance of tumorigenic properties which contain differently encoded RNA sequences stacked in a definite order. During mitosis, these RNA sequences are released in a pattern that possibly cause changes in the status of repressed and potentially active genes thereby affecting the morphogenetic status of a cell. In each mitotic division, one of the RNA sequences is released and 'lost' so the centrioles of daughter cells contain one RNA sequence less than the centrioles of the maternal cell. The number of RNA sequences contained in centrioles decreases after each mitotic division. The last RNA sequence triggers the processes of programmed death (i.e. apoptosis). Thus, the number of sequences correspond to the number of possible mitotic divisions, counting down from the cell having the first orthogenetic status to the last offspring cell having the final morphogenetic status the "Hayflick limit".

Microtubules may be a source of endogenous cellular EMF. We have presented here a simple model of MT EMF geometry and properties. Endogenous cellular EMF may contribute significantly to the dynamic and spatial organization of cellular processes and structures.

FIG. 13. Modifications to the centriole in the normal cell cycle and mitosis (not to scale: centrioles are about 750 nm in length and 200 nm outer m diameter, much smaller than mitotic spindles). Center: centriole as two perpendicular cylinders. Clockwise from center (G1, S, and G2 occur during "Interphase" which precedes and follows mitosis): in G1 phase centriole cylinders separate. In S phase centrioles replicate, each cylinder forming a new perpendicular cylinder via connecting filamentous proteins. G2 phase: centrioles separate and begin to migrate. Prophase: centrioles move apart and microtubules form the mitotic spindles between the centrioles. Metaphase: mitotic spindles attach to centromeres/kinetochores on opposite sides of each paired chromosome (only four of which are shown). Anaphase: paired chromosomes separate into sister chromatids and are moved by (and move along) mitotic spindles to newly forming daughter cells.

FIG. 13. Abnormal centriole activities in mitosis leading to aneuploidy. As in FIGS. 1 and 2 except that defective centriole replication continues in G2 producing three centrioles which form abnormally distributed spindles in prophase and abnormal chromosome distribution/genotypes in metaphase and anaphase. This results in chromosomes mal distributed among three daughter cells.

Centrioles do not directly drive the assembly of the spindle, rather they recruit a centrosome which sculpts the inherently self-assembling spindle into a more precise form, and they then act as structural reinforcements to allow the spindle pole to resist the forces it meets during mitosis. Such functions in mitotic fidelity may help explain the near-universality of supernumerary centrioles in solid tumor cells [Brinkley and Goepfert, 1998; Doxsey, 2002]. Most tumor cells have abnormal numbers of centrioles, but if this simply resulted in cell death, the tumor would not progress.

SPMF Signals Producing Order in Cancer Cells:

SPMF effects the regulation of cell membrane potential and gap junction intercellular communication aberrations thereby impacting carcinogenesis and neutralizing these effects.

SPMF Therapy targets the basic cellular abnormalities and normalizes cellular functions by restoring transmembrane potential, thereby normalizing the disrupted or aberrant intracellular and intercellular connection, preventing electron efflux which is responsible for absolute decrease in TMP, restoring gap junction inter cellular communication with surrounding normal cells by regulating the passage of Ca+ ions and cAMP.

SPMF further restores the p53 function as cell mitosis is arrested by the change in orientation of centrioles during cell division which prevents Cyclin E-dependent reduplication of both centrioles and centrosomes in a single cell division cycle thereby irreversibly marking the cell for apoptosis. The SPMF also reduces blood volume density in tumor thus decreasing chances of distant metastasis.

Clinical Examples of Cancer Treatment

Since 2009, 31 patients have been treated in a clinical trial. Some of the benefits of SPMF treatment include:
  Improves quality of life;
  Halts Progression of the disease;
  Significantly decreases pain;
  Cure maybe long lasting and the progress of the disease is halted
  Alternative to Radiation Therapy
  It is an outpatient treatment
  Patient Case History for 2 Patients Treated with SPMF.
  Case Summary: 30 year old female Diagnosis—Synovial Sarcoma with Mets in Right lung and Mediastinal Lymph Nodes
  Diagnosis—Synovial Sarcoma with Mets in Right lung and Mediastinal Lymph Nodes;
  Presentation—July 2007, progressively increasing swelling in the lower Post Chest wall;
  CT Scan; FIG. 9A
  FNAC—24 Aug. 2007, Inconclusive;
  Surgery—Excision of soft tissue mass on 7 Sep. 2007, at Sydney, Australia;
  Post Op Biopsy—Synovial Sarcoma;
  Post op Radiotherapy—25#, Oct. 10, 2007 to Dec. 4, 2007;
  Chemotherapy—Ifosphamide and doxorubicin—2#, from Jan. 1, 2008 onwards, stopped because of side effects;
  Dec. 25, 2008—PET CT well defined nodule in the apical segment of lower lobe of right lung, S/O metastases;
  Jan. 16, 2009—Surgery-Rt. Lower Lobectomy done;
  Post op Biopsy—Rt. Lower lung Nodule—conclusive of metastatic Synovial Sarcoma;
  July 2009—CT Chest+abdomen-Multiple lobulated Pleural masses and a mass in Rt. Perihilar region, the surgical Clips in the Left Lumbar region and Lower lobe Bronchus in situ;
  Mar. 23, 2009—CT chest/abdomen—No evidence of Metastasis;
  Jul. 22, 2009—Biopsy of Lung Mass—recurrence of Monoplastic Synovial Sarcoma; spindle shaped cells focally +ve for EMA;
  Presentation at SBF Healthcare Pvt. Ltd;
  Breathlessness on walking;
  Puffiness and Tightness of lower half of face and upper chest;
  Severe pain in the Rt. lower chest (patient on Fentanyl patch, 50 mg+NSAIDS);
  Wt. loss 4 kgs in past 2 months;
  Reduced appetite and energy levels;
  Pre-treatment CT Sep. 19, 2009 FIG. 9B;
  Course of treatment at SBF Healthcare;
  SPMF Therapy—Sep. 20, 2009 to Oct. 17, 2009;
  Mid-treatment CT Oct. 7, 2009; FIG. 9C;
  Post-treatment PET/CT Oct. 29, 2009; FIG. 9D;
  Post-treatment CT Nov. 5, 2009; FIG. 9E;
  Palliative RT for SVC syndrome, 12 Gy/3#—Oct. 19, 2009, Oct. 21, 2009 and Oct. 22, 2009;
  10 days after QMR therapy, she was off the pain killer;
  Breathlessness reduced (Climbed 2 flights of stairs without breathlessness) Wt. stabilized.
  FIG. 10; Case Summary; 55 Male Diagnosis—Left Posterior Frontal—GBM (Who Grade—IV)
  Diagnosis—Left Posterior Frontal—GBM (WHO Grade—IV) Onset: 26 Mar. 2007;
  Presenting symptoms-seizure;
  MRI Brain dated May 21, 2007, films only;
  Small dense nodular enhancing lesion in left frontal lobe (6×5×6 cms);
  Multiple small chronic lacunar infarcts B/L centrum semiovale, parietal lobe & periventricular region;
  Given ATT and antiepileptic drugs for 06 months.
  Recurrence of symptoms;
  MRI Brain dated Dec. 27, 2007: Well defined nodular enhancing region in Right frontal convexity 6×4 cms with perilesional edema and adjoining Meningial enhancement;
  Surgery Left posterior frontal craniotomy with excision of tumor on Oct. 1, 2008;
  HPR: Diffuse infiltrating astrocytoma Gr-II Improved symptomatically;
  Post-op RT-54 Gy/30# dated Mar. 10, 2008 to Apr. 25, 2008;
  Recurrence of symptoms—Generalized Seizure and Right Hemipareses in November/December 2008;
  Second Surgery—Left posterior frontal craniotomy with excision of tumor on Jan. 1, 2009.
  HPR: GBM Grade IV dated Jan. 14, 2009. (Reported at National Institute of Mental health and neurosciences, Bangalore, India.) Symptomatic improvement with residual right Hemipareses;
  Patient presented at SBF Healthcare Pvt. Ltd in March 2009 with complaints of Right Hemipareses, pain in both legs and headache;
  SPMF Therapy—Apr. 4, 2009 to Jan. 5, 2009 (28 days);
  Post SPMF: No headache and leg pain. Muscle power improved in Right upper and lower limbs;
  Pre SPMF MRI: lesion size 2.2×3.8 Cms. FIG. 10A, B, C;
  Immediate Post SPMF: Lesion size 2.0×3.5 Cms. FIG. 10D, E, F;

Post SPMF 04 months: lesion size 1.4×1.5 Cms. FIG. 10G, H, I;

Treatment Protocols for Tissue Regeneration—

Figure 17B:
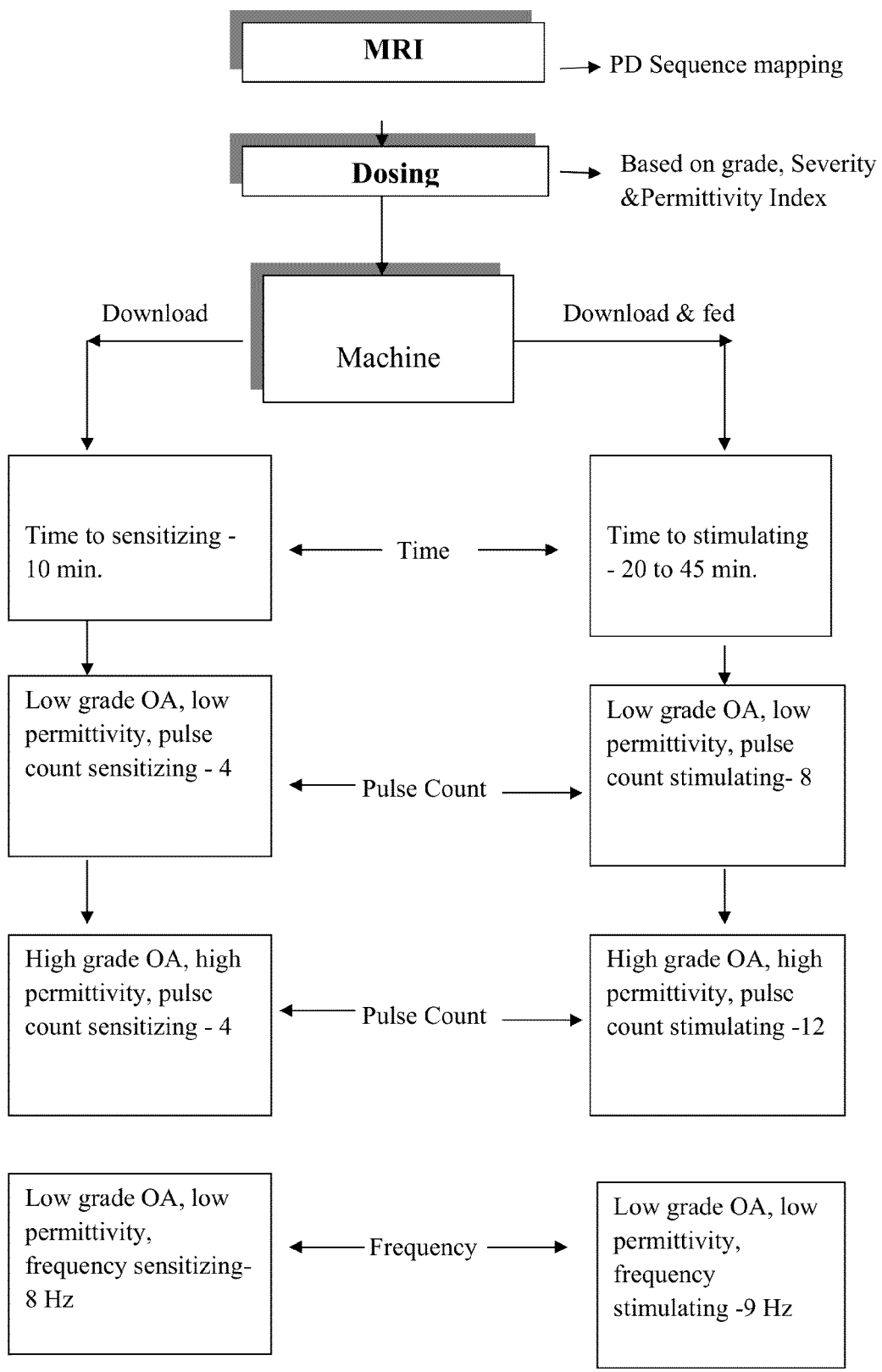
FIG. 17B is a flow chart of a proposed mechanism of action in accordance with an embodiment of the invention.

The patient process flow chart for arthritis is illustrated in FIG. 17.

Treatment Protocols for Arthritis a predetermined dose profile is preformed based on the grade and severity of the arthritis and the permittivity index. Patients who have early stage arthritis will receive a low sensitizing frequency in the range of 8 Hz to 20 Hz, a stimulating frequency in the range of 12 Hz to 40 Hz. Patients who have severe arthritis and a high permittivity index will receive a sensitizing frequency of 10 Hz, and a stimulating frequency up to 40 Hz. as per the table.

TABLE

| Class | Sensitizing Frequency | Stimulating Frequency |
| --- | --- | --- |
| High Permittivity Grade - I | 8 | 9 |
| High Permittivity Grade - II | 8 | 10 |
| High Permittivity Grade - III & above | 8 | 11 |
| Low Permittivity Grade - I | 8 | 10 |
| Low Permittivity Grade - II | 8 | 12 |
| Low Permittivity Grade - III & above | 8 | 14 |

Articular Cartilage Regeneration and Repair

In spite of medical and surgical advances in treatment of osteoarthritis, outcome is still under debate. This is attributable in large part to the intrinsic biology of cartilaginous tissue, which limits its capacity to self regenerate. Because cartilage is non-vascularized and non-innervated, the normal mechanism of tissue repair involving humoral factors and recruitment of stem/progenitor cells to the site of damage does not apply. Moreover, the low density within cartilaginous tissue reduces the likelihood of local chondrocyte contributing to self-regeneration. Targeted stimulation of endogenous repair mechanism remains specific goal. Achieving this goal depends on understanding of cellular and molecular mechanisms of joint formation, articular cartilage injury and repair.

When hyaline cartilage of the knee is destroyed arthritis generally follows. The diffuse articular cartilage damage of degenerative or inflammatory arthritis is not amenable to cartilage repair procedures. There are two main types of injury to articular cartilage. The first is acute and transient, consisting of loss of proteoglycan and other non-collagenous tissue. Such an injury may occur following abnormal joint loading or the use of anti-inflammatory drugs. Cartilage generally makes a complete recovery from this type of injury. The second type of injury involves mechanical disruption of the collagen network. This results in significant loss of cells and lesions are generally irreversible and do not successfully heal. In the progression of OA, at an undefined time point, a transition is made from the first to the second type of injury.

Although repair of superficial defects in articular cartilage can be complete for fetal tissues, the same is not true for adult cartilage. There are several reasons why adult chondral defects do not adequately heal. First, the anti-adhesive nature of the cartilage matrix prevents stem cells migrating from neighboring synovium to adhere onto the cartilage surface. Second, there is insufficient chemotactic signal from the site of injury, as the endogenous chondrocyte population is too sparse. The amount of cytokines and growth factor released is too small. Additionally, despite attempts by endogenous chondrocytes adjacent to the cartilaginous effect to proliferate and migrate into the defect, they are sterically hindered in doing so by the collagenous matrix of articular cartilage. The chondrocytes have only a limited anabolic potential and are ill-equipped to deal with large tissue failures.

Causes of pain in osteoarthritis of Knee:
1. Synovial membrane inflammation
2. Microfractures of subchondral bone
3. Venous congestion of intraosseous space
4. Joint distention
5. Changed mechanical alignment
6. Bursal inflammation
7. Periosteal stretching due osteophytes
8. Depression SPMF Therapy in Osteoarthritis:

RPMF Therapy addresses all the above-mentioned abnormalities and causes the re-generation of cartilage and pain relief in patients of osteoarthritis; In Osteoarthritis cartilage, there is loss of collagen and proteoglycans preventing generation of piezoelectric stimulus or failure of this stimulus to stimulate the chondrocytes. Exposure of cartilage cells to SPMF re-creates the physiological piezoelectric stimulus. Centrioles are cylindrical structures, usually in pairs oriented at right angles to one another. The wall of each centriole cylinder is made of nine interconnected triplet microtubules, arranged as a pinwheel. The centro somal cycle is closely integrated with the chromosomal cycle in embryonic and somatic cells. In essence, it controls the cell cycle and cell division in most cells. Like chromosomes, centrioles are self-replicating organelles, which duplicate during inter-phase, when they are located close to the nucleus.

In humans, centrioles are formed in the fetal cartilage, but they disappear during adult life. They have been demonstrated to reappear during the regenerative process. Exposure of cartilage cells in osteoarthritis patients to specific regulated SPMF therapy fields leads to denovo-synthesis of centrioles from the microtubules and the protein surrounding them, leading to regeneration of cartilage cells.

Insulin-like growth factor-1 (IGF-1) is one of several growth factors that have been shown to have an anabolic effect on cartilage growth and differentiation. IGF-1 in synovial fluid (SF) is the main stimulatory factor responsible for PG synthesis by chondrocytes. There is evidence that IGF-1 insufficiency plays an etiologic role in OA. In OA cartilage there is enhanced expression of IGF-1 mRNA as chondrocytes attempt to repair damaged tissue. However, there is also a parallel, greater decrease in the responsiveness of chondrocytes to IGF-1. This is in part due to aging and in part due to the presence of inflammatory cytokines (i.e. IL-1). The net result is diminished anabolic potential for OA cartilage. SPMF Exposure increases the production of IGF-1, which may play an important role in facilitating chondrocyte adhesion and proliferation. SPMF Exposure also increases sulphate incorporation required for proteoglycan synthesis. SPMF exposure of cells up-regulates the HSR/HSF-1 pathway, delay cellular damage & stimulates the natural stress response and activates the repair process. Delaying the senescence of cells, the target would be heat shock protein axis, which is regulated by HSF-1. This pathway (HSP) is preferred to prevent protein damage. In Osteoarthritis cartilage, the chondrocytes have limited capacities to migrate to the cartilage defects and proliferate. SPMF Exposure of cells increases the synthesis of proteoglycans thereby facilitating migration of chondrocytes for healing the cartilage defects.

Relief of pain after few SPMF exposure is brought about by reduction in synovial inflammation that is due to reduction in gap junction mediated secretion of pro-inflammatory cytokines. SPMF beam stimulates the production opioid peptides activates mast cell and increase the electric capacity of muscular fibers. SPMF lowers the threshold of nociceptive afferents innervating the joint capsule, induced by arthritis.

Clinical Outcomes Osteoarthritis

Since 2009, treated over 150 patients in a commercialized model

Range of Motion (ROM) increased progressively in every patient

Figure 11A:
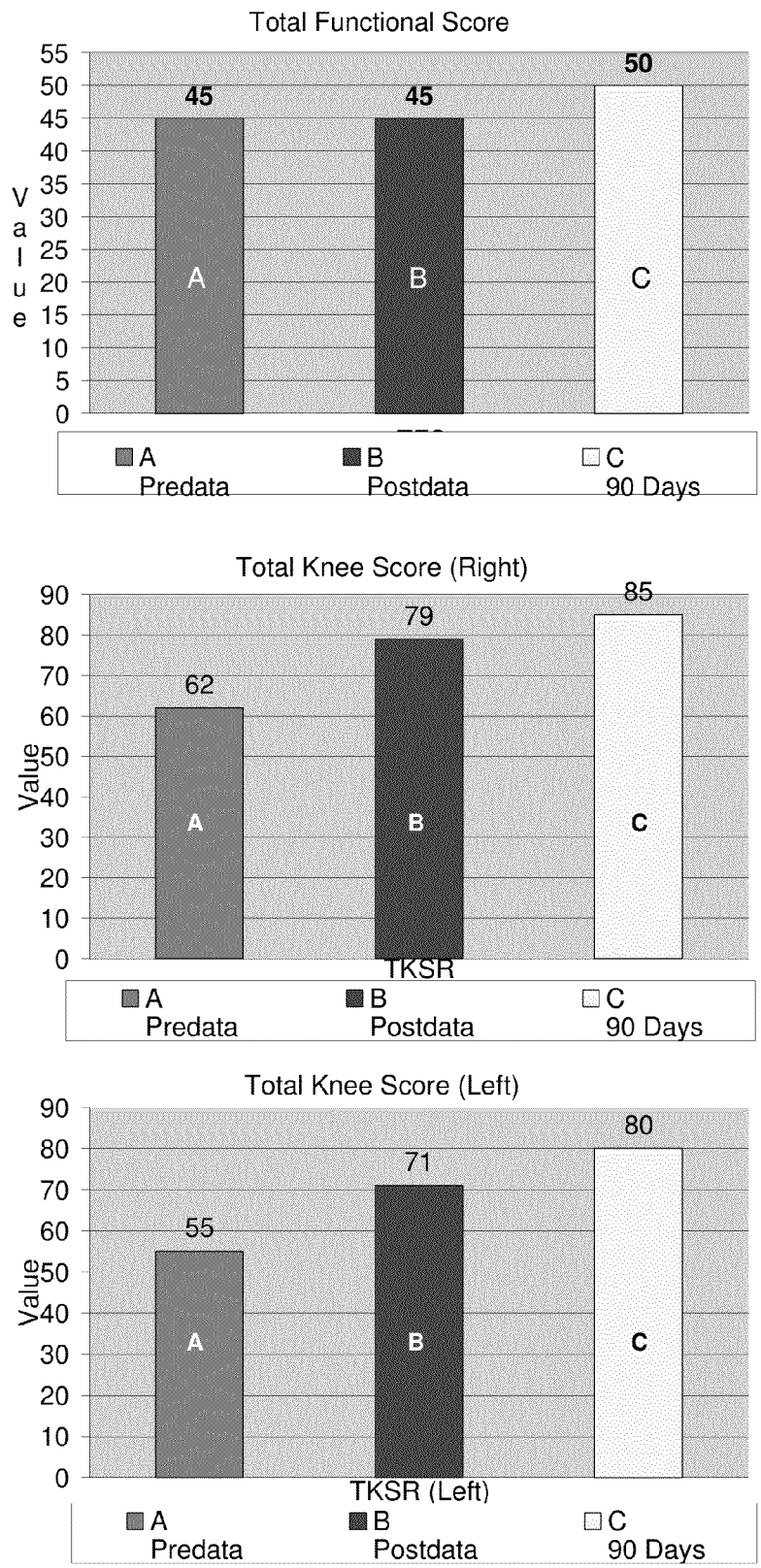
Figure 11A:
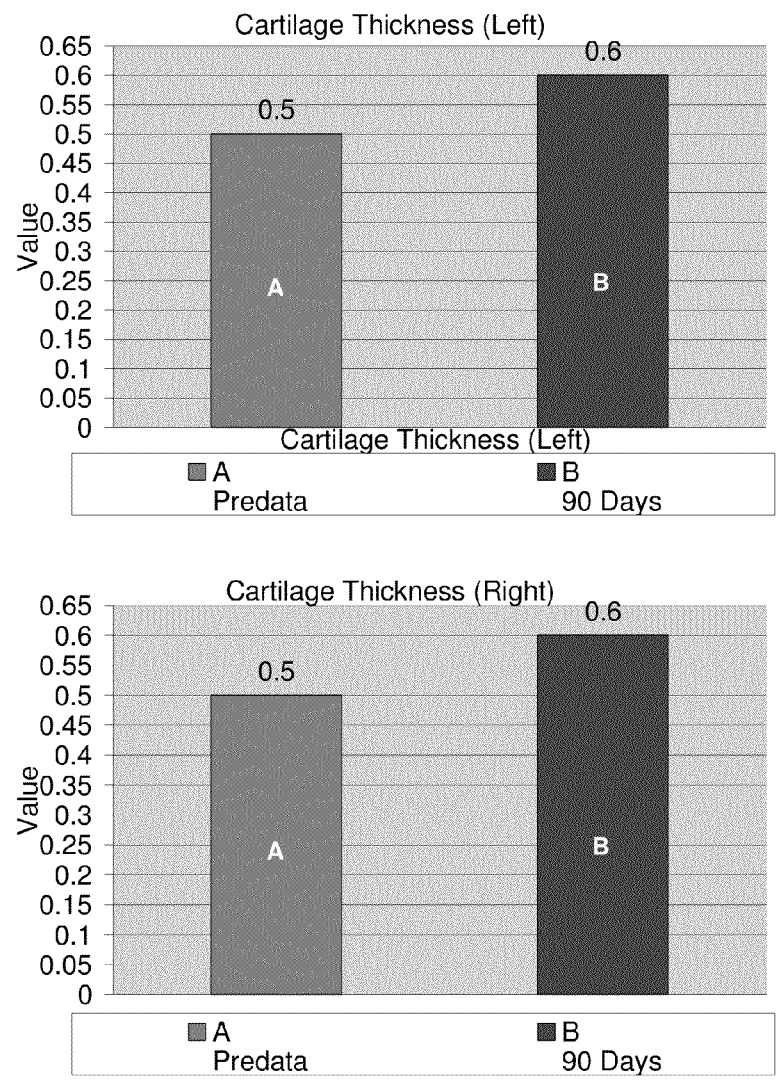

Total Functional Scores (TFS) and Total Knee Score (TKS) has improved in all patients, who were able to walk comfortably for considerable distances at the end of the treatment There was a significant increase in the cartilage thickness after SPMF therapy Improves stability and power of the knee joint Progress of the disease is halted Significantly decreases pain Cure is long lasting and the progress of the disease is halted Enables natural growth of cartilage and increases its thickness as against placement of foreign substance Alternative to knee replacement Both knees can be treated simultaneously It is an outpatient treatment Patients can carry on their normal activity during the treatment Patient case history;

FIGS. 11A, B, C, D, Case Summary; Osteo Arthritis

SPMF Treatment was performed for 21 days;

After 90 days of treatment the total knee score (TKS) increased from 55 to 80 illustrated in FIG. 11a, and the cartilage thickness increased from 0.05 mm to 0.06 mm illustrated in FIG. 11b,c,d;

Progress Report for SPMF Therapy, FIG. 1a;

MRI Image of the left knee Pre SPMF Therapy FIG. 11b;

MRI Image of right knee Pre SPMF Therapy FIG. 11c;

MRI Images of both knees Post SPMF Therapy MRI Images FIG. 11d;

Treatment Protocols for Neural Disorders & Neurodegenerative Diseases—

The patient process flow chart for neuro is illustrated in FIG. 18.

Neuro degeneration, the progressive loss of nerve cells, occurs in aging and in neurodegenerative disorders, such as Alzheimer's, Parkinson's, ALS, and Huntington's disease, in retinal degeneration, and other damage to sensory systems (e.g., visual, auditory, somatosensory), in stroke, head and spinal trauma, epilepsy, in drug and alcohol abuse, in infectious diseases, in exposure to industrial and environmental toxicants, and, perhaps, in mental disorders and chronic pain. Primarily, these diseases are characterized by chronic and progressive loss of neurons in discrete areas of the brain, causing debilitating symptoms such as dementia, loss of memory, loss of sensory or motor capability, decreased overall quality of life and well-being, disability, and eventually, premature death.

Classification:

Neurodegenerative diseases are crudely divided into two groups according to phenotypic effects, although these are not mutually exclusive: Conditions causing problems with movements, such as ataxia, and Conditions affecting memory and related to dementia List of neurodegenerative diseases and conditions:

Adrenoleukodystrophy (ALD), Alcoholism, Alexander's disease, Alper's disease, Alzheimer's disease, Amyotrophic lateral sclerosis (Lou Gehrig's Disease), Ataxia telangiectasia, Batten disease (also known as Spielmeyer-Vogt-Sjögren-Batten disease), Bovine spongiform encephalopathy (BSE), Canavan disease, Cockayne syndrome, Corticobasal degeneration, Creutzfeldt-Jakob disease, Familial fatal insomnia, Frontotemporal lobar degeneration, Huntington's disease, HIV-associated dementia, Kennedy's disease, Krabbe's disease, Lewy body dementia, Neuroborreliosis, Machado-Joseph disease (Spinocerebellar ataxia type 3), Macular Degeneration, Multiple System Atrophy, Multiple sclerosis, Narcolepsy, Niemann Pick disease, Parkinson's disease, Pelizaeus-Merzbacher Disease, Pick's disease, Primary lateral sclerosis, Prion diseases, Progressive Supranuclear Palsy, Refsum's disease, Sandhoff disease, Schilder's disease, Subacute combined degeneration of spinal cord secondary to Pernicious Anaemia, Spielmeyer-Vogt-Sjogren-Batten disease (also known as Batten disease), Spinocerebellar ataxia (multiple types with varying characteristics), Spinal muscular atrophy, Steele-Richardson-Olszewski disease, Tabes dorsalis, Toxic encephalopathy, Path physiology and others.

Neuro degeneration is often caused by mis folding of proteins (prions) in such way that they can no longer perform their cellular functions and instead triggers equivalent modifications in normal proteins, thus creating a cascade of damage that eventually results in significant neuronal death. In humans, this can cause Creutzfeldt-Jakob disease or variant CJD (Mad Cow Disease).

Normally, neuro degeneration begins long before the patient experiences any symptoms. It can be months or years before any effect is felt. Symptoms are noticed when many cells die or cease to function.

Additionally, the role of microglia in modulating neuro inflammation in CNS-related degeneration is currently being studied.

Treatment:

For most neurodegenerative diseases, there is little or no treatment; at best, treatments are symptomatic in nature and do not prevent or slow the progression of disease. Clearly, an understanding of pathological progression can help to identify points of intervention and lead to promising therapeutic approaches. A fundamental approach for reducing the burden of neurodegenerative diseases is thus to slow or halt progression, and ultimately, to prevent the onset of the disease process. Strategies for neuro rescue, neuro repair, or neuroprotection are being actively pursued by the basic, translational, and clinical research communities. As our population ages, the already enormous impact of neuro degeneration on society will become even larger without better prevention and treatment.

Initial treatment for neurodegenerative disorders is dependent on diagnosis of the underlying condition. Presently, few therapies are available for the treatment of most neurodegenerative diseases. Treatment with L-dopa can inhibit symptoms of Parkinson's Disease for a short time, but is thought to subsequently accelerate the progression of symptoms. Efforts are being made to develop therapies for Alzheimer's Disease in order to stabilize cognitive function.

Epidemiology

Stem cell technology and stem cell treatments, as well as Gene therapy are gaining increasing attention for the treatment of neurodegenerative diseases. Research is underway into biomarkers as part of an attempt to understand the progression of certain types of neurodegenerative disease. In theory, if relevant biomarkers were identified, people could be treated for such diseases prior to onset of symptoms, thus resulting in a significant extension of their normal functional lifespan. Yet, however, the science of biomarkers is in its infancy and consequently diagnosis of neurodegenerative disease tends to occur after the patient has already suffered the majority of the neural damages. However, the use of electromagnetic fields in neural regeneration has been tried earlier with little success. With this method, and the protocols used the efficacy of treatment is enhanced as the SPMF can be targeted on the specific areas (region of interest) using selective algorithms based on tissue type.

The algorithms used in neuro degenerative diseases are as follows:

First, a proton density, MRI of the brain is performed, then the area mapping is carried out based on the algorithm described below, and then the dose pattern is mapped out for the patient.

NEURO DEGENERATIVE DISEASES (Range 30-120 Hz)

Flow Chart FIG. 18 is a flow chart for patient treatment of neuro
  MinimumDensity = $3^{rd}$ minimum of PixelValue
  MaximumDensity = $3^{rd}$ Maximum of PixelValue
  AverageDensity = (Sum of Pixel Values \ No. Of Pixel Values)
  SkinToTarget = Root((xe−xs)^2 +(ye−ys)^2 )
  Sensitizing frequency= ( X ) = Min density*2 Π
  Con__Sen__Freq= (X) / ($\Pi^2$ * e)       e ≈ 2.718 (Euler's constant)
  If Sensitizing freq >= 60 Then
  Sensitizing freq = 60
  Else If Sensitizing freq <= 30 Then
  Sensitizing freq = 30
  6) DownloadPul Sensitizing =HEX(65536-(500000 / Sensitizing freq))
  7) Stimulating Frequency = Y =Max density * (Π/2)
  Con__sti__freq= ( Y ) / ( $\Pi^2$ )
  If Stimulating Freq >= 120 Then
  Stimulating Freq =120
  ELSE If Stimulating Freq <= 80 Then
  Stimulating Freq = 80
  8)DownloadPul Stimulating =HEX(65536-(500000 / Stimulating Freq))
  9)k = Π * e       e ≈ 2.718 (Euler's constant)
  10)Pulse Cnt Sensitizing = Sensitizing freq / k
  11)Pulse Cnt Stimulating = Stimulating freq / k Clinical Data examined—Patient Dr. C aged 60 years patient of Spinocerebellar Ataxia 1 came with significant speech defects ataxia and hence has difficulty in walking since 2 years was unable to walk on a smooth surface without support and had episodes of frequent fall and she was unable to go to her clinic and continue her clinical practice. She was treated with SPMF therapy for 4 weeks after which she started showing improvement gradually and the next 3 months, her speech and gait improved to an extent that she could walk independently and she could go back to seeing patients in her clinic and in 6 months, she had almost reached normalcy.

Ménière's disease is an abnormality of the inner ear causing a host of symptoms, including vertigo or severe dizziness, tinnitus or a roaring sound in the ears, fluctuating hearing loss, and the sensation of pressure or pain in the affected ear. The disorder usually affects only one ear and is a common cause of hearing loss. Named after French physician Prosper Ménière who first described the syndrome in 1861.

The symptoms of Ménière's disease are associated with a change in fluid volume within a portion of the inner ear known as the labyrinth. The labyrinth has two parts: the bony labyrinth and the membranous labyrinth. The membranous labyrinth, which is encased by bone, is necessary for hearing and balance and is filled with a fluid called endolymph. When your head moves, endolymph moves, causing nerve receptors in the membranous labyrinth to send signals to the brain about the body's motion. An increase in endolymph, however, can cause the membranous labyrinth to balloon or dilate, a condition known as endolymphatic hydrops.

Many experts on Ménière's disease think that a rupture of the membranous labyrinth allows the endolymph to mix with perilymph, another inner ear fluid that occupies the space between the membranous labyrinth and the bony inner ear. This mixing, scientists believe, can cause the symptoms of Ménière's disease. Scientists are investigating several possible causes of the disease, including environmental factors, such as noise pollution and viral infections, as well as biological factors.

Symptoms:

The symptoms of Ménière's disease occur suddenly and can arise daily or as infrequently as once a year. Vertigo, often the most debilitating symptom of Ménière's disease, typically involves a whirling dizziness that forces the sufferer to lie down. Vertigo attacks can lead to severe nausea, vomiting, and sweating and often come with little or no warning.

Some individuals with Ménière's disease have attacks that start with tinnitus (ear noises), a loss of hearing, or a full feeling or pressure in the affected ear. It is important to remember that all of these symptoms are unpredictable. Typically, the attack is characterized by a combination of vertigo, tinnitus, and hearing loss lasting several hours. People experience these discomforts at varying frequencies, durations, and intensities. Some may feel slight vertigo a few times a year. Others may be occasionally disturbed by intense, uncontrollable tinnitus while sleeping. Ménière's disease sufferers may also notice a hearing loss and feel unsteady all day long for prolonged periods. Other occasional symptoms of Ménière's disease include headaches, abdominal discomfort, and diarrhea. A person's hearing tends to recover between attacks but over time becomes worse. There was no cure for Ménière's disease.

MENIERES DISEASE (Range 8-30 Hz)

MinimumDensity = 3rd minimum of PixelValue
  MaximumDensity = 3rd Maximum of PixelValue
  AverageDensity = (SumofPixelValues \ No. Of PixelValues)
  SkinToTarget = Root((xe−xs)^2 +(ye−ys)^2 )
  Sensitizing frequency= ( X ) = Min density*2 Π
  Con__Sen__Freq= (x) / (4 * Π)
  If Sensitizing freq >= 10 Then
  Sensitizing freq = 10
  Else If Sensitizing freq <= 8 Then
  Sensitizing freq = 8
  6) Download Pul Sensitizing =HEX (65536-(500000 / Sensitizing freq))
  7) Stimulating Frequency = (y) = Max density * (Π/2)
  Con__Sti__Freq= (y) / (4 * Π)
  If Stimulating Freq >= 30 Then
  Stimulating Freq = 30
  8)DownloadPul Stimulating =HEX(65536-(500000 / Stimulating Freq))
  9)k = (maxd * mind) / ("AvgDensity")
  10)PulseCnt Sensitizing = Sensitizing freq / k
  pcnt Sensitizing =4 /* Constant Value */
  11)PulseCnt Stimulating = Stimulating freq / k
  If pcnt Stimulating <= 4 Then
  pcnt Stimulating = 4
  Else If pcnt Stimulating >= 14 Then
  pcnt Stimulating = 14

Macular Degeneration (Degeneration of tissue) (medical condition usually of older adults that results in a loss of vision in the center of the visual field (the macula) because of damage to the retina)

Clinical Outcomes

Non-invasive procedure for treatment.

Significantly decreases pain.

No side effects.

Cure is long lasting and the progress of the disease is halted.

Enables natural growth of cells

It is an outpatient treatment.

Patients can carry on their normal activity during the treatment.

Although the invention has been described with reference to exemplary embodiments, it is not limited thereto. Those skilled in the art will appreciate that numerous changes and modifications may be made to the preferred embodiments of the invention and that such changes and modifications may be made without departing from the true spirit of the invention. It is therefore intended that the appended claims cover be construed to all such equivalent variations as fall within the true spirit and scope of the invention.

What is claimed is:

1. An apparatus for generating and applying a sequentially programmed magnetic field as a treatment to a desired tissue in a patient having a disease type, the apparatus comprising:
   a plurality of magnetic field generators to produce sequentially programmed pulsed magnetic fields at a focal region;
   wherein each of the plurality of magnetic field generators comprise:
      a funnel;
      a magnetically conductive hollow cylindrical base body extending at one end into the funnel;
      a magnetically conductive rod-like structure extending through said hollow cylindrical base body into said funnel; and
      an electrical coil wound around the hollow cylindrical base body and the funnel; and
   a switching system to control the pulsing in a sequential firing pattern in a range of about 0.1 Hz to about 2000 Hz dependent on the disease type and the treatment to be administered.

2. The apparatus of claim 1, further comprising:
   a tubular gantry for housing the magnetic field generators, wherein the magnetic field generators are fixed circumferentially on the tubular gantry in regular intervals of about 15 to about 90 degrees with respect to an adjacent magnetic field generator with reference to the central axis of said tubular gantry.

3. The apparatus of claim 2, wherein:
   the plurality of magnetic field generators are operatively coupled in mated, opposed pairs, such that said opposed pairs of magnetic field generators which are about 180 degrees opposite to each other in said tubular gantry are energized at the same time and out of phase so that a net magnetic flux passes through the focal region.

4. The apparatus of claim 1, further comprising:
   a tubular gantry, defining from 1 to 12 transverse planes with respect to the central axis of said gantry along which said plurality of magnetic field generators are located;
   the plurality of magnetic field generators are disposed in the apparatus such that in each transverse plane, 2-24 magnetic field generators are disposed radially over the circumference of the gantry; and diametrically opposite magnetic field generators of the plurality of magnetic field generators are operatively coupled to form 1 to 12 such pairs wherein each of the pairs can be excited to generate a magnetic field.

5. The apparatus of claim 4, wherein circumferentially adjacent magnetic field generators of the plurality of magnetic field generators in each transverse plane are displaced from each other by regular intervals of about 15 to about 180 degrees.

6. The apparatus of claim 1, further comprising:
   a computer coupled to and controlling the magnetic field generators, wherein the computer controls the magnetic field generators based on the disease type;
   computer software stored on the computer for calculating a duration of exposure, pulse frequency, and firing frequency depending on the patient and the disease type.

7. The apparatus according to claim 1, wherein said rod-like structure defines a frusto-conical end which extends into said funnel.

8. The apparatus of claim 1, wherein each magnetic field generator further comprises an external magnetic shield limiting leakage of magnetism except through said funnel.

9. The apparatus of claim 1, wherein each magnetic field generator has an impedance of from about 80 to about 90 ohms.

* * * * *